(12) United States Patent
Osorio

(10) Patent No.: US 11,272,874 B2
(45) Date of Patent: *Mar. 15, 2022

(54) CONTINGENT CARDIO-PROTECTION FOR EPILEPSY PATIENTS

(71) Applicant: Flint Hills Scientific, L.L.C., Lawrence, KS (US)

(72) Inventor: Ivan Osorio, Leawood, KS (US)

(73) Assignee: Flint Hills Scientific, LLC, Lawrence, KS (US)

( * ) Notice: Subject to any disclaimer, the term of this patent is extended or adjusted under 35 U.S.C. 154(b) by 121 days.

This patent is subject to a terminal disclaimer.

(21) Appl. No.: 16/729,689

(22) Filed: Dec. 30, 2019

(65) Prior Publication Data

US 2020/0129111 A1 Apr. 30, 2020

Related U.S. Application Data

(60) Continuation-in-part of application No. 16/524,702, filed on Jul. 29, 2019, now Pat. No. 11,006,890.

(Continued)

(51) Int. Cl.
| | |
|---|---|
| *A61B 5/00* | (2006.01) |
| *A61B 5/0205* | (2006.01) |
| *A61B 5/08* | (2006.01) |
| *A61B 5/11* | (2006.01) |
| *A61B 5/113* | (2006.01) |
| *A61B 5/318* | (2021.01) |
| *A61B 5/021* | (2006.01) |
| *A61N 1/36* | (2006.01) |

(Continued)

(52) U.S. Cl.
CPC .......... *A61B 5/4094* (2013.01); *A61B 5/0205* (2013.01); *A61B 5/02055* (2013.01); *A61B 5/0816* (2013.01); *A61B 5/113* (2013.01); *A61B 5/1117* (2013.01); *A61B 5/318* (2021.01); *A61B 5/7264* (2013.01); *A61B 5/746* (2013.01); *A61N 1/36064* (2013.01); *A61N 1/36139* (2013.01); *A61B 5/021* (2013.01); *A61B 5/026* (2013.01); *A61B 5/0245* (2013.01); *A61B 5/02405* (2013.01); *A61B 5/0531* (2013.01); *A61B 5/389* (2021.01); *A61B 5/4266* (2013.01); *A61B 5/686* (2013.01); *A61B 7/04* (2013.01); *A61B 8/0883* (2013.01); *A61B 2562/0219* (2013.01); *A61N 1/36135* (2013.01); *A61N 1/36585* (2013.01)

(58) Field of Classification Search
None
See application file for complete search history.

(56) References Cited

U.S. PATENT DOCUMENTS 6,459,804 B2 * 10/2002 Mainguet ............. G06K 9/0002 382/124
6,658,287 B1 * 12/2003 Litt ........................ A61B 5/374 600/544

(Continued)

*Primary Examiner* — Brian T Gedeon
(74) *Attorney, Agent, or Firm* — CP3; Stephen Eisenmann

(57) ABSTRACT

Disclosed are methods and systems for treating epilepsy by stimulating a main trunk of a vagus nerve, or a left vagus nerve, when the patient has had no seizure or a seizure that is not characterized by cardiac changes such as an increase in heart rate, and stimulating a cardiac branch of a vagus nerve, or a right vagus nerve, when the patient has had a seizure characterized by cardiac changes such as a heart rate increase.

19 Claims, 35 Drawing Sheets

Related U.S. Application Data which is a continuation of application No. 15/387,417, filed on Dec. 21, 2016, now Pat. No. 10,405,792, which is a continuation of application No. 14/887,617, filed on Oct. 20, 2015, now Pat. No. 9,545,226, which is a continuation of application No. 14/483,979, filed on Sep. 11, 2014, now Pat. No. 9,186,106, which is a continuation of application No. 13/776,176, filed on Feb. 25, 2013, now Pat. No. 8,852,100, which is a continuation of application No. 13/098,262, filed on Apr. 29, 2011, now Pat. No. 8,382,667, which is a continuation-in-part of application No. 12/896,525, filed on Oct. 1, 2010, now Pat. No. 8,337,404, application No. 16/729,689, which is a continuation-in-part of application No. 16/679,216, filed on Nov. 10, 2019, which is a division of application No. 15/437,155, filed on Feb. 20, 2017, now Pat. No. 10,682,515, which is a continuation-in-part of application No. 14/050,173, filed on Oct. 9, 2013, now Pat. No. 9,579,506, which is a continuation-in-part of application No. 13/601,099, filed on Aug. 31, 2012, now Pat. No. 9,314,633, which is a continuation-in-part of application No. 12/020,195, filed on Jan. 25, 2008, now Pat. No. 8,260,426, which is a continuation-in-part of application No. 12/020,097, filed on Jan. 25, 2008, now Pat. No. 8,565,867.

(51) Int. Cl.

| | | |
|---|---|---|
| *A61B 5/026* | (2006.01) | |
| *A61B 5/0245* | (2006.01) | |
| *A61N 1/365* | (2006.01) | |
| *A61B 5/024* | (2006.01) | |
| *A61B 5/0531* | (2021.01) | |
| *A61B 7/04* | (2006.01) | |
| *A61B 8/08* | (2006.01) | |
| *A61B 5/389* | (2021.01) | |

(56) References Cited

U.S. PATENT DOCUMENTS

| | | | |
|---|---|---|---|
| 7,502,643 B2* | 3/2009 | Farringdon | A61B 5/721 600/509 |
| 7,515,054 B2* | 4/2009 | Torch | A61B 3/112 340/573.1 |
| 8,016,776 B2* | 9/2011 | Bourget | A61B 5/4815 600/587 |
| 8,140,143 B2* | 3/2012 | Picard | A61B 5/0022 600/388 |
| 8,157,730 B2* | 4/2012 | LeBoeuf | G06Q 30/0251 600/300 |
| 8,157,731 B2* | 4/2012 | Teller | A61B 5/1118 |
| 8,403,881 B2* | 3/2013 | Ferren | A61B 5/0205 604/65 |
| 8,641,646 B2* | 2/2014 | Colborn | A61N 1/36139 600/595 |
| 2006/0252999 A1* | 11/2006 | Devaul | A61B 5/411 600/300 |
| 2010/0010585 A1* | 1/2010 | Davis | G16H 40/63 607/62 |

\* cited by examiner

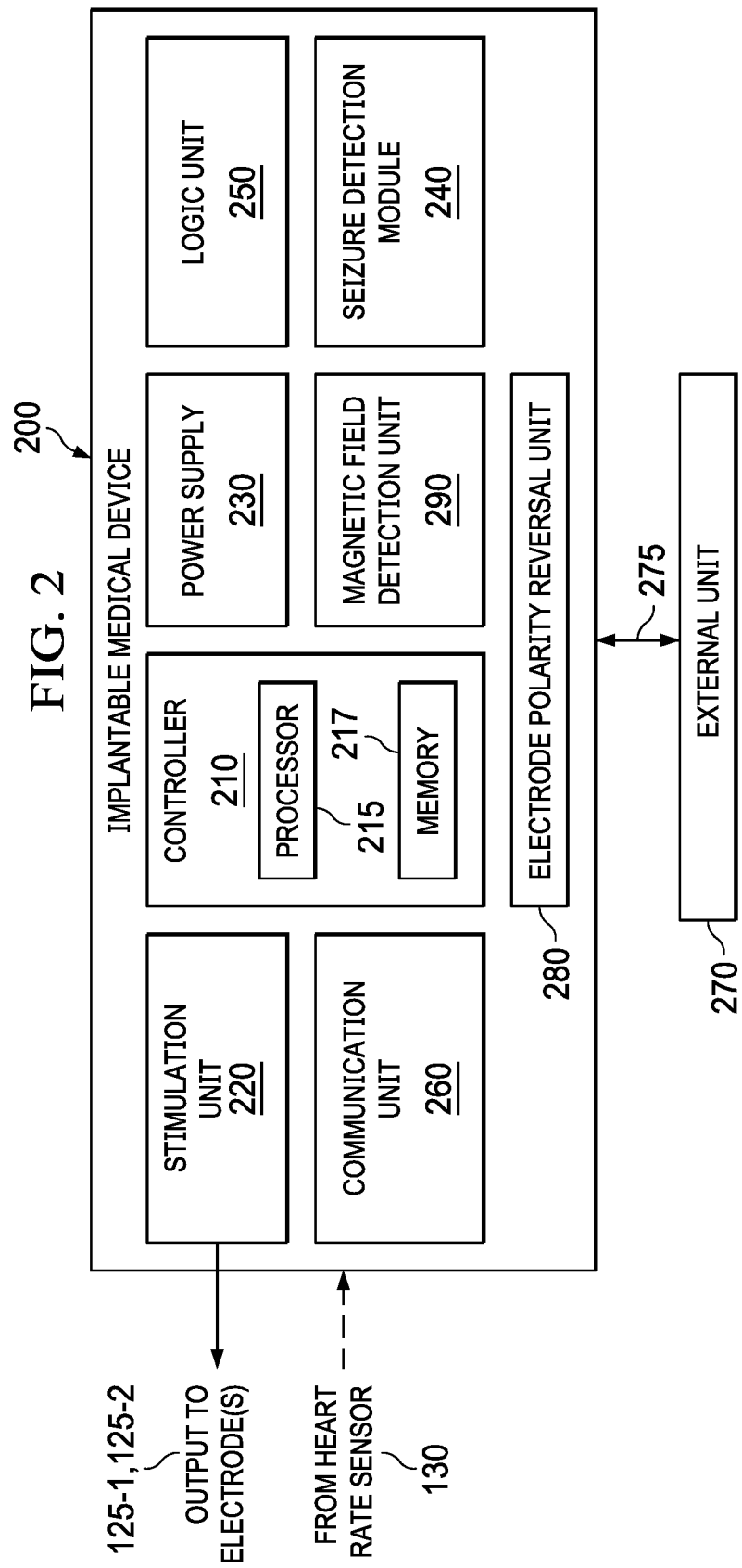

NOT TO SCALE

NOT TO SCALE

NOT TO SCALE

NOT TO SCALE

CONTINGENT CARDIO-PROTECTION FOR EPILEPSY PATIENTS

CROSS-REFERENCE TO RELATED APPLICATIONS

This presently being filed application is a continuation-in-part of and claims priority to U.S. patent application Ser. No. 16/524,702 entitled "Detecting, Quantifying, and/or Classifying Seizures Using MultiModal Data", filed on Jul. 29, 2019, which is a continuation of and claims priority to U.S. patent application Ser. No. 15/387,417 entitled "Detecting, Quantifying, and/or Classifying Seizures Using MultiModal Data", filed on Dec. 21, 2016 (Now U.S. Pat. No. 10,405,792) which is a continuation of and claims priority to U.S. patent application Ser. No. 14/887,617 entitled "Detecting, Quantifying, and/or Classifying Seizures Using MultiModal Data", filed on Oct. 20, 2015 (Now U.S. Pat. No. 9,545,226) which is a continuation of and claims priority to U.S. patent application Ser. No. 14/483,979 entitled "Detecting, Quantifying, and/or Classifying Seizures Using MultiModal Data", filed on Sep. 11, 2014 (Now U.S. Pat. No. 9,186,106) which is a continuation of and claims priority to U.S. patent application Ser. No. 13/776,176 entitled "Detecting, Quantifying, and/or Classifying Seizures Using MultiModal Data", filed on Feb. 25, 2013 (Now U.S. Pat. No. 8,852,100) which is a continuation of and claims priority to U.S. patent application Ser. No. 13/098,262 entitled "Detecting, Quantifying, and/or Classifying Seizures Using MultiModal Data", filed on Apr. 29, 2011 (Now U.S. Pat. No. 8,382,667) where U.S. patent application Ser. No. 13/098,262 is a continuation-in-part of and claims priority to U.S. patent application Ser. No. 12/896,525 "Detecting, Quantifying, and/or Classifying Seizures Using MultiModal Data", filed on Oct. 1, 2010 (Now U.S. Pat. No. 8,337,404) and this presently being filed application is a continuation-in-part of and claims priority to U.S. patent application Ser. No. 16/679,216, entitled "Contingent Cardio-Protection For Epilepsy Patients", filed on Nov. 10, 2019 which is a continuation-in-part of and claims priority to U.S. patent application Ser. No. 15/437,155 entitled "Contingent Cardio-Protection For Epilepsy Patients", filed on Feb. 20, 2017, which claims priority to and is a divisional application of U.S. patent application Ser. No. 14/050,173 entitled "Contingent Cardio-Protection For Epilepsy Patients", filed on Oct. 9, 2013 (now U.S. Pat. No. 9,579,506), which claims priority to and is a continuation-in-part of U.S. patent application Ser. No. 13/601,099 entitled "Contingent Cardio-Protection For Epilepsy Patients", filed on Aug. 31, 2012 (now U.S. Pat. No. 9,314,633), which claims priority to and is a continuation-in-part of U.S. patent application Ser. No. 12/020,195 entitled "Method, Apparatus and System for Bipolar Charge Utilization during Stimulation by an Implantable Medical Device", filed on Jan. 25, 2008 (now U.S. Pat. No. 8,260,426) and claims priority to and is a continuation-in-part of U.S. patent application Ser. No. 12/020,097 entitled "Changeable Electrode Polarity Stimulation by an Implantable Medical Device", filed on Jan. 25, 2008 (now U.S. Pat. No. 8,565,867) all of which are incorporated herein by reference in their entireties.

BACKGROUND OF THE DISCLOSURE

This disclosure relates generally to medical devices, and, more particularly, to methods, apparatus, and systems for performing vagus nerve stimulation (VNS) for treating epileptic seizures characterized by cardiac changes, including ictal tachycardia.

DESCRIPTION OF THE RELATED ART

While seizures are the best known and most studied manifestation of epilepsy, cardiac alterations are prevalent and may account for the high rate of sudden unexpected death (SUDEP) in these patients. These alterations may include changes in rate (most commonly tachycardia, rarely bradycardia or asystole), rhythm (PACs, PVCs,), conduction (e.g., bundle branch block) and repolarization abnormalities (e.g., Q-T prolongation, which occurs primarily during (ictal) but also between seizures (inter-ictally). In addition, S-T segment depression (a sign of myocardial ischemia) is observed during epileptic seizures. Significant elevations in heart-type fatty acid binding protein (H-FABP), a cytoplasmic low-molecular weight protein released into the circulation during myocardial injury have been documented in patients with epilepsy and without evidence of coronary artery disease, not only during seizures but also during free-seizure periods. H-FABP is a more sensitive and specific marker of myocardial ischemia than troponin I or CK-MB. Elevations in H-FABP appear to be un-correlated with duration of illness, of the recorded seizures, or with the Chalfont severity score of the patients.

The cardiac alterations in epilepsy patients, both during and between seizures, have a multi-factorial etiology, but a vago-sympathetic imbalance seems to play a prominent role in their generation. The majority of epileptic seizures enhance the sympathetic tone (plasma noradrenaline and adrenaline rise markedly after seizure onset) causing tachycardia, arterial hypertension and increases in the respiratory rate, among others. Recurrent and frequent exposure to the outpouring of catecholamines associated with seizures in patients with pharmaco-resistant epilepsies may, for example, account for abnormalities that increase the risk of sudden death such as prolongation of the Q-T interval which leads to often fatal tachyarrhythmias such as torsade de pointe. Further evidence in support of the role of catecholamines in SUDEP is found in autopsies of SUDEP victims, revealing interstitial myocardial fibrosis (a risk factor for lethal arrhythmias), myocyte vacuolization, atrophy of cardiomyocytes, leukocytic infiltration, and perivascular fibrosis. Restoration of the sympathetic-parasympathetic tone to normal levels, a therapeutic objective that may be accomplished by enhancing parasympathetic activity through among others, electrical stimulation of the vagus nerve, may decrease the rate and severity of cardiac and autonomic co-morbidities in these patients.

While there have been significant advances over the last several decades in treatments for epileptic seizures, the management of co-morbidities—in particular the cardiac alterations associated with seizures—remains largely unaddressed. There is a need for improved epilepsy treatments that address cardiac impairments associated with seizures. Pharmacological therapies for neurological diseases (including epilepsy) have been available for many decades. A more recent treatment for neurological disorders involves electrical stimulation of a target tissue to reduce symptoms or effects of the disorder. Such therapeutic electrical signals have been successfully applied to brain, spinal cord, and cranial nerves tissues improve or ameliorate a variety of conditions. A particular example of such a therapy involves applying an electrical signal to the vagus nerve to reduce or eliminate epileptic seizures, as described in U.S. Pat. Nos.

4,702,254, 4,867,164, and 5,025,807, which are hereby incorporated herein by reference in their entirety.

The endogenous electrical activity (i.e., activity attributable to the natural functioning of the patient's own body) of a neural structure may be modulated in a variety of ways. One such way is by applying exogenous (i.e., from a source other than the patient's own body) electrical, chemical, or mechanical signals to the neural structure. In some embodiments, the exogenous signal ("neurostimulation" or "neuromodulation") may involve the induction of afferent action potentials, efferent action potentials, or both, in the neural structure. In some embodiments, the exogenous (therapeutic) signal may block or interrupt the transmission of endogenous (natural) electrical activity in the target neural structure. Electrical signal therapy may be provided by implanting an electrical device underneath the skin of a patient and delivering an electrical signal to a nerve such as a cranial nerve.

In one embodiment, the electrical signal therapy may involve detecting a symptom or event associated with the patient's medical condition, and the electrical signal may be delivered in response to the detection. This type of stimulation is generally referred to as "closed-loop," "active," "feedback," "contingent" or "triggered" stimulation. Alternatively, the system may operate according to a predetermined program to periodically apply a series of electrical pulses to the nerve intermittently throughout the day, or over another predetermined time interval. This type of stimulation is generally referred to as "open-loop," "passive," "non-feedback," "non-contingent" or "prophylactic," stimulation.

In other embodiments, both open- and closed-loop stimulation modes may be used. For example, an open-loop electrical signal may operate as a "default" program that is repeated according to a programmed on-time and off-time until a condition is detected by one or more body sensors and/or algorithms. The open-loop electrical signal may then be interrupted in response to the detection, and the closed-loop electrical signal may be applied—either for a predetermined time or until the detected condition has been effectively treated. The closed-loop signal may then be interrupted, and the open-loop program may be resumed. Therapeutic electrical stimulation may be applied by an implantable medical device (IMD) within the patient's body or, in some embodiments, externally.

Closed-loop stimulation of the vagus nerve has been proposed to treat epileptic seizures. Many patients with intractable, refractory seizures experience changes in heart rate and/or other autonomic body signals near the clinical onset of seizures. In some instances the changes may occur prior to the clinical onset, and in other cases the changes may occur at or after the clinical onset. Where the changes involves heart rate, most often the rate increases, although in some instances a drop or a biphasic change (up-then-down or down-then-up) may occur. It is possible using a heart rate sensor to detect such changes and to initiate therapeutic electrical stimulation (e.g., VNS) based on the detected change. The closed-loop therapy may be a modified version of an open-loop therapy. See, e.g., U.S. Pat. Nos. 5,928,272, and 6,341,236, each hereby incorporated by reference herein. The detected change may also be used to warn a patient or third party of an impending or occurring seizure.

VNS therapy for epilepsy patients typically involves a train of electrical pulses applied to the nerve with an electrode pair including a cathode and an anode located on a left or right main vagal trunk in the neck (cervical) area. Only the cathode is capable of generating action potentials in nerve fibers within the vagus nerve; the anode may block some or all of the action potentials that reach it (whether endogenous or exogenously generated by the cathode). VNS as an epilepsy therapy involves modulation of one or more brain structures. Therefore, to prevent the anode from blocking action potentials generated by the cathode from reaching the brain, the cathode is usually located proximal to the brain relative to the anode. For vagal stimulation in the neck area, the cathode is thus usually the upper electrode and the anode is the lower electrode. This arrangement is believed to result in partial blockage of action potentials distal to or below the anode (i.e., those that would travel through the vagus nerve branches innervating the lungs, heart and other viscerae). Using an upper-cathode/lower-anode arrangement has also been favored to minimize any effect of the vagus nerve stimulation on the heart.

Stimulation of the left vagus nerve, for treatment of epilepsy has complex effects on heart rate (see Frei & Osorio, Epilepsia 2001), one of which includes slowing of the heart rate, while stimulation of the right vagus nerve has a more prominent bradycardic effect. Electrical stimulation of the right vagus nerve has been proposed for use in the operating room to slow the heart during heart bypass surgery, to provide a surgeon with a longer time period to place sutures between heartbeats (see, e.g., U.S. Pat. No. 5,651, 373). Some patents discussing VNS therapy for epilepsy treatment express concern with the risk of inadvertently slowing the heart during stimulation. In U.S. Pat. No. 4,702,254, it is suggested that by locating the VNS stimulation electrodes below the inferior cardiac nerve, "minimal slowing of the heart rate is achieved" (col. 7 lines 3-5), and in U.S. Pat. No. 6,920,357, the use of a pacemaker to avoid inadvertent slowing of the heart is disclosed.

Cranial nerve stimulation has also been suggested for disorders outside the brain such as those affecting the gastrointestinal system, the pancreas (e.g., diabetes, which often features impaired production of insulin by the islets of Langerhans in the pancreas), or the kidneys. Electrical signal stimulation of either the brain alone or the organ alone may have some efficacy in treating such medical conditions, but may lack maximal efficacy.

While electrical stimulation has been used for many years to treat a number of conditions, a need exists for improved VNS methods of treating epilepsy and its cardiac co-morbidities as well as other brain and non-brain disorders.

SUMMARY OF THE DISCLOSURE

In one aspect, the present disclosure relates to a method of treating a patient having epilepsy comprising receiving at least one body data stream, analyzing the at least one body data stream using a seizure or event detection algorithm to detect whether or not the patient is having and/or has had an epileptic seizure, receiving a cardiac signal of the patient, applying a first electrical signal to a vagus nerve of the patient based on a determination that the patient is not having and/or has not had an epileptic seizure characterized by a decrease in the patient's heart rate, wherein the first electrical signal is not a vagus nerve conduction blocking electrical signal, and applying a second electrical signal to a vagus nerve of the patient based on a determination that the patient is having and/or has had an epileptic seizure characterized by a decrease in the patient's heart rate, wherein the second electrical signal is a pulsed electrical signal that blocks action potential conduction in the vagus nerve.

In one aspect, the present disclosure relates to a method of treating a patient having epilepsy comprising sensing a cardiac signal and a kinetic signal of the patient, analyzing at least one of the cardiac signal and the kinetic signal; determining whether or not the patient has had an epileptic seizure based on the analyzing; in response to a determination that the patient has had an epileptic seizure, determining whether or not the seizure is characterized by a decrease in the patient's heart rate, applying a first electrical signal to a vagus nerve of the patient based on a determination that the patient has had an epileptic seizure characterized by a decrease in the patient's heart rate, wherein the first electrical signal is a pulsed electrical signal that blocks action potential conduction in the vagus nerve; and applying a second electrical signal to a vagus nerve of the patient based on one of a) a determination that the patient has not had an epileptic seizure, and b) a determination that the patient has had an epileptic seizure that is not characterized by a decrease in the patient's heart rate, wherein the second electrical signal is not a vagus nerve conduction blocking electrical signal.

In one aspect, the present disclosure relates to a system for treating a medical condition in a patient, comprising at least one electrode coupled to a vagus nerve of the patient, a programmable electrical signal generator, a sensor for sensing at least one body data stream, a seizure detection module capable of analyzing the at least one body data stream and determining, based on the analyzing, whether or not the patient is having and/or has had an epileptic seizure, a heart rate determination unit capable of determining a heart rate of a patient proximate in time to an epileptic seizure detected by the seizure detection module, and a logic unit for applying a first electrical signal to the vagus nerve using the at least one electrode based on a determination by the seizure detection module that the patient is having and/or has had an epileptic seizure characterized by a decrease in the patient's heart rate, wherein the first electrical signal is a pulsed electrical signal that blocks action potential conduction in the vagus nerve, and for applying a second electrical signal to the vagus nerve using the at least one electrode as a cathode based upon one of a) a determination that the patient is not having and/or has not had an epileptic seizure, and b) a determination that the patient is having and/or has had an epileptic seizure that is not characterized by a decrease in the patient's heart rate, wherein the second electrical signal is not a vagus nerve conduction blocking electrical signal. In one embodiment, the seizure detection module may comprise the heart rate determination unit.

In one aspect, the present disclosure relates to a method of treating a patient having epilepsy comprising applying a first electrical signal to a vagus nerve of the patient, wherein the first electrical signal is an open-loop electrical signal having a programmed on-time and a programmed off-time, sensing at least one body signal of the patient, determining the start of an epileptic seizure based on the at least one body signal, determining whether or not the seizure is characterized by a decrease in the patient's heart rate, applying a second, closed-loop electrical signal to a vagus nerve of the patient based on a determination that the epileptic seizure is not characterized by a decrease in the patient's heart rate, and applying a third, closed-loop electrical signal to a vagus nerve of the patient based on a determination that the seizure is characterized by a decrease in the patient's heart rate, wherein the third electrical signal is applied to block action potential conduction on the vagus nerve.

In one aspect, the present disclosure relates to a method of controlling a heart rate of an epilepsy patient comprising sensing a kinetic signal of the patient; analyzing said kinetic signal to determine at least one kinetic index; receiving a cardiac signal of the patient; analyzing the cardiac signal to determine the patient's heart rate; determining if the patient's heart rate is commensurate with the at least one kinetic index; and applying a first electrical signal to a vagus nerve of the patient based on a determination that the patient's heart rate is not commensurate with the kinetic index. In one embodiment, the at least one kinetic index comprises at least one of an activity level or an activity type of the patient, and determining if the heart rate is commensurate with the kinetic index comprises determining if the heart rate is commensurate with the at least one of an activity level or an activity type.

In one aspect, the present disclosure relates to a method of controlling a heart rate of an epilepsy patient comprising sensing at least one of a kinetic signal and a metabolic (e.g., oxygen consumption) signal of the patient; receiving a cardiac signal of the patient; analyzing the cardiac signal to determine the patient's heart rate; determining if the patient's heart rate is commensurate with the at least one of a kinetic and a metabolic signal of the patient; and applying a first electrical signal to a vagus nerve of the patient based on a determination that the patient's heart rate is not commensurate with the at least one of a kinetic signal and a metabolic signal. In one embodiment, the method further comprises determining at least one of an activity level or an activity type of the patient based on the at least one of a kinetic and a metabolic signal, and determining if the heart rate is commensurate with the kinetic signal comprises determining if the heart rate is commensurate with the at least one of an activity level or an activity type.

In one aspect, the present disclosure relates to a method of treating a patient having epilepsy comprising sensing at least one body signal of the patient; determining whether or not the patient is having or has had an epileptic seizure based on the at least one body signal; sensing a cardiac signal of the patient; determining whether or not the seizure is associated with a change in the patient's cardiac signal; applying a first therapy to a vagus nerve of the patient based on a determination that the patient is having or has had an epileptic seizure that is not associated with a change in the patient's cardiac signal, wherein the first therapy is selected from an electrical, chemical, mechanical (e.g., pressure) or thermal signal. The method further comprises applying a second therapy to a vagus nerve of the patient based on a determination that the patient has had an epileptic seizure associated with a change in the patient's cardiac signal, wherein the second therapy is selected from an electrical, chemical, mechanical (e.g., pressure) or thermal signal. In some embodiments, a third therapy may be applied to a vagus nerve based a determination that the patient has not had an epileptic seizure, wherein the third therapy is selected form an electrical, chemical, mechanical or thermal signal.

This disclosure relates to medical device systems and methods capable of detecting and, in some embodiments, treating an occurring or impending seizure using multimodal body data.

Of the approximately 60 million people worldwide affected with epilepsy, roughly 23 million people suffer from epilepsy resistant to multiple medications. In the USA alone, the annual cost of epilepsy care is USD 12 billion (in 1995 dollars), most of which is attributable to subjects with pharmaco-resistant seizures. Pharmaco-resistant seizures are associated with an increase mortality and morbidity (e.g., compared to the general population and to epileptics whose seizures are controlled by medications) and with markedly degraded quality of life for patients. Seizures may impair motor control, responsiveness to a wide class of stimuli, and other cognitive functions. The sudden onset of a patient's impairment of motor control, responsiveness, and other cognitive functions precludes the performance of necessary and even simple daily life tasks such as driving a vehicle, cooking, or operating machinery, as well as more complex tasks such as acquiring knowledge and socializing.

Therapies using electrical currents or fields to provide a therapy to a patient (electrotherapy) are beneficial for certain neurological disorders, such as epilepsy. Implantable medical devices have been effectively used to deliver therapeutic electrical stimulation to various portions of the human body (e.g., the vagus nerve) for treating epilepsy. As used herein, "stimulation," "neurostimulation," "stimulation signal," "therapeutic signal," or "neurostimulation signal" refers to the direct or indirect application of an electrical, mechanical, magnetic, electro-magnetic, photonic, acoustic, cognitive, and/or chemical signal to an organ or a neural structure in the patient's body. The signal is an exogenous signal that is distinct from the endogenous electro-chemical activity inherent to the patient's body and also from that found in the environment. In other words, the stimulation signal (whether electrical, mechanical, magnetic, electro-magnetic, photonic, acoustic, cognitive, and/or chemical in nature) applied to a cranial nerve or to other nervous tissue structure in the present disclosure is a signal applied from a medical device, e.g., a neurostimulator.

A "therapeutic signal" refers to a stimulation signal delivered to a patient's body with the intent of treating a medical condition through a suppressing (e.g., blocking) or modulating effect to neural tissue. The effect of a stimulation signal on neuronal activity may be suppressing or modulating; however, for simplicity, the terms "stimulating", suppressing, and modulating, and variants thereof, are sometimes used interchangeably herein. In general, however, the delivery of an exogenous signal itself refers to "stimulation" of an organ or a neural structure, while the effects of that signal, if any, on the electrical activity of the neural structure are properly referred to as suppression or modulation.

Depending upon myriad factors such as the history (recent and distant) of a patient's brain activity (e.g., electro-chemical, mental, emotional), stimulation parameters and time of day, to name a few, the effects of stimulation upon the neural tissue may be excitatory or inhibitory, facilitatory or disfacilitatory and may suppress, enhance, or leave unaltered neuronal activity. For example, the suppressing effect of a stimulation signal on neural tissue would manifest as the blockage of abnormal activity (e.g., epileptic seizures) see Osorio et al., Ann Neurol 2005; Osorio & Frei IJNS 2009) The mechanisms thorough which this suppressing effect takes place are described in the foregoing articles. Suppression of abnormal neural activity is generally a threshold or suprathreshold process and the temporal scale over which it occurs is usually in the order of tens or hundreds of milliseconds. Modulation of abnormal or undesirable neural activity is typically a "sub-threshold" process in the spatio-temporal domain that may summate and result under certain conditions, in threshold or suprathreshold neural events. The temporal scale of modulation is usually longer than that of suppression, encompassing seconds to hours, even months. In addition to inhibition or dysfacilitation, modification of neural activity (e.g., wave annihilation) may be exerted through collision with identical, similar or dissimilar waves, a concept borrowed from wave mechanics, or through phase resetting (Winfree).

In some cases, electrotherapy may be provided by implanting an electrical device, e.g., an implantable medical device (IMD), inside a patient's body for stimulation of a nervous tissue, such as a cranial nerve. Generally, electrotherapy signals that suppress or modulate neural activity are delivered by the IMD via one or more leads. When applicable, the leads generally terminate at their distal ends in one or more electrodes, and the electrodes, in turn, are coupled to a target tissue in the patient's body. For example, a number of electrodes may be attached to various points of a nerve or other tissue inside a human body for delivery of a neurostimulation signal.

While contingent (also referred to as "closed-loop," "active," or "feedback" stimulation; i.e., electrotherapy applied in response to sensed information, such as heart rate) stimulation schemes have been proposed, non-contingent, programmed periodic stimulation is the prevailing modality. For example, vagus nerve stimulation for the treatment of epilepsy usually involves a series of grouped electrical pulses defined by an "on-time" (such as 30 sec.) and an "off-time" (such as 5 min.). This type of stimulation is also referred to as "open-loop," "passive," or "non-feedback" stimulation. Each sequence of pulses during an on-time may be referred to as a "pulse burst." The burst is followed by the off-time period in which no signals are applied to the nerve. During the on-time, electrical pulses of a defined electrical current (e.g., 0.5-3.5 milliamps) and pulse width (e.g., 0.25-1.0 milliseconds) are delivered at a defined frequency (e.g., 20-30 Hz) for a certain duration (e.g., 10-60 seconds). The on-time and off-time parameters together define a duty cycle, which is the ratio of the on-time to the sum of the on-time and off-time, and which describes the fraction of time that the electrical signal is applied to the nerve.

In VNS, the on-time and off-time may be programmed to define an intermittent pattern in which a repeating series of electrical pulse bursts are generated and applied to a cranial nerve such as the vagus nerve. The off-time is provided to minimize adverse effects and conserve power. If the off-time is set at zero, the electrical signal in conventional VNS may provide continuous stimulation to the vagus nerve. Alternatively, the off time may be as long as one day or more, in which case the pulse bursts are provided only once per day or at even longer intervals. Typically, however, the ratio of "off-time" to "on-time" may range from about 0.5 to about 10.

In addition to the on-time and off-time, the other parameters defining the electrical signal in VNS may be programmed over a range of values. The pulse width for the pulses in a pulse burst of conventional VNS may be set to a value not greater than about 1 msec, such as about 250-500 μsec, and the number of pulses in a pulse burst is typically set by programming a frequency in a range of about 20-300 Hz (i.e., 20 pulses per second to 300 pulses per second). A non-uniform frequency may also be used. Frequency may be altered during a pulse burst by either a frequency sweep from a low frequency to a high frequency, or vice versa. Alternatively, the timing between adjacent individual signals within a burst may be randomly changed such that two adjacent signals may be generated at any frequency within a range of frequencies.

Although neurostimulation has proven effective in the treatment of a number of medical conditions, it would be desirable to further enhance and optimize neurostimulation-based therapy for this purpose. For example, it may be desirable to detect an occurring or impending seizure. Such detection may be useful in triggering a therapy, monitoring the course of a patient's disease, or the progress of his or her treatment thereof. Alternatively or in addition, such detection may be useful in issuing a warning of an impending or on-going seizure. Such a warning may, for example, minimize the risk of injury or death. Said warning may be perceived by the patient, a physician, a caregiver, or a suitably programmed computer and allow that person or computer program to take action intended to reduce the likelihood, duration, or severity of the seizure or impending seizure, or to facilitate further medical treatment or intervention for the patient. In particular, detection of an occurring or impending seizure enables the use of contingent neurostimulation. The state of the art does not provide an efficient and effective means for performing such detection and/or warning. Conventional VNS stimulation as described above does not detect occurring or impending seizures.

Closed-loop neurostimulation therapies for treating epilepsy have been proposed in which stimulation is triggered based upon factors including EEG activity (see, e.g., U.S. Pat. Nos. 5,995,868 and 7,280,867) as well as cardiac-based activity (see., e.g., U.S. Pat. Nos. 6,961,618 and 5,928,272). EEG- or ECoG-based approaches involving recording of neural electrical activity at any spatio-temporal scale involve determination of one or more parameters from brain electrical activity that indicate a seizure. Such approaches have met with limited success and have a number of drawbacks, including highly invasive and technically demanding and costly surgery for implanted systems. Approaches that do not invade the brain have marked limitations due mainly to the extremely low/unreliable S/N, and poor patient compliance with, e.g., the patient wearing electrodes on the scalp for extended periods.

In one embodiment, the present disclosure provides a method. In one embodiment, the method comprises receiving at least one of signal relating to a first cardiac activity from a patient and a signal relating to a first body movement from the patient; deriving at least one patient index from said at least one received signal; triggering at least one of a test of the patient's responsiveness, a test of the patient's awareness, a test of a second cardiac activity of the patient, a test of a second body movement of the patient, a spectral analysis test of a second cardiac activity of the patient, and a spectral analysis test of the second body movement of the patient, based on said at least one patient index; determining an occurrence of an epileptic event based at least in part on the one or more triggered tests; and performing a further action in response to the determination of the occurrence of the epileptic event.

In one embodiment, the present disclosure provides a method. In one embodiment, the method comprises receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and a spectral analysis signal relating to the second body movement; determining an occurrence of a generalized tonic-clonic epileptic seizure, the determination being based upon the correlation of at least two features, at least one feature being of each of the at least two body signals, wherein: the feature of the first cardiac activity signal is an increase in the patient's heart rate above an interictal reference value; the feature of the first body movement signal is at least one of (i) an increase in axial or limb muscle tone substantially above an interictal or exercise value for the patient, (ii) a decrease in axial muscle tone in a non-recumbent patient, below the value associated with a first, non-recumbent position, (iii) fall followed by an increase in body muscle tone, or (iv) a fall followed by generalized body movements; the feature of the responsiveness signal is a decrease in the patient's responsiveness below an interictal reference value; the feature of the awareness signal is a decrease in the patient's awareness below an interictal reference value; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and performing a further action in response to the determination of the occurrence of the epileptic event.

In one embodiment, the present disclosure provides a method. In one embodiment, the method comprises receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and spectral analysis signal relating to the second body movement; and determining an occurrence of a partial epileptic seizure based upon a correlation of two features, at least one feature being of each of the at least two body signals, wherein: the feature of the first cardiac signal is a value outside an interictal reference value range; the feature of the first body movement signal is a body movement associated with a partial seizure; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and performing a further action in response to the determination of the occurrence of the epileptic event.

In other embodiments, a computer readable program storage device is provided that is encoded with instructions that, when executed by a computer, perform a method described above.

In one embodiment, a medical device is provided comprising an autonomic signal module, a kinetic signal module, a detection module, and a processor adapted to perform a method as described above.

INCORPORATION BY REFERENCE

The following United States patents or patent applications are incorporated by reference:

U.S. patent application Ser. No. 12/756,065, filed Apr. 7, 2010.

U.S. patent application Ser. No. 12/770,562, filed Apr. 29, 2010.

U.S. patent application Ser. No. 12/884,051, filed Sep. 16, 2010.

U.S. patent application Ser. No. 12/896,525, filed Oct. 1, 2010.

U.S. patent application Ser. No. 13/040,996, filed Mar. 4, 2011.

BRIEF DESCRIPTION OF THE DRAWINGS

The disclosure may be understood by reference to the following description taken in conjunction with the accompanying drawings, in which like reference numerals identify like elements, and in which:

FIG. 2 illustrates a block diagram depiction of an implantable medical device of FIG. 1, in accordance with one illustrative embodiment of the present disclosure;

FIG. 22A shows an external device in communication with a sensor. FIG. 22B shows an implanted device providing a therapeutic signal to a structure of the patient's body, each in accordance with one illustrative embodiment of the present disclosure;

Figure 1A:
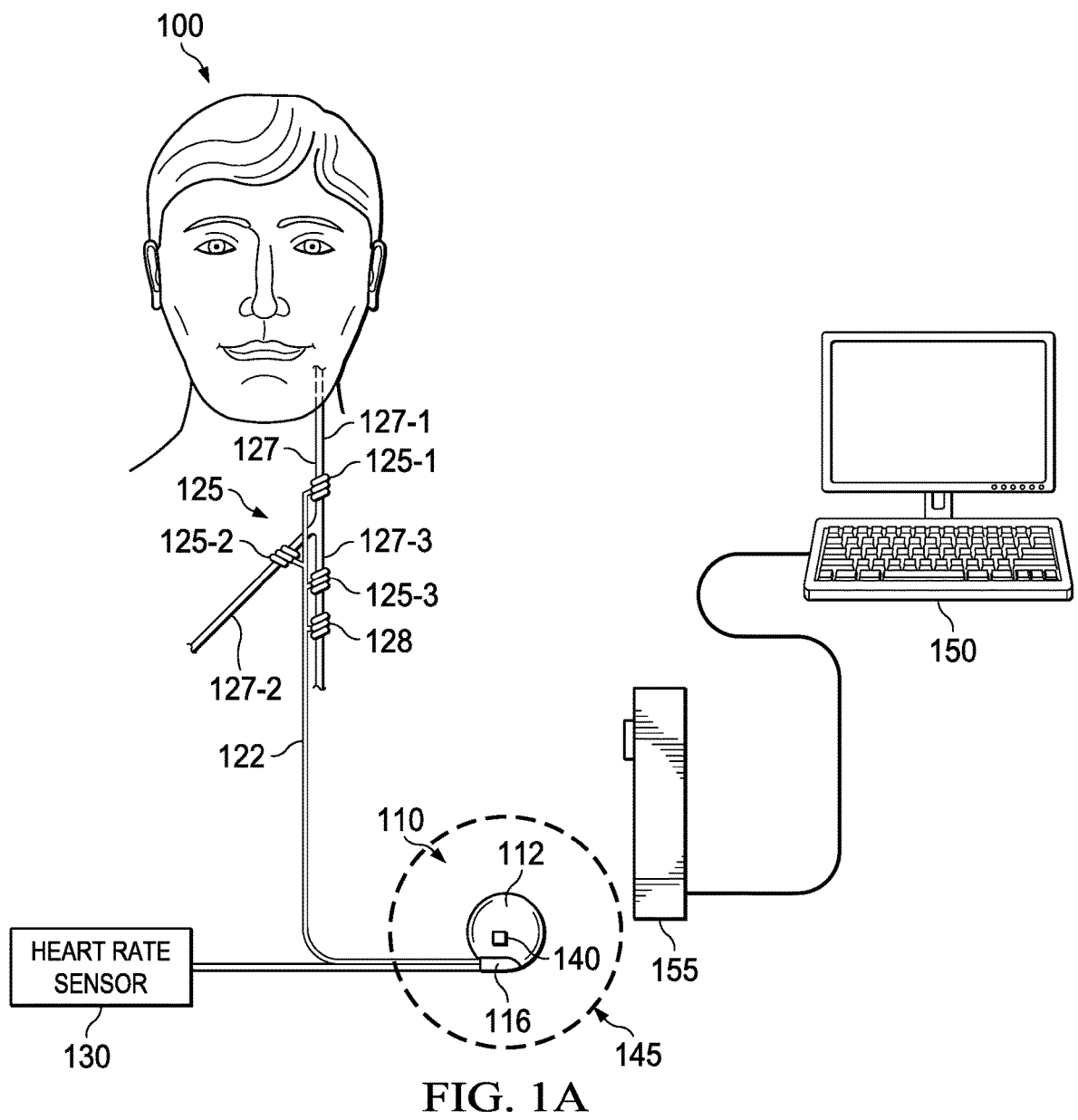
FIGS. 1A-1E provide stylized diagrams of an implantable medical device implanted into a patient's body for providing first and second electrical signals to a vagus nerve of a patient for treating epileptic seizures, in accordance with one illustrative embodiment of the present disclosure.

While the disclosure is susceptible to various modifications and alternative forms, specific embodiments thereof have been shown by way of example in the drawings and are herein described in detail. It should be understood, however, that the description herein of specific embodiments is not intended to limit the disclosure to the particular forms disclosed, but on the contrary, the intention is to cover all modifications, equivalents, and alternatives falling within the spirit and scope of the disclosure as defined by the appended claims.

DETAILED DESCRIPTION OF SPECIFIC EMBODIMENTS

Illustrative embodiments of the disclosure are described herein. For clarity, not all features of an actual implementation are provided in detail. In any actual embodiment, numerous implementation-specific decisions must be made to achieve the design-specific goals. Such a development effort, while possibly complex and time-consuming, would nevertheless be a routine task for persons of skill in the art given this disclosure.

This application does not intend to distinguish between components that differ in name but not function. "Including" and "includes" are used in an open-ended fashion, and should be interpreted to mean "including, but not limited to." "Couple" or "couples" are intended to mean either a direct or an indirect electrical connection. "Direct contact," "direct attachment," or providing a "direct coupling" indicates that a surface of a first element contacts the surface of a second element with no substantial attenuating medium there between. Small quantities of substances, such as bodily fluids, that do not substantially attenuate electrical connections do not vitiate direct contact. "Or" is used in the inclusive sense (i.e., "and/or") unless a specific use to the contrary is explicitly stated.

"Electrode" or "electrodes" may refer to one or more stimulation electrodes (i.e., electrodes for applying an electrical signal generated by an IMD to a tissue), sensing electrodes (i.e., electrodes for sensing a body signal), and/or electrodes capable of either stimulation or sensing. "Cathode" and "anode" have their standard meanings, as the electrode at which current leaves the IMD system and the electrode at which current enters the IMD system, respectively. Reversing the polarity of the electrodes can be effected by any switching technique known in the art.

A "pulse" is used herein to refer to a single application of electrical charge from the cathode to target neural tissue. A pulse may include both a therapeutic portion (in which most or all of the therapeutic or action-potential-generating effect occurs) and a charge-balancing portion in which the polarity of the electrodes are reversed and the electrical current is allowed to flow in the opposite direction to avoid electrode and/or tissue damage. Individual pulses are separated by a time period in which no charge is delivered to the nerve, which can be called the "interpulse interval." A "burst" is used herein to refer to a plurality of pulses, which may be separated from other bursts by an interburst interval in which no charge is delivered to the nerve. The interburst intervals have a duration exceeding the interpulse interval duration. In one embodiment, the interburst interval is at least twice as long as the interpulse interval. The time period between the end of the last pulse of a first burst and the initiation of the first pulse of the next subsequent burst can be called the "interburst interval." In one embodiment, the interburst interval is at least 100 msec.

A plurality of pulses can refer to any of (a) a number of consecutive pulses within a burst, (b) all the pulses of a burst, or (c) a number of consecutive pulses including the final pulse of a first burst and the first pulse of the next subsequent burst.

"Stimulate," "stimulating" and "stimulator" may generally refer to applying a signal, stimulus, or impulse to neural tissue (e.g., a volume of neural tissue in the brain or a nerve) for affecting it neuronal activity. While the effect of such stimulation on neuronal activity is termed "modulation," for simplicity, the terms "stimulating" and "modulating", and variants thereof, are sometimes used interchangeably herein. The modulation effect of a stimulation signal on neural tissue may be excitatory or inhibitory, and may potentiate acute and/or long-term changes in neuronal activity. For example, the modulation effect of a stimulation signal may comprise: (a) initiating action potentials in the target neural tissue; (b) inhibition of conduction of action potentials (whether endogenous or exogenously generated, or blocking their conduction (e.g., by hyperpolarizing or collision blocking), (c) changes in neurotransmitter/neuromodulator release or uptake, and (d) changes in neuroplasticity or neurogenesis of brain tissue. Applying an electrical signal to an autonomic nerve may comprise generating a response that includes an afferent action potential, an efferent action potential, an afferent hyperpolarization, an efferent hyperpolarization, an afferent sub-threshold depolarization, and/or an efferent sub-threshold depolarization. The terms tachycardia and bradycardia are used here in a relative (i.e., any decrease or decrease in heart rate relative to a reference value) or in an absolute sense (i.e., a pathological change relative to a normative value). In particular, "tachycardia is used interchangeably with an increase heart rate and "bradycardia" may be used interchangeably with a decrease in heart rate.

A variety of stimulation therapies may be provided in embodiments of the present disclosure. Different nerve fiber types (e.g., A, B, and C-fibers that may be targeted) respond differently to stimulation from electrical signals because they have different conduction velocities and stimulation threshold. Certain pulses of an electrical stimulation signal, for example, may be below the stimulation threshold for a particular fiber and, therefore, may generate no action potential. Thus, smaller or narrower pulses may be used to avoid stimulation of certain nerve fibers (such as C-fibers) and target other nerve fibers (such as A and/or B fibers, which generally have lower stimulation thresholds and higher conduction velocities than C-fibers). Additionally, techniques such as a pre-pulse may be employed wherein axons of the target neural structure may be partially depolarized (e.g., with a pre-pulse or initial phase of a pulse) before a greater current is delivered to the target (e.g., with a second pulse or an initial phase such a stair step pre-pulse to deliver a larger quantum of charge). Furthermore, opposing polarity phases separated by a zero current phase may be used to excite particular axons or postpone nerve fatigue during long term stimulation.

Cranial nerve stimulation, such as vagus nerve stimulation (VNS), has been proposed to treat a number of medical conditions, including epilepsy and other movement disorders, depression and other neuropsychiatric disorders, dementia, traumatic brain injury, coma, migraine headache, obesity, eating disorders, sleep disorders, cardiac disorders (such as congestive heart failure and atrial fibrillation), hypertension, endocrine disorders (such as diabetes and hypoglycemia), and pain, among others. See, e.g., U.S. Pat. Nos. 4,867,164; 5,299,569; 5,269,303; 5,571,150; 5,215,086; 5,188,104; 5,263,480; 6,587,719; 6,609,025; 5,335,657; 6,622,041; 5,916,239; 5,707,400; 5,231,988; and 5,330,515. Despite the variety of disorders for which cranial nerve stimulation has been proposed or suggested, the fact that detailed neural pathways for many (if not all) cranial nerves remain relatively unknown, makes predictions of efficacy for any given disorder difficult or impossible. Even if such pathways were known, the precise stimulation parameters that would modulate particular pathways relevant to a particular disorder generally cannot be predicted.

Cardiac signals suitable for use in embodiments of the present disclosure may comprise one or more of an electrical (e.g., EKG), acoustic (e.g., phonocardiogram or ultrasound/ECHO), force or pressure (e.g., apexcardiogram), arterial pulse pressure and waveform or thermal signals that may be recorded and analyzed to extract features such as heart rate, heart rate variability, rhythm (regular, irregular, sinus, ventricular, ectopic, etc.), morphology, etc.

It appears that sympatho-vagal imbalance (lower vagal and higher sympathetic tone) plays an important role in generation of a wide spectrum of ictal and interictal alterations in cardiac dynamics, ranging from rare unifocal PVCs to cardiac death. Without being bound by theory, restoration of the vagal tone to a level sufficient to counteract the pathological effects of elevated catecholamines may serve a cardio-protective purpose that would be particularly beneficial in patients with pharmaco-resistant epilepsies, who are at highest risk for SUDEP.

In one embodiment, the present disclosure provides methods and apparatus to increase cardiac vagal tone in epilepsy patients by timely delivering therapeutic electrical currents to the trunks of the right or left vagus nerves or to their cardiac rami (branches), in response to increases in sympathetic tone, by monitoring among others, heart rate, heart rhythm, EKG morphology, blood pressure, skin resistance, catecholamine or their metabolites and neurological signals such as EEG/ECoG, kinetic (e.g., amplitude velocity, direction of movements) and cognitive (e.g., complex reaction time).

In one embodiment, the present disclosure provides a method of treating a medical condition selected from the group consisting of epilepsy, neuropsychiatric disorders (including but not limited to depression), eating disorders/obesity, traumatic brain injury, addiction disorders, dementia, sleep disorders, pain, migraine, endocrine/pancreatic disorders (including but not limited to diabetes), motility disorders, hypertension, congestive heart failure/cardiac capillary growth, hearing disorders, angina, syncope, vocal cord disorders, thyroid disorders, pulmonary disorders, gastrointestinal disorders, kidney disorders, and reproductive endocrine disorders (including infertility).

Figure 1B:
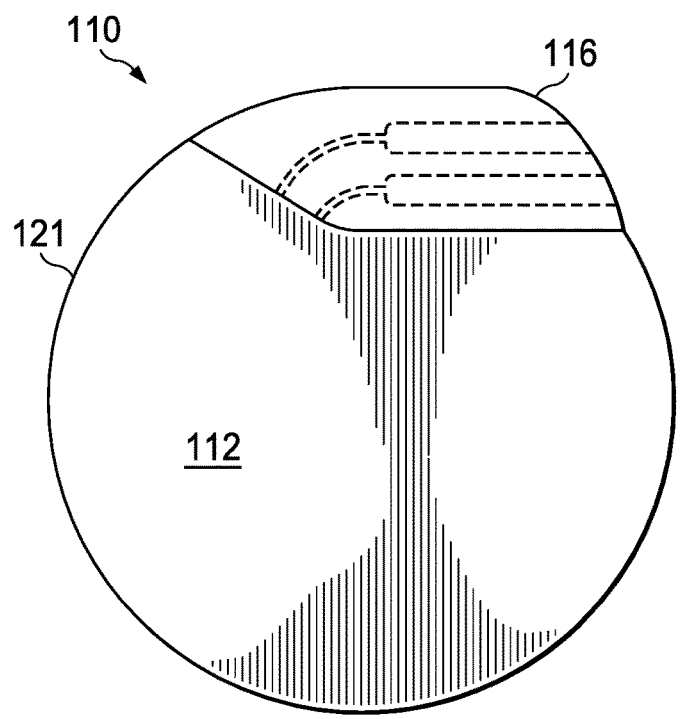

FIGS. 1A-1E depict a stylized implantable medical system 100 for implementing one or more embodiments of the present disclosure. FIGS. 1A and 1B illustrate an electrical signal generator 110 having main body 112 comprising a case or shell (commonly referred to as a "can") 121 (FIG. 1B) with a header 116 for connecting to a lead assembly 122. An electrode assembly 125, preferably comprising at least an electrode pair, is conductively connected to the distal end of an insulated, electrically conductive lead assembly 122, which preferably comprises a plurality of lead wires (at least one wire for each electrode of the electrode assembly 125). Lead assembly 122 is attached at its proximal end to one or more connectors on header 116 (FIG. 1B).

Electrode assembly 125 may be surgically coupled to a target tissue for delivery of a therapeutic electrical signal, which may be a pulsed electrical signal. The target tissue may be a cranial nerve, such as a vagus nerve 127 (FIGS. 1A, 1C-E) or another cranial nerve such as a trigeminal nerve. Electrode assembly 125 includes one or more electrodes 125-1, 125-2, 125-3, which may be coupled to the target tissue. The electrodes may be made from any of a variety of conductive metals known in the art, e.g., platinum, iridium, oxides of platinum or iridium, or combinations of the foregoing. In one embodiment, the target tissue is a vagus nerve 127, which may include an upper main trunk portion 127-1 above a cardiac branch 127-2, and a lower main trunk portion 127-3 below the cardiac branch.

Figure 1C:
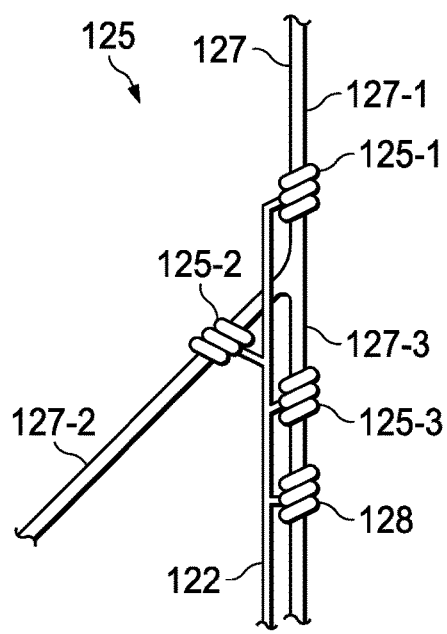

In one embodiment, at least one electrode may be coupled to the main trunk of the vagus nerve, and at least one electrode 125-2 may be coupled to a cardiac branch 127-2 of the vagus nerve (FIG. 1C). The at least one main trunk electrode may be coupled to an upper main trunk 127-1 (e.g., electrode 125-1, FIG. 1C) or a lower main trunk 127-3 (e.g., electrode 125-3). The at least one main trunk electrode (125-1, 125-3) may be used as a cathode to provide a first electrical signal to the upper (127-1) or lower (127-3) main trunk. Cardiac branch electrode 125-2 may be used as a cathode to provide a second electrical signal to cardiac branch 127-2. An additional electrode to function as the anode may be selected from one or more of the other electrodes in electrode assembly 125, can 121, or a dedicated anode.

In some embodiments (FIGS. 1D, 1E), electrode assembly 125 may include a main trunk electrode pair comprising a cathode 125-1a and an anode 125-1b for coupling to a main trunk of a vagus nerve 127. The main trunk electrode pair 125-1a, 125-1b may be coupled to an upper main trunk 127-1 of a vagus nerve (FIG. 1D), or to a lower main trunk 127-3 (FIG. 1E) for delivering a first electrical signal. Without being bound by theory, it is believed that few or no vagal afferent fibers in the lower main trunk 127-3 pass into cardiac branch 127-2 and, accordingly, that effects of the first electrical signal on cardiac function may be minimized by coupling electrode pair 125-1a and 125-1b to the lower main trunk 127-3 instead of upper main trunk 127-1. Cardiac effects may also be minimized by alternative embodiments in which the first electrical signal is applied to a lower main trunk 127-3 using a single electrode (e.g., 125-3, FIG. 1C) as a cathode and an anode that is not coupled to the vagus nerve 127 (e.g., by using can 121 as an anode).

In some embodiments (FIGS. 1D, 1E), electrode assembly 125 may include a cardiac branch electrode pair comprising a cathode 125-2a and an anode 125-2b for coupling to a cardiac branch of a vagus nerve. The second cardiac branch electrode pair may be used to provide a second electrical signal to a cardiac branch of the nerve to affect the cardiac function of the patient.

Referring again to FIGS. 1C-1E, a first electrical signal may be provided to generate afferent action potentials in a main trunk of a vagus nerve to modulate electrical activity of the patient's brain without significantly affecting the patient's heart rate. The second electrical signal may generate efferent action potentials to modulate the cardiac activity of the patient, and in particular to slow the patient's heart rate (e.g., to treat an epilepsy patient having seizures characterized by ictal tachycardia) and maintain or restore a sympathetic/parasympathetic balance to a non-pathological state. The first electrical signal may be applied to the main trunk of the vagus nerve in a variety of ways, so long as at least one electrode is coupled to the main trunk as a cathode. As noted, the cathode may be coupled to either an upper (127-1) or lower (127-3) main trunk, and an anode may be provided by any of the other electrodes on the vagus nerve (e.g., 125-1b, 125-2b, 125-3, FIG. 1C-1E) or by a separate anode not coupled to the vagus nerve (e.g., can 121). In one alternative embodiment, an electrode 125-3 may be coupled to a lower main trunk 127-3 of the vagus nerve to function as an anode. In yet another embodiment, each individual electrode element in FIGS. 1A-E (e.g., 125-1, 125-2, 125-3, 125-1a, 125-1g, 125-2a, 125-2b) may comprise an electrode pair comprising both an anode and a cathode. In an additional embodiment, each individual electrode element may comprise three electrodes (e.g., one serving as cathode and the other two as anodes). Suitable electrode assemblies are available from Cyberonics, Inc., Houston, Tex., USA as the Model 302, PerenniaFlex and PerenniaDura electrode assemblies. In view of the present disclosure, persons of skill in the art will appreciate that many electrode designs could be used in embodiments of the present disclosure including unipolar electrodes.

Embodiments of the present disclosure may comprise electrical signals with either charge-balanced or non-charge-balanced pulses (e.g., monopolar/monophasic, direct current (DC)). Charge-balanced pulses involve a first phase in which the stimulation occurs (i.e., action potentials are induced in target nerve fibers), and a second phase in which the polarity of the electrodes are reversed (i.e., the stimulation phase cathode becomes the charge-balancing phase anode, and vice versa). The result is a pulse having two opposite-polarity phases of equal charge, such that no net charge flows across the electrode during a pulse. Charge-balancing is often used to avoid damage to the electrodes that may result if a pulse results in a net charge flowing across the electrodes.

In some instances, charge-balancing may involve a passive discharge phase as illustrated in, e.g., FIG. 1A of US Publication 2006/0173493, which is hereby incorporated by reference in its entirety. In passive charge-balancing, the charge-balancing phase typically involves allowing a capacitor having a charge equal to the charge applied to the nerve during the stimulation phase to discharge through the polarity-reversed electrodes. Passive charge-balancing typically uses much lower initial current than the stimulation phase, with the current declining to zero over a much longer time period than the pulse width of the stimulation phase. A lower current is typically selected in the charge-balancing phase so as to avoid or minimize nerve recruitment during the charge-balancing phase. In active charge-balancing, the charge-balancing phase is not accomplished by the passive discharge of a capacitor, but by providing a second phase having an opposite polarity but the same charge magnitude (pulse width multiplied by current) as the first phase. As is usually the case with passive charge-balancing, active charge-balancing typically involves a much lower current that is applied over a longer time period than the stimulation phase, so as to avoid nerve recruitment. In some instances, however, the active charge-balancing phase may be used as a second stimulation phase by selecting a current magnitude of the cathode in the charge-balancing phase (typically a second electrode, which may be the anode of the initial stimulation phase) that is sufficient to generate action potentials in nerve fibers of the target tissue.

Embodiments of the present disclosure may be implemented using passive charge balancing or active charge-balancing, and the latter may be provided as a stimulation phase or a non-stimulation phase. Some embodiments may be implemented with non-charge-balanced pulses. Persons of skill in the art, having the benefit of the present disclosure, may select the type of charge balancing (if desired) based upon a number of factors including but not limited to whether or not the charge-balancing is intended to affect the cardiac cycle or not, whether afferent or efferent stimulation is desired, the number and location of available electrodes for applying the electrical signal, the fibers intended to be recruited during a particular phase and their physiological effects, among many other factors.

In the discussion of electrical signals in the present disclosure, unless otherwise stated, references to electrodes as cathodes or anodes refers to the polarities of the electrodes during a stimulation phase of a pulse, whether the pulse is a charge-balanced pulse or a non-charge-balanced pulse (e.g., monopolar/monophasic or DC). It will be appreciated that where charge-balanced pulses are employed, the polarities will be reversed during a charge-balancing phase. Where active charge-balancing is used, cardiac effects may be further amplified or ameliorated, depending upon the location of the electrodes being used.

Returning to FIG. 1A, in some embodiments, a heart rate sensor 130, and/or a kinetic sensor 140 (e.g., a triaxial accelerometer) may be included in the system 100 to sense one or more of a cardiac signal or data stream and a kinetic data stream of the patient. In one embodiment, the heart rate sensor may comprise a separate element 130 that may be coupled to generator 110 through header 116 as illustrated in FIG. 1A. In another embodiment, the electrodes 125-1, 125-2, 125-3 and/or the can 121 may be used as sensing electrodes to sense heart rate. An accelerometer may be provided inside generator 110 in one embodiment to sense a kinetic signal (e.g., body movement) of the patient. One or more of the heart rate sensor 130 and the kinetic sensor 140 may be used by a seizure detection algorithm in the system 100 to detect epileptic seizures. In alternative embodiments, other body signals (e.g., blood pressure, brain activity, blood oxygen/$CO_2$ concentrations, temperature, skin resistivity, etc.) of the patient may be sensed and used by the seizure detection algorithm to detect epileptic seizures. Signal generator 110 may be implanted in the patient's chest in a pocket or cavity formed by the implanting surgeon below the skin (indicated by line 145, FIG. 1A).

Returning to FIGS. 1A and 1C, a first electrode 125-1 may be wrapped or otherwise electrically coupled to an upper main trunk 127-1 of a vagus nerve 127 of the patient, and a second electrode 125-2 may be wrapped or coupled to a cardiac branch 127-2 of the vagus nerve. In one embodiment, a third electrode 125-3 may be coupled to a lower main trunk 127-3 of the vagus nerve below the cardiac branch 127-2 of the vagus nerve, instead of or in addition to first electrode 125-1 coupled to the upper main trunk above the cardiac branch. In some embodiments, third electrode 125-3 may be omitted. Electrode assembly 125 may be secured to the nerve by a spiral anchoring tether 128 (FIG. 1C), which in one embodiment does not include an electrode but in alternative embodiments may contain up to three electrodes that serve as cathode(s) and anode(s) in any possible combination. Lead assembly 122 may further be secured, while retaining the ability to flex, by a suture connection 130 to nearby tissue (FIG. 1C). In particular embodiments, any of first, second and third electrodes 125-1, 125-2, and 125-3 may be used as either a cathode or as an anode. In general, the foregoing electrodes may be used as a cathode when the particular electrode is the closest electrode (among a plurality of electrodes) to the target organ (e.g., heart, brain, stomach, liver, etc.) to be stimulated. While a single electrode (e.g., 125-1, 125-2, or 125-3) is illustrated in connection with upper main trunk 127-1, cardiac branch 127-2, and lower main trunk 127-3 in FIGS. 1A and 1C for simplicity, it will be appreciated that one or more additional electrodes can be provided on each of the foregoing neural structures to provide greater flexibility in stimulation.

In one embodiment, the open helical design of the electrodes 125-1, 125-2, 125-3, is self-sizing, flexible, minimize mechanical trauma to the nerve and allow body fluid interchange with the nerve. The electrode assembly 125 preferably conforms to the shape of the nerve, providing a low stimulation threshold by allowing a large stimulation contact area with the nerve. Structurally, the electrode assembly 125 comprises an electrode ribbon (not shown) for each of electrodes 125-1, 125-2, 125-3, made of a conductive material such as platinum, iridium, platinum-iridium alloys, and/or oxides thereof. The electrode ribbons are individually bonded to an inside surface of an elastomeric body portion of the spiral electrodes 125-1, 125-2, 125-3 (FIG. 1C), which may comprise spiral loops of a multi-loop helical assembly. Lead assembly 122 may comprise three distinct lead wires or a triaxial cable that are respectively coupled to one of the conductive electrode ribbons. One suitable method of coupling the lead wires to the electrodes 125-1, 125-2, 125-3 comprises a spacer assembly such as that disclosed in U.S. Pat. No. 5,531,778, although other known coupling methods may be used.

The elastomeric body portion of each loop may be composed of silicone rubber or other biocompatible elastomeric compounds, and the fourth loop 128 (which may have no electrode in some embodiments) acts as the anchoring tether for the electrode assembly 125.

In one embodiment, electrical pulse generator 110 may be programmed with an external computer 150 using programming software known in the art for stimulating neural structures, and a programming wand 155 to facilitate radio frequency (RF) communication between the external computer 150 (FIG. 1A) and the implanted pulse generator 110. In one embodiment, wand 155 and software permit wireless, non-invasive communication with the generator 110 after surgical implantation. Wand 155 may be powered by internal batteries, and provided with a "power on" light to indicate sufficient power for communications. Another indicator light may be provided to show that data transmission is occurring between the wand and the generator. In other embodiments, wand 155 may be omitted, e.g., where communications occur in the 401-406 MHz bandwidth for Medical Implant Communication Service (MICS band).

In some embodiments of the disclosure, a body data stream may be analyzed to determine whether or not a seizure has occurred. Many different body data streams and seizure detection indices have been proposed for detecting epileptic seizures. Additional details on method of detecting seizure from body data are provided in U.S. Pat. Nos. 8,337,404 and 8,382,667, both issued in the name of the present applicant and both entitled, "Detecting, Quantifying, and/or Classifying Seizures Using Multimodal Data," as well as in co-pending U.S. patent application Ser. No. 13/288,886, filed Nov. 3, 2011, each hereby incorporated by reference in its entirety herein. Seizure detection based on the patient's heart rate (as sensed by implanted or external electrodes), movement (as sensed by, e.g., a triaxial accelerometer), responsiveness, breathing, blood oxygen saturation, skin resistivity/conductivity, temperature, brain activity, and a number of other body data streams are provided in the foregoing patents and co-pending applications.

In one embodiment, the present disclosure provides a method for treating a patient with epilepsy in which a body data stream is analyzed using a seizure detection algorithm to determine whether or not the patient has had an epileptic seizure. As used herein, the term "has had an epileptic seizure" includes instances in which a seizure onset has been detected, as well as instances in which the seizure onset has been detected and the seizure is still ongoing (i.e., the seizure has not ended). If the analysis results in a determination that the patient has not had an epileptic seizure, a signal generator may apply a first electrical signal to a main trunk of a vagus nerve of the patient. If the analysis results in a determination that the patient has had an epileptic seizure, the signal generator may apply a second electrical signal to a cardiac branch of a vagus nerve of the patient. In some embodiments, the application of the first electrical signal to the main trunk is terminated, and only the second electrical signal to the cardiac branch is provided once a seizure is detected.

In alternative embodiments, both the first and second electrical signals may be applied to the main trunk and cardiac branch, respectively, of the vagus nerve in response to a determination that the patient has had a seizure (i.e., the first electrical signal continues to be applied to the main trunk of the vagus nerve and the second signal is initiated). Where both the first and second electrical signals are provided, the two signals may be provided sequentially, or in alternating fashion to the main trunk and the cardiac branch. In one embodiment, the first signal may be provided to the main trunk by using one of the upper main trunk electrode 125-1 or the lower main trunk electrode 125-3 as the cathode and the cardiac branch electrode 125-2 as the anode, or by using both of the upper main trunk electrode and the lower main trunk electrode as the cathode and the anode. The second signal may be provided (e.g., by rapidly changing the polarity of the electrodes) by using the cardiac branch electrode 125-2 as the cathode and a main trunk electrode 125-1 or 125-3 as the anode.

In still other embodiments, the second electrical signal is applied to the cardiac branch of the vagus nerve only if the analysis results in a determination that the patient is having and/or has had an epileptic event that is accompanied by an increase in heart rate, and the second electrical signal is used to lower the heart rate back towards a rate that existed prior to the seizure onset. Without being bound by theory, the present inventors believe that slowing the heart rate at the onset of seizures—particularly where the seizure is accompanied by an increase in heart rate—may improve the ability of VNS therapy to provide cardio-protective benefits.

Prior patents describing vagus nerve stimulation as a medical therapy have cautioned that undesired slowing of the heart rate may occur, and have proposed various methods of avoiding such a slowing of the heart rate. In U.S. Pat. No. 6,341,236, it is suggested to sense heart rate during delivery of VNS and if a slowing of the heart rate is detected, either suspending delivery of the VNS signal or pacing the heart using a pacemaker. The present application discloses a VNS system that detects epileptic seizures, particularly epileptic seizures accompanied by an increase in heart rate, and intentionally applies an electrical signal to slow the heart rate in response to such a detection. In another aspect, the present application discloses VNS systems that provide a first electrical signal to modulate only the brain during periods in which no seizure has been detected, and either 1) a second electrical signal to modulate only the heart (to slow its rate) or 2) both a first electrical signal to the brain and a second electrical signal to the heart, in response to a detection of the onset of an epileptic seizure. These electrical signals may be delivered simultaneously, sequentially (e.g., delivery of stimulation to the brain precedes delivery of stimulation to the heart or vice versa), or delivery of the first and second signals may be interspersed or interleaved.

The first electrode may be used as a cathode to provide an afferent first electrical signal to modulate the brain of the patient via main trunk electrode 125-1. Electrode 125-1 may generate both afferent and efferent action potentials in vagus nerve 127. One or more of electrodes 125-2 and 125-3 are used as anodes to complete the circuit. Where this is the case, some of the action potentials may be blocked at the anode(s), with the result that the first electrical signal may predominantly modulate the brain by afferent actions traveling toward the brain, but may also modulate one or more other organs by efferent action potentials traveling toward the heart and/or lower organs, to the extent that the efferent action potentials are not blocked by the anode(s).

The second electrode may be used as a cathode to provide an efferent second electrical signal to slow the heart rate of the patient via cardiac branch electrode 125-2. Either first electrode 125-1 or a third electrode 125-3 (or can 121) may be used as an anode to complete the circuit. In one embodiment, the first electrical signal may be applied to the upper (127-1) or lower (127-3) main trunk of the vagus nerve in an open-loop manner according to programmed parameters including an off-time and an on-time. The on-time and off-time together establish the duty cycle determining the fraction of time that the signal generator applies the first electrical. In one embodiment, the off-time may range from 7 seconds to several hours or even longer, and the on-time may range from 5 seconds to 300 seconds. It should be noted that the duty cycle does not indicate when current is flowing through the circuit, which is determined from the on-time together with the pulse frequency (usually 10-200, Hz, and more commonly 20-30 Hz) and pulse width (typically 0.1-0.5 milliseconds). The first electrical signal may also be defined by a current magnitude (e.g., 0.25-3.5 milliamps), and possibly other parameters (e.g., pulse width, and whether or not a current ramp-up and/or ramp-down is provided, a frequency, and a pulse width).

In one embodiment, a seizure detection may result in both applying the first electrical signal to provide stimulation to the brain in close proximity to a seizure detection (which may interrupt or terminate the seizure), as well as application of the second electrical signal which may slow the heart, thus exerting a cardio-protective effect. In a particular embodiment, the second electrical signal is applied only in response to a seizure detection that is characterized by (or accompanied or associated with) an increase in heart rate, and is not applied in response to seizure detections that are not characterized by an increase in heart rate. In this manner, the second electrical signal may help interrupt the seizure by restoring the heart to a pre-seizure baseline heart rate when the patient experiences ictal tachycardia (elevated heart rate during the seizure), while leaving the heart rate unchanged if the seizure has no significant effect on heart rate.

In still further embodiments, additional logical conditions may be established to control when the second electrical signal is applied to lower the patient's heart rate following a seizure detection. In one embodiment, the second electrical signal is applied only if the magnitude of the ictal tachycardia rises above a defined level. In one embodiment, the second electrical signal is applied to the cardiac branch only if the heart rate increases by a threshold amount above the pre-ictal baseline heart rate (e.g., more than 20 beats per minute above the baseline rate). In another embodiment, the second electrical signal is applied to the cardiac branch only if the heart rate exceeds an absolute heart rate threshold (e.g., 100 beats per minute, 120 beats per minute, or other programmable threshold). In a further embodiment, a duration constraint may be added to one or both of the heart rate increase or absolute heart rate thresholds, such as a requirement that the heart rate exceed the baseline rate by 20 beats per minute for more than 10 seconds, or exceed 110 beats per minute for more than 10 seconds, before the second electrical signal is applied to the cardiac branch in response to a seizure detection.

In another embodiment, the heart rate sensor continues to monitor the patient's heart rate during and/or after application of the second electrical signal, and the second electrical signal is interrupted or terminated if the patient's heart rate is reduced below a low heart rate threshold, which may be the baseline heart rate that the patient experienced prior to the seizure, or a rate lower or higher than the baseline pre-ictal heart rate. The low rate threshold may provide a measure of safety to avoid undesired events such as bradycardia and/or syncope.

In yet another embodiment, heart rate sensor 130 may continue to monitor heart rate and/or kinetic sensor 140 may continue to monitor body movement in response to applying the second electrical signal, and the second electrical signal may be modified (e.g., by changing one or more parameters such as pulse frequency, or by interrupting and re-initiating the application of the second electrical signal to the cardiac branch of the vagus nerve) to control the heart rate below an upper heart rate threshold and/or body movement exceeds one or more movement thresholds. For example, the frequency or duration of the second electrical signal applied to the cardiac branch of the vagus nerve may be continuously modified based the instantaneous heart rate as monitored during the course of a seizure to control what would otherwise be an episode of ictal tachycardia below an upper heart rate threshold. In one exemplary embodiment, the second electrical signal may be programmed to provide a 30-second pulse burst at 30 Hz, with the pulses having a pulse width of 0.25 milliseconds and a current of 1.5 milliamps. If, at the end of the 30 second burst, the heart rate remains above 120 beats per minute, and is continuing to rise, the burst may be extended to 1 minute instead of 30 seconds, the frequency may be increased to 50 Hz, the pulse width may be increased to 350 milliseconds, or combinations of the foregoing. In still further embodiments, additional therapies (e.g., oxygen delivery, drug delivery, cooling therapies, etc.) may be provided to the patient if the body data (heart rate, kinetic activity, etc.) indicates that the patient's seizure is not under control or terminated.

Abnormalities or changes in EKG morphology or rhythm relative to an interictal morphology or rhythm may also trigger delivery of current to the heart via the trunks of vagi or its cardiac rami. In other embodiments, pharmacological agents such as beta-blockers may be automatically released into a patient's blood stream in response to the detection of abnormal heart activity during or between seizures.

In one embodiment, the first electrical signal and the second electrical signal are substantially identical. In another embodiment, the first electrical signal may vary from the second electrical signal in terms of one or more of pulse width, number of pulses, amplitude, frequency, interpulse-interval, stimulation on-time, and stimulation off-time, among other parameters and degree, rate or type of charge balancing.

The number of pulses applied to the main trunk or cardiac branch, respectively, before changing the polarity of the first and second electrodes need not be one. Thus, two or more pulses may be applied to the main trunk before applying pulses to the cardiac branch of the vagus nerve. More generally, the first and second signals can be independent of one another and applied according to timing and programming parameters controlled by the controller 210 and stimulation unit 220.

In one embodiment, one or more pulse bursts of the first electrical signal are applied to the main trunk of the vagus nerve in response to a detected seizure before applying one or more bursts of the second electrical signal to the cardiac branch. In another embodiment, the first and second signals are interleaved on a pulse-by-pulse basis under the control of the controller 210 and stimulation unit 220.

Typically, VNS can be performed with pulse frequency of 20-30 Hz (resulting in a number of pulses per burst of 140-1800, at a burst duration from 7-60 sec). In one embodiment, at least one of the first electrical signal and the second electrical signal comprises a microburst signal. Microburst neurostimulation is discussed by U.S. patent Ser. No. 11/693,451, filed Mar. 2, 2007 and published as United States patent Publication No. 20070233193, and incorporated herein by reference in its entirety. In one embodiment, at least one of the first electrical signal, the second electrical signal, and the third electrical signal is characterized by having a number of pulses per microburst from 2 pulses to about 25 pulses, an interpulse interval of about 2 msec to about 50 msec, an interburst period of at least 100 msec, and a microburst duration of less than about 1 sec.

Cranial nerves such as the vagus nerve include different types of nerve fibers, such as A-fibers, B-fibers and C-fibers. The different fiber types propagate action potentials at different velocities. Each nerve fiber is directional—that is, endogenous or natural action potentials can generally propagate action potentials in only one direction(e.g., afferently to the brain or efferently to the heart and/or viscera). That direction is referred to as the orthodromic direction. Exogenous stimulation (e.g., by electrical pulses) may induce action potentials in both the orthodromic direction as well as the antidromic direction. Depending upon the desired effects of stimulation (e.g., afferent modulation of the brain, efferent modulation of the heart, etc.) certain measures (e.g., cooling, pressure, etc.) may be taken to block propagation in either the efferent or the afferent direction. It is believed that the anode may block at least some action potentials traveling to it from the cathode. For example, referring to FIG. 1, both afferent and efferent action potentials may be generated in an upper main trunk of vagus nerve 127-1 by applying a pulse to the nerve using upper main trunk electrode 125-1 as a cathode. Action potentials generated at upper main trunk electrode 125-1 and traveling toward the heart on cardiac branch 127-2 may be blocked by cardiac branch anode 125-2. Action potentials traveling from the upper main trunk 127-1 to the lower organs in lower main trunk 127-3 may be either blocked (by using lower main trunk electrode 125-3 as an anode either with or instead of cardiac branch electrode 125-2) or allowed to travel to the lower organs (by not using electrode structure 125-3 as an electrode).

Action potentials may be generated and allowed to travel to the heart by making the electrode 125-2 the cathode. If cardiac branch electrode 125-2 is used as a cathode, action potentials will reach the heart in large numbers, while action potentials traveling afferently toward the brain may be blocked in the upper trunk if upper electrode 125-1 is made the anode.

In a further embodiment of the disclosure, rapid changes in electrode polarity may be used to generate action potentials to collision block action potentials propagating in the opposite direction. To generalize, in some embodiments, the vagus nerve can be selectively stimulated to propagate action potentials either afferently (i.e., to the brain) or efferently (i.e., to the heart and/or lower organs/viscerae).

Turning now to FIG. 2, a block diagram depiction of an implantable medical device, in accordance with one illustrative embodiment of the present disclosure is illustrated. The IMD 200 may be coupled to various electrodes 125 and/or 127 via lead(s) 122 (FIGS. 1A, 1C). First and second electrical signals used for therapy may be transmitted from the IMD 200 to target areas of the patient's body, specifically to various electrodes associated with the leads 122. Stimulation signals from the IMD 200 may be transmitted via the leads 122 to stimulation electrodes (electrodes that apply the therapeutic electrical signal to the target tissue) associated with the electrode assembly 125, e.g., 125-1, 125-2, 125-3 (FIG. 1A).

The IMD 200 may comprise a controller 210 capable of controlling various aspects of the operation of the IMD 200. The controller 210 is capable of receiving internal data and/or external data and controlling the generation and delivery of a stimulation signal to target tissues of the patient's body. For example, the controller 210 may receive manual instructions from an operator externally, may perform stimulation based on internal calculations and programming, and may receive and/or process sensor data received from one or more body data sensors such as electrodes 125-1, 125-2, 125-3, or heart rate sensor 130. The controller 210 is capable of affecting substantially all functions of the IMD 200.

The controller 210 may comprise various components, such as a processor 215, a memory 217, etc. The processor 215 may comprise one or more micro controllers, microprocessors, etc., that are capable of executing a variety of software components. The processor may receive, pre-condition and/or condition sensor signals, and may control operations of other components of the IMD 200, such as stimulation unit 220, seizure detection module 240, logic unit 250, communication unit, 260, and electrode polarity reversal unit 280. The memory 217 may comprise various memory portions, where a number of types of data (e.g., internal data, external data instructions, software codes, status data, diagnostic data, etc.) may be stored. The memory 217 may store various tables or other database content that could be used by the IMD 200 to implement the override of normal operations. The memory 217 may comprise random access memory (RAM) dynamic random access memory (DRAM), electrically erasable programmable read-only memory (EEPROM), flash memory, etc.

The IMD 200 may also comprise a stimulation unit 220. The stimulation unit 220 is capable of generating and delivering a variety of electrical signal therapy signals to one or more electrodes via leads. The stimulation unit 220 is capable of delivering a programmed, first electrical signal to the leads 122 coupled to the IMD 200. The electrical signal may be delivered to the leads 122 by the stimulation unit 220 based upon instructions from the controller 210. The stimulation unit 220 may comprise various types of circuitry, such as stimulation signal generators, impedance control circuitry to control the impedance "seen" by the leads, and other circuitry that receives instructions relating to the type of stimulation to be performed.

Signals from sensors (electrodes that are used to sense one or more body parameters such as temperature, heart rate, brain activity, etc.) may be provided to the IMD 200. The body signal data from the sensors may be used by a seizure detection algorithm embedded or processed in seizure detection module 240 to determine whether or not the patient is having and/or has had an epileptic seizure. The seizure detection algorithm may comprise hardware, software, firmware or combinations thereof, and may operate under the control of the controller 210. Although not shown, additional signal conditioning and filter elements (e.g., amplifiers, D/A converters, etc., may be used to appropriately condition the signal for use by the seizure detection module 240. Sensors such as heart sensor 130 and kinetic sensor 140 may be used to detect seizures, along with other autonomic, neurologic, or other body data.

The IMD 200 may also comprise an electrode polarity reversal unit 280. The electrode polarity reversal unit 280 is capable of reversing the polarity of electrodes (125-1, 125-2, 125-3) associated with the electrode assembly 125. The electrode polarity reversal unit 280 is shown in more detail in FIG. 3. In preferred embodiments, the electrode polarity reversal unit is capable of reversing electrode polarity rapidly, i.e., in about 10 microseconds or less, and in any event at a sufficiently rapid rate to permit electrode polarities to be changed between adjacent pulses in a pulsed electrical signal.

The IMD 200 may also comprise a power supply 230. The power supply 230 may comprise a battery, voltage regulators, capacitors, etc., to provide power for the operation of the IMD 200, including delivering the stimulation signal. The power supply 230 comprises a power-source battery that in some embodiments may be rechargeable. In other embodiments, a non-rechargeable battery may be used. The power supply 230 provides power for the operation of the IMD 200, including electronic operations and the stimulation function. The power supply 230 may comprise a lithium/thionyl chloride cell or a lithium/carbon monofluoride (LiCFx) cell. Other battery types known in the art of implantable medical devices may also be used.

The IMD 200 also comprises a communication unit 260 capable of facilitating communications between the IMD 200 and various devices. In particular, the communication unit 260 is capable of providing transmission and reception of electronic signals to and from an external unit 270. The external unit 270 may be a device that is capable of programming various modules and stimulation parameters of the IMD 200. In one embodiment, the external unit 270 comprises a computer system that is capable of executing a data-acquisition program. The external unit 270 may be controlled by a healthcare provider, such as a physician, at a base station in, for example, a doctor's office. The external unit 270 may be a computer, preferably a handheld computer or PDA, but may alternatively comprise any other device that is capable of electronic communications and programming The external unit 270 may download various parameters and program software into the IMD 200 for programming the operation of the implantable device. The external unit 270 may also receive and upload various status conditions and other data from the IMD 200. The communication unit 260 may be hardware, software, firmware, and/or any combination thereof. Communications between the external unit 270 and the communication unit 260 may occur via a wireless or other type of communication, illustrated generally by line 275 in FIG. 2.

In one embodiment, the communication unit 260 can transmit a log of stimulation data and/or seizure detection data to the patient, a physician, or another party.

Figure 1D:
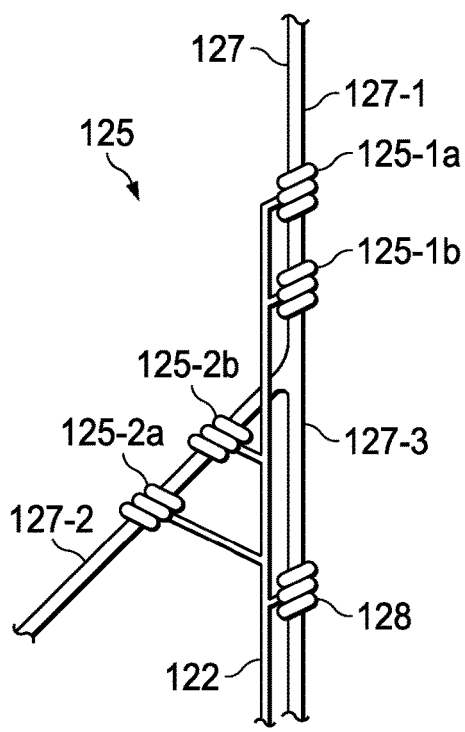
Figure 1E:
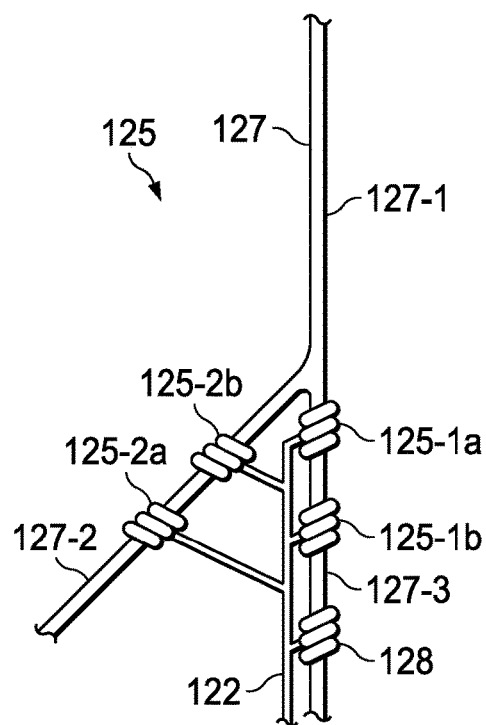

In one embodiment, a method of treating an epileptic seizure is provided that involves providing simultaneously both a first electrical signal to a main trunk of a vagus nerve and a second electrical signal to a cardiac branch of the vagus nerve. As used herein "simultaneously" refers to the on-time of the first and second signals, and does not require that individual pulses of the first signal and the second signal be simultaneously applied to target tissue. The timing of pulses for the first electrical signal and the second electrical signal may be determined by controller 210 in conjunction with stimulation unit 220. Where active charge-balancing is used, it may be possible to use the active charge-balancing phase of pulses of the first electrical signal as the stimulation phase of the second electrical signal by selecting a current magnitude of the cathode in the charge-balancing phase (typically a second electrode, which may be the anode of the initial stimulation phase) that is sufficient to generate action potentials in nerve fibers of the target tissue. Controller 210 may in some embodiments provide simultaneous delivery of first and second electrical signals by interleaving pulses for each of the first and second electrical signals based upon the programmed timing of pulses for each signal and the appropriate polarity of each of first and second electrodes 125-1 and 125-2. In some embodiments, additional electrodes may be used to minimize the induction of action potentials to the heart or the brain provided by the first electrical signal or the second electrical signal. This may be accomplished, in one embodiment, by using an anode located on either the upper main trunk or the cardiac branch to block impulse conduction to the heart or brain from the cathode, or by providing dedicated electrode pairs on both the main trunk and cardiac branches (FIGS. 1D, 1E). When beneficial, steps to avoid collisions of actions potentials travelling in opposite directions may be implemented, while steps to promote collisions may be taken when clinically indicated. In some embodiments, the method further includes sensing a cardiac signal and a kinetic signal of the patient, and detecting a seizure event with a seizure detection algorithm.

In one embodiment, a first electrical signal is applied to a main trunk of a vagus nerve and a second electrical signal is simultaneously applied to a cardiac branch of a vagus nerve. A pulse of the first electrical signal is generated with the electrical signal generator 110 and applied to the main trunk of the vagus nerve using a first electrode (e.g., 125-1, 125-1*a*) as a cathode and a second electrode (e.g., 125-1*b*, 125-3, or 125-2) as an anode. The method includes sensing a cardiac signal and a kinetic signal of the patient, and detecting a seizure event with a seizure detection algorithm. A pulse of the second electrical signal (having the appropriate pulse width and current) is generated and applied (under appropriate timing control by controller 110 and stimulation unit 220) to the cardiac branch of the vagus nerve using a second electrode (e.g., 125-2, 125-2*a*) as a cathode and another electrode (e.g., 125-3, 125-1, 125-2*b*) as an anode. Another pulse of the first electrical signal may thereafter be generated and applied to the main trunk under timing and parameter control of controller 210 and stimulation unit 220. By appropriate selection of cathodes and anodes, the first and second electrical signals may be interleaved and provided simultaneously to the main trunk and cardiac branches of the vagus nerve. In some embodiments, the number of electrodes may be minimized by provided a polarity reversal unit that may rapidly change the polarity of particular electrodes to allow their use in delivering both the first and second signals.

The IMD 200 is capable of delivering stimulation that can be contingent, periodic, random, coded, and/or patterned. The stimulation signals may comprise an electrical stimulation frequency of approximately 0.1 to 10,000 Hz. The stimulation signals may comprise a pulse width in the range of approximately 1-2000 micro-seconds. The stimulation signals may comprise current amplitude in the range of approximately 0.1 mA to 10 mA. Appropriate precautions may be taken to avoid delivering injurious current densities to target neural tissues, e.g., by selecting current, voltage, frequency, pulse width, on-time and off-time parameters to maintain current density below thresholds for damaging tissues.

The IMD 200 may also comprise a magnetic field detection unit 290. The magnetic field detection unit 290 is capable of detecting magnetic and/or electromagnetic fields of a predetermined magnitude. Whether the magnetic field results from a magnet placed proximate to the IMD 200, or whether it results from a substantial magnetic field encompassing an area, the magnetic field detection unit 290 is capable of informing the IMD of the existence of a magnetic field. The changeable electrode polarity stimulation described herein may be activated, deactivated, or alternatively activated or deactivated using a magnetic input.

The magnetic field detection unit 290 may comprise various sensors, such as a Reed Switch circuitry, a Hall Effect sensor circuitry, and/or the like. The magnetic field detection unit 290 may also comprise various registers and/or data transceiver circuits that are capable of sending signals that are indicative of various magnetic fields, the time period of such fields, etc. In this manner, the magnetic field detection unit 290 is capable of detecting whether the detected magnetic field relates to an input to implement a particular first or second electrical signal (or both) for application to the main trunk of cardiac branches, respectively, of the vagus nerve.

One or more of the blocks illustrated in the block diagram of the IMD 200 in FIG. 2, may comprise hardware units, software units, firmware units, or any combination thereof. Additionally, one or more blocks illustrated in FIG. 2 may be combined with other blocks, which may represent circuit hardware units, software algorithms, etc. Additionally, one or more of the circuitry and/or software units associated with the various blocks illustrated in FIG. 2 may be combined into a programmable device, such as a field programmable gate array, an ASIC device, etc.

Figure 3:
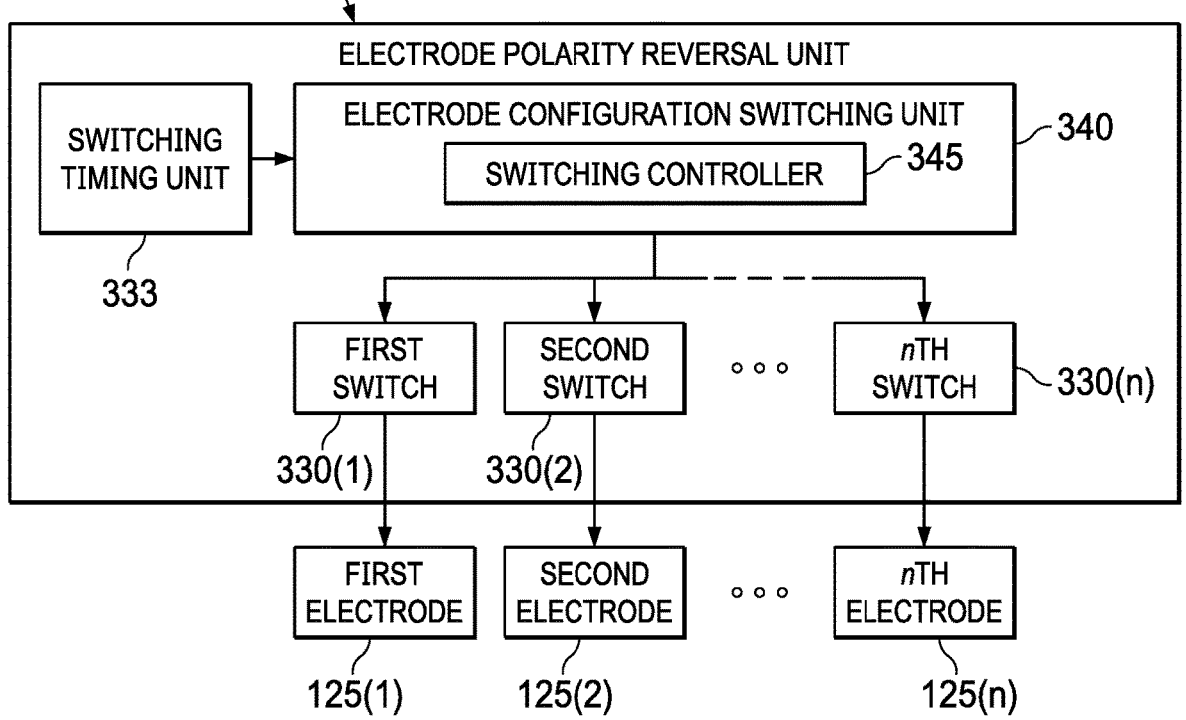
FIG. 3 illustrates a block diagram depiction of an electrode polarity reversal unit shown in FIG. 2, in accordance with one illustrative embodiment of the present disclosure.

FIG. 3 shows in greater detail an electrode polarity reversal unit 280 (FIG. 2) in one embodiment. The electrode polarity reversal unit 280 comprises an electrode configuration switching unit 340, which includes a switching controller 345. The switching controller 345 transmits signals to one or more switches, generically, n switches 330(1), 330(2), . . . 330(n) which effect the switching of the configuration of two or more electrodes, generically, n electrodes 125(1), 125(2), . . . 125(n). Although FIG. 3 shows equal numbers of switches 330 and electrodes 125, persons of skill in the art having the benefit of the present disclosure will understand that the number of switches 330 and their connections with the various electrodes 125 can be varied as a matter of routine optimization. A switching timing unit 333 can signal to the electrode configuration switching unit 340 that a desired time for switching the electrode configuration has been reached.

Instructions for implementing two or more stimulation regimens, which may include at least one open-loop electrical signal and at least one closed-loop electrical signal, may be stored in the IMD 200. These stimulation signals may include data relating to the type of stimulation signal to be implemented. In one embodiment, an open-loop signal may be applied to generate action potentials for modulating the brain of the patient, and a closed-loop signal may be applied to generate either action potentials for slowing the heart rate of the patient, or both action potentials to modulate the brain of the patient as well as action potentials for slowing the heart rate of the patient. In some embodiments, the open-loop and closed-loop signals may be provided to different target portions of a vagus nerve of the patient by switching the polarity of two or more electrodes using an electrode polarity reversal unit as described in FIG. 3 above. In alternative embodiments, additional electrodes may be provided to generate each of the open-loop and closed-loop signals without electrode switching.

In one embodiment, a first open-loop mode of stimulation may be used to provide an electrical signal to a vagus nerve using a first electrode as a cathode on a main trunk (e.g., 127-1 or 127-3 using electrodes 125-1 or 125-3, respectively) of a vagus nerve, and a second electrode as an anode on either a main trunk (e.g., electrode 125-3, when electrode 125-1 is used as a cathode) or cardiac branch (e.g., electrode 125-2) of a vagus nerve. The first open-loop signal may include a programmed on-time and off-time during which electrical pulses are applied (the on-time) and not-applied (the off-time) in a repeating sequence to the vagus nerve.

A second, closed-loop signal may be provided in response to a detected event (such as an epileptic seizure, particularly when accompanied by an increase in the patient's heart rate) using a different electrode configuration than the first, open-loop signal. In one embodiment, the second, closed-loop signal is applied to a cardiac branch using the second electrode 125-2 as a cathode and the first electrode on the main trunk (e.g., 125-1 or 125-3) as an anode. The second, closed-loop signal may involve generating efferent action potentials on the cardiac branch of the vagus nerve to slow the heart rate. In some embodiments, the first, open-loop signal may be interrupted/suspended in response to the detected event, and only the second, closed-loop signal is applied to the nerve. In other embodiments, the first, open loop signal may not be interrupted when the event is detected, and both the first, open-loop signal and the second, closed-loop signal are applied to the vagus nerve. In another embodiment, a third, closed-loop signal may also be provided in response to the detected event. The third, closed-loop signal may involve an electrical signal using the same electrode configuration as the first, open-loop electrical signal, but may provide a different electrical signal to the main trunk of the vagus nerve than either the first, open-loop signal or the second, closed-loop signal. The first, open-loop signal may be interrupted, terminated or suspended in response to the detected event, and the third, closed-loop signal may be applied to the nerve either alone or with the second, closed-loop signal. In some embodiments, both the second and third closed-loop signals may be provided in response to a detected epileptic seizure by rapidly changing the polarity of the first (125-1) and second (125-2) electrodes from cathode to anode and back, as pulses are provided as part of the second and third electrical signals, respectively. In one embodiment, the third electrical signal may involve modulating the brain by using a main trunk electrode (e.g., upper main trunk electrode 125-1) as a cathode and another electrode (e.g., cardiac branch electrode 125-2 or lower main trunk electrode 125-3) as an anode. The third electrical signal may comprise, for example, a signal that is similar to the first electrical signal but which provides a higher electrical current than the first electrical signal, and for a longer duration than the first signal or for a duration that is adaptively determined based upon a sensed body signal (in contrast, for example, to a fixed duration of the first electrical signal determined by a programmed on-time). By rapidly changing polarity of the electrodes, pulses for each of the second and third electrical signals may be provided such that the second and third signals are provided simultaneously to the cardiac branch and main trunk of the vagus nerve. In other embodiments, the first, second and third electrical signals may be provided sequentially rather than simultaneously.

In some embodiments, one or more of the first, second and third electrical signals may comprise a microburst signal, as described more fully in U.S. patent application Ser. Nos. 11/693,421, 11/693,451, and 11/693,499, each filed Mar. 29, 2007 and each hereby incorporated by reference herein in their entirety.

In one embodiment, each of a plurality of stimulation regimens may respectively relate to a particular disorder, or to particular events characterizing the disorder. For example, different electrical signals may be provided to one or both of the main trunk and cardiac branches of the vagus nerve depending upon what effects accompany the seizure. In a particular embodiment, a first open-loop signal may be provided to the patient in the absence of a seizure detection, while a second, closed-loop signal may be provided when a seizure is detected based on a first type of body movement of the patient as detected by, e.g., an accelerometer, a third, closed-loop signal may be provided when the seizure is characterized by a second type of body movement, a fourth, closed-loop signal may be provided when the seizure is characterized by an increase in heart rate, a fifth, closed-loop signal may be provided when the seizure is characterized by a decrease in heart rate, and so on. More generally, stimulation of particular branches or main trunk targets of a vagus nerve may be provided based upon different body signals of the patient. In some embodiments, additional therapies may be provided based on different events that accompany the seizure, e.g., stimulation of a trigeminal nerve or providing a drug therapy to the patient through a drug pump. In one embodiment, different regimens relating to the same disorder may be implemented to accommodate improvements or regressions in the patient's present condition relative to his or her condition at previous times. By providing flexibility in electrode configurations nearly instantaneously, the present disclosure greatly expands the range of adjustments that may be made to respond to changes in the patient's underlying medical condition.

The switching controller 345 may be a processor that is capable of receiving data relating to the stimulation regimens. In an alternative embodiment, the switching controller may be a software or a firmware module. Based upon the particulars of the stimulation regimens, the switching timing unit 333 may provide timing data to the switching controller 345. The first through nth switches 330(1-n) may be electrical devices, electro-mechanical devices, and/or solid state devices (e.g., transistors).

Figure 4:
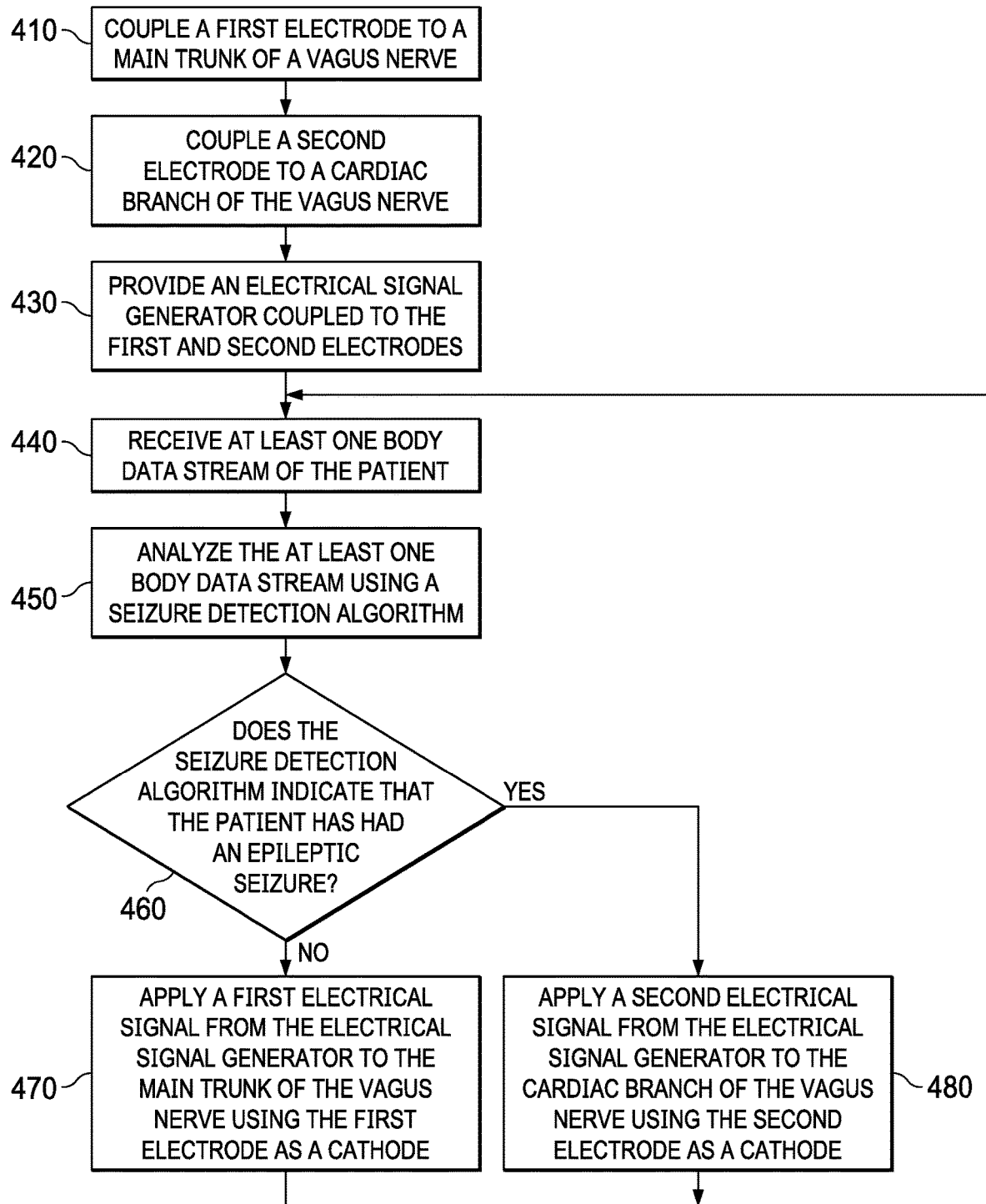
FIG. 4 illustrates a flowchart depiction of a method for providing first and second electrical signals to a main trunk and a cardiac branch of a vagus nerve, respectively, based upon whether or not the patient is having and/or has had an epileptic seizure, in accordance with an illustrative embodiment of the present disclosure.

FIG. 4 shows one embodiment of a method of treating a patient having epilepsy according to the present disclosure. In this embodiment, a first electrode is coupled to a main trunk of a vagus nerve of the patient (410) and a second electrode is coupled to a cardiac branch of the vagus nerve (420). An electrical signal generator is coupled to the first and second electrodes (430).

The method further involves receiving at least one body data stream of the patient (440). The data may be sensed by a sensor such as heart rate sensor 130 (FIG. 1A) or a sensor that is an integral part of, or coupled to, an IMD 200 (FIG. 2) such as electrical pulse generator 110 (FIG. 1A), and the IMD may also receive the data from the sensor. The at least one body data stream is then analyzed using a seizure detection algorithm (450), and the seizure detection algorithm determines whether or not the patient is having and/or has had an epileptic seizure (460).

If the algorithm indicates that the patient is not having and/or has not had an epileptic seizure, the method comprises applying a first electrical signal from the electrical signal generator to the main trunk of a vagus nerve using the first electrode as a cathode (470). In one embodiment, applying the first electrical signal comprises continuing to apply a programmed, open-loop electrical signal periodically to the main trunk of the vagus nerve according a programmed on-time and off-time.

If the algorithm indicates that the patient is having and/or has had an epileptic seizure, the method comprises applying a second electrical signal from the electrical signal generator to the cardiac branch of the vagus nerve using the second electrode as a cathode (480). Depending upon which electrical signal (first or second) is applied, the method may involve changing the polarity of one or both of the first electrode and the second electrode. In one embodiment, the method may comprise suspending the first electrical and applying the second electrical signal. In one embodiment, the method comprises continuing to receive at least one body data stream of the patient at 440 after determining whether or not the patient is having and/or has had an epileptic seizure.

In an alternative embodiment, if the seizure detection algorithm indicates that the patient is having and/or has had an epileptic seizure, both the first electrical signal and the second electrical signal are applied to the main trunk and cardiac branches of a vagus nerve of the patient, respectively, at step 480. In a specific implementation of the alternative embodiment, pulses of the first and second electrical signal are applied to the main trunk and cardiac branch of the vagus nerve under the control of controller 210 by rapidly changing the polarity of the first and second electrodes using the electrode polarity reversal unit 280 to apply the first electrical signal to the main trunk using the first electrode as a cathode and the second electrode as an anode, changing the polarity of the first and second electrodes, and applying the second electrical signal to the cardiac branch using the second electrode as a cathode and the first electrode as an anode. Additional pulses for each signal may be similarly applied by rapidly changing the polarity of the electrodes.

In some embodiments, the first electrical signal and the second electrical signal are applied unilaterally, i.e., to a vagal main trunk and a cardiac branch on the same side of the body. In other embodiments, the first and second electrical signals are applied bilaterally, i.e., the second electrical signal is applied to a cardiac branch on the opposite side of the body from the main vagal trunk to which the first electrical signal is applied. In one embodiment, the first electrical signal is applied to a left main trunk to minimize cardiac effects of the first electrical signal, and the second electrical signal is applied to a right cardiac branch, which modulates the sinoatrial node of the heart to maximize cardiac effects of the second electrical signal.

In alternative embodiments, both the first electrode and the second electrode may be coupled to a cardiac branch of a vagus nerve, with the first electrode (e.g., anode) being proximal to the brain relative to the second electrode, and the second electrode (e.g., cathode) being proximal to the heart relative to the first electrode.

Figure 5:
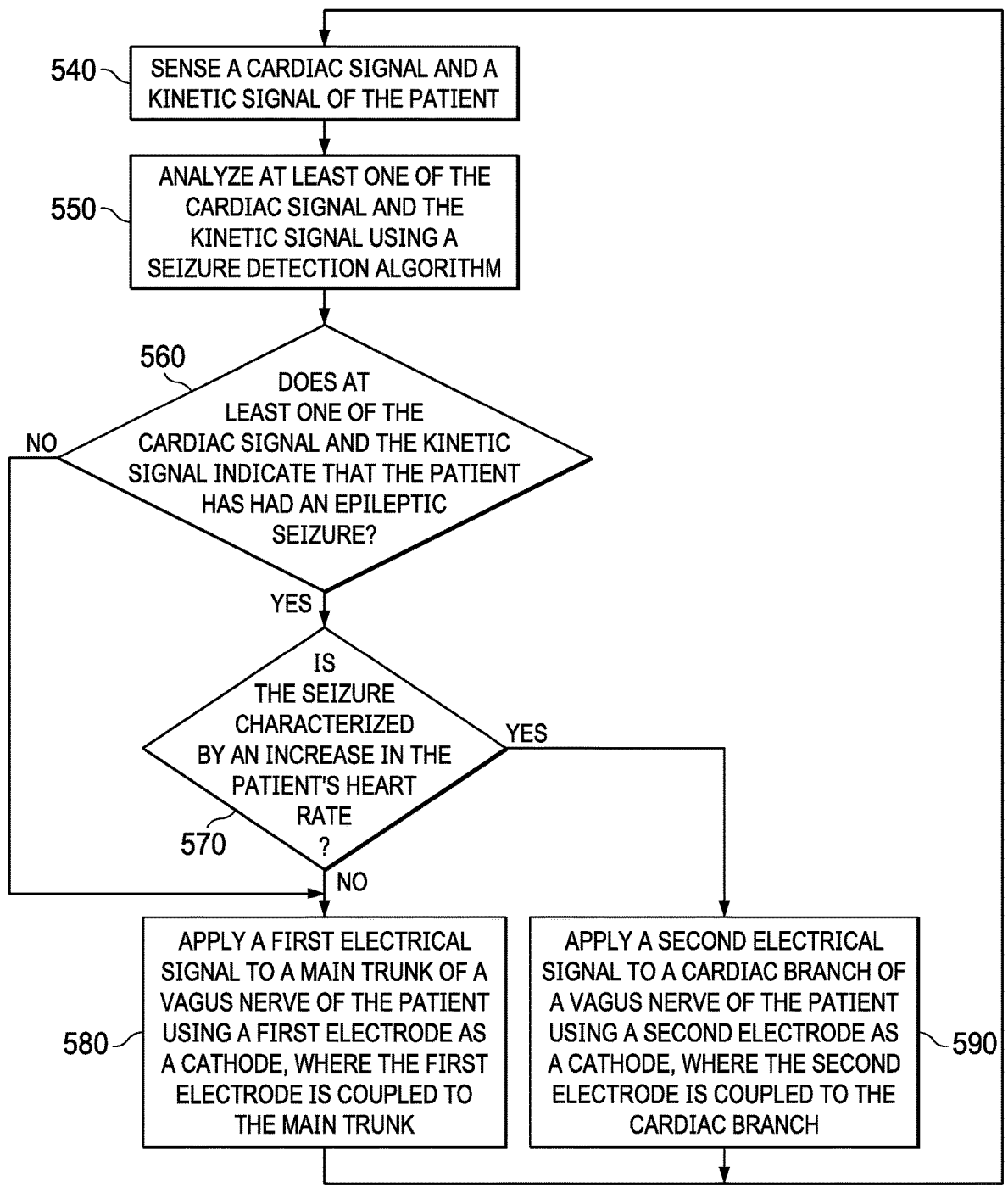
FIG. 5 illustrates a flowchart depiction of a method for providing first and second electrical signals to a main trunk and a cardiac branch of a vagus nerve, respectively, based upon whether or not at least one of a cardiac signal and a kinetic signal indicates that the patient is having and/or has had an epileptic seizure, and whether the seizure is characterized by an increase in heart rate, in accordance with an illustrative embodiment of the present disclosure.

FIG. 5 is a flow diagram of another method of treating a patient having epilepsy according to the present disclosure. A sensor is used to sense a cardiac signal and a kinetic signal of the patient (540). In a particular embodiment, the cardiac sensor may comprise an electrode pair for sensing an ECG (electrocardiogram) or heart beat signal, and the kinetic signal may comprise a triaxial accelerometer to detect motion of at least a portion of the patient's body. The method further comprises analyzing at least one of the cardiac signal and the kinetic signal using seizure detection algorithm (550), and the output of the algorithm is used to determine whether at least one of the cardiac signal and the kinetic signal indicate that the patient is having and/or has had an epileptic seizure (560).

If the patient is not having and/or has not had an epileptic seizure, the method comprises applying a first electrical signal to a main trunk of a vagus nerve of the patient using a first electrode, coupled to the main trunk, as a cathode (580). In one embodiment, the first electrical signal is an open-loop electrical signal having an on-time and off-time.

If the patient is having and/or has had an epileptic seizure, a determination is made whether the seizure is characterized by an increase in the patient's heart rate (570). If the seizure is not characterized by an increase in the patient's heart rate, the method comprises applying the first electrical signal to the main trunk of a vagus nerve using the first electrode as a cathode (580). In one embodiment, the cathode comprises an upper main trunk electrode 125-1 and the anode is selected from a cardiac branch electrode 125-2 and a lower main trunk electrode 125-3. Conversely, if the seizure is characterized by an increase in the patient's heart rate, the method comprises applying a second electrical signal to a cardiac branch of a vagus nerve of the patient using a second electrode, coupled to the cardiac branch, as a cathode (590). The anode is an upper main trunk electrode 125-1 or a lower main trunk electrode 125-3. In one embodiment, the method may comprise suspending the first electrical and applying the second electrical signal.

The method then continues the sensing of the cardiac and kinetic signals of the patient (540) and resumes the method as outlined in FIG. 5.

Figure 6:
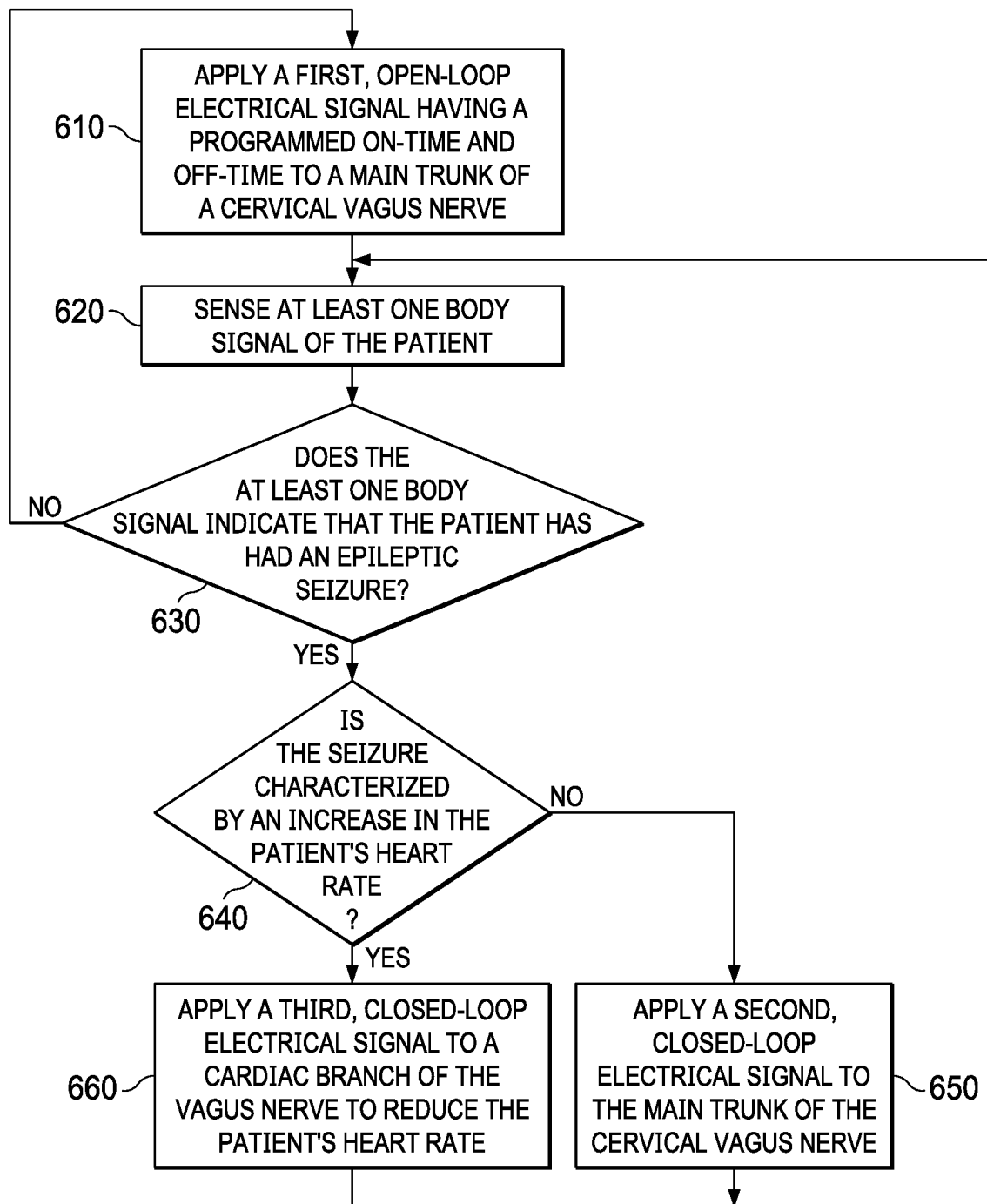
FIG. 6 illustrates a flowchart depiction of a method for providing a first, open-loop electrical signal to a main trunk of a vagus nerve, a second, closed-loop electrical signal to the main trunk of the vagus nerve based upon the patient having had an epileptic seizure not characterized by an increase in heart rate, and a third, closed-loop electrical signal to a cardiac branch of a vagus nerve based upon the patient having had an epileptic seizure characterized by an increase in heart rate, in accordance with an illustrative embodiment of the present disclosure.

FIG. 6 is a flow diagram of a further method of treating a patient having epilepsy according to the present disclosure. The method includes applying a first, open-loop electrical signal to a main trunk of a vagus nerve (610). The open-loop signal is characterized by an off-time in which electrical pulses are applied to the nerve, and an off-time in which electrical pulses are not applied to the nerve.

A sensor is used to sense at least one body signal of the patient (620), and a determination is made whether the at least one body signal indicates that the patient is having and/or has had an epileptic seizure (630). If the patient is not having and/or has not had a seizure, the method continues applying the first, open-loop electrical signal to a main trunk of a vagus nerve (610). If the patient is having and/or has had an epileptic seizure, a determination is made whether the seizure is characterized by an increase in the patient's heart rate (640). In one embodiment, the increase in heart rate is measured from a baseline heart rate existing prior to the seizure, e.g., a median heart rate for a prior period such as the 300 beats prior to the detection of the seizure event, or the 5 minutes prior to the detection of the seizure.

If the seizure is not characterized by an increase in the patient's heart rate, the method comprises applying a second, closed-loop electrical signal to the main trunk of the vagus nerve 650). In one embodiment, the second, closed-loop electrical signal is the same signal as the open-loop electrical signal, except that the second signal (as defined, e.g., by a current intensity, a pulse frequency, a pulse width and an on-time) is applied at a time different from the programmed timing of the first electrical signal. For example, if the first electrical signal comprises an on-time of 30 seconds and an off-time of 5 minutes, but a seizure is detected 1 minute after the end of a programmed on-time, the second electrical signal may comprise applying a 30 second pulse burst at the same current intensity, frequency, and pulse width as the first signal, but four minutes earlier than would have occurred absent the detected seizure. In another embodiment, the second, closed-loop electrical signal is a different signal than the first, open-loop electrical signal, and the method may also comprise suspending the first electrical before applying the second electrical signal. For example, the second, closed-loop electrical signal may comprise a higher current intensity, frequency, pulse width and/or on-time than the first, open-loop electrical signal, and may not comprise an off-time (e.g., the second electrical signal may be applied for a predetermined duration independent of the on-time of the first, open-loop electrical signal, such as a fixed duration of 1 minute, or may continue for as long as the body signal indicates the presence of the seizure event).

Returning to FIG. 6, if the seizure is characterized by an increase in the patient's heart rate, the method comprises applying a third, closed-loop electrical signal to a cardiac branch of a vagus nerve to reduce the patient's heart rate (660). The method may comprise suspending the first electrical as well as applying the third, closed-loop electrical signal. In one embodiment of the disclosure, each of the first, open-loop electrical signal, the second, closed-loop electrical signal, and the third, closed-loop electrical signal are applied unilaterally (i.e., to vagus nerve structures on the same side of the body) to the main trunk and cardiac branch of the vagus nerve. For example, the first, open-loop electrical signal and the second, closed-loop electrical signal may be applied to a left main trunk of the patient's cervical vagus nerve, and the third, closed-loop electrical signal may be applied to the left cardiac branch of the vagus nerve. Similarly, the first, second and third electrical signals may all be applied to the right vagus nerve of the patient. In alternative embodiments, one or more of the first, second and third electrical signals may be applied bilaterally, i.e., one of the first, second and third electrical signals is applied to a vagal structure on the opposite side of the body from the other two signals. For example, in a particular embodiment the first, open-loop signal and the second, closed-loop signal may be applied to a left main trunk of the patient's cervical vagus nerve, and the third, closed-loop electrical signal may be applied to a right cardiac branch of the patient's vagus nerve. Because the right cardiac branch modulates the sinoatrial node of the patient's heart, which is the heart's "natural pacemaker," the third electrical signal may have more pronounced effect in reducing the patient's heart rate if applied to the right cardiac branch.

After applying one of the second (650) and third (660) electrical signals to a vagus nerve of the patient, the method then continues sensing at least one body signal of the patient (620) and resumes the method as outlined in FIG. 6.

In the methods depicted in FIGS. 4-6, one or more of the parameters defining the first, second, and third electrical signals (e.g., number of pulses, pulse frequency, pulse width, On time, Off time, interpulse interval, number of pulses per burst, or interburst interval, among others) can be changed by a healthcare provided using a programmer 150.

Figure 7:
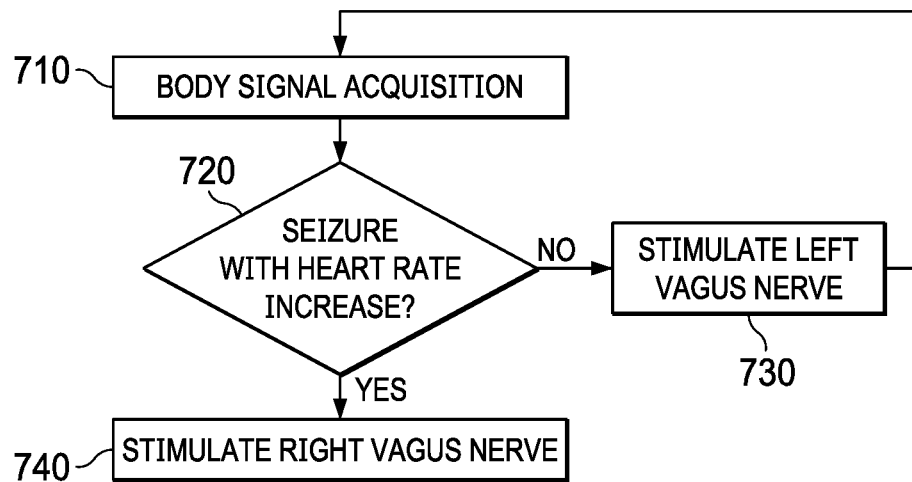
FIG. 7 is a flowchart depiction of a method for providing closed-loop vagus nerve stimulation for a patient with epilepsy by stimulating a right vagus nerve in response to detecting a seizure with tachycardia and stimulating a left vagus nerve in the absence of such a detection. For example if a recumbent person's heart rate is 55 bpm and it increases to 85 during a seizure, this is not clinical/pathological tachycardia, but may be considered tachycardia within the meaning of some embodiments of the present disclosure.

FIG. 7 is a flow diagram of a method of treating patients having seizures accompanied by increased heart rate. In one embodiment, tachycardia is defined as a neurogenic increase in heart rate, that is, an elevation in heart rate that occurs in the absence of motor activity or that if associated with motor activity, the magnitude of the increase in heart rate is larger than that caused by motor activity alone. In one embodiment, a body signal is acquired (710). The body signal may comprise one or more body signals that may be altered, changed or influenced by an epileptic seizure. As non-limiting examples, the body signal may comprise one or more of a cardiac signal such as heart rate, heart rate variability, or EKG complex morphology, a kinetic signal such as an accelerometer signal, a postural signal or body position signal), blood pressure, blood oxygen concentration, skin resistivity or conductivity, pupil dilation, eye movement, EEG, reaction time or other body signals. The body signal may be a real-time signal or a stored signal for delayed or later analysis. It may be acquired, for example, from a sensor element (e.g., coupled to a processor), from a storage device in which the signal data is stored.

The method further comprises determining whether or not the patient is having and/or has had a seizure accompanied by an increase in heart rate (720). In one embodiment, the method comprises a seizure detection algorithm that analyzes the acquired body signal data and determines whether or not a seizure has occurred. In a particular embodiment, the method comprises an algorithm that analyzes one or more of a cardiac signal, a kinetic signal, a cognitive signal, blood pressure, blood oxygen concentration, skin resistivity or conductivity, pupil dilation, and eye movement to identify changes in the one or more signals that indicate a seizure has occurred. The method may comprise an output signal or data flag that may be asserted or set when the detection algorithm determines from the body signal(s) that the patient is having and/or has had a seizure.

The method also comprises determining (720) whether or not the seizure is accompanied by an increase in heart rate. In one embodiment, the body data signal comprises a heart beat signal that may be analyzed to determine heart rate. In some embodiments, the heart beat signal may be used by the seizure detection algorithm to determine whether a seizure has occurred, while in other embodiments seizures are not detected using heart rate. Regardless of how the seizure is detected, however, the method of FIG. 7 comprises determining whether a detected seizure event is accompanied by an increase in heart rate. The increase may be determined in a variety of ways, such as by an increase in an instantaneous heart rate above a reference heart rate (which may be a predetermined interictal value such as 72 beats per minute (bpm), or a real-time measure of central tendency for a time window, such as a 5 minute median or moving average heart rate). Additional details about identifying increases in heart rate in the context of epileptic seizures are provided in U.S. Pat. Nos. 5,928,272, 6,341,236, 6,587,727, 6,671,556, 6,961,618, 6,920,357, 7,457,665, as well as U.S. patent application Ser. Nos. 12/770,562, 12/771,727, 12/771,783, 12/884,051, 12/886,419, 12/896,525, 13/098,262, and 13/288,886, each of which is hereby incorporated by reference in its entirety herein.

If the body data signal does not indicate that the patient is having and/or has had a seizure accompanied by tachycardia, the method comprises applying a first electrical signal to a left vagus nerve. If the body signal does indicate that the patient has experienced a seizure accompanied by tachycardia, the method comprises applying a second electrical signal to a right vagus nerve.

Without being bound by theory, it is believed that stimulation of the right vagus nerve, which enervates the right sinoatrial nerve that functions as the heart's natural pacemaker, will have a more prominent effect in slowing the heart rate than stimulation of the left vagus nerve. The present disclosure takes advantage of this electrical asymmetry of the left and right vagus nerves to minimize the effect of VNS on heart rate except where there is a need for acute intervention to slow the heart rate, i.e., when the patient has experienced and epileptic seizure, and the seizure is accompanied by an increase in heart rate. This may result in, for example, stimulation of the left vagus nerve either when there is no seizure (such as when an open-loop stimulation program off-time has elapsed and the program initiates stimulation in accordance with a programmed signal on-time), or when there is a detected seizure event that is not accompanied by an increase in heart rate (such as absence seizures); and stimulation of the right vagus nerve when there is a detected seizure event accompanied by a heart rate increase. In one embodiment, a programmed, open-loop electrical signal is applied to the left vagus nerve except when an algorithm analyzing the acquired body signal detects a seizure accompanied by a heart rate increase. In response to such a detection, a closed-loop electrical signal is applied to the right vagus nerve to slow the patient's (increased) heart rate. In some embodiments, the response to detecting a seizure accompanied by a heart rate increase may also include interrupting the application of the programmed-open-loop electrical signal to the left vagus nerve. The interrupted open-loop stimulation of the left vagus nerve may be resumed either when the seizure ends or the heart rate returns to a desired, lower heart rate.

In an additional embodiment of the disclosure, electrode pairs may be applied to each of the left and right vagus nerves of the patient, and used depending upon whether or not seizures accompanied by cardiac changes such as tachycardia are detected.

Figure 8:
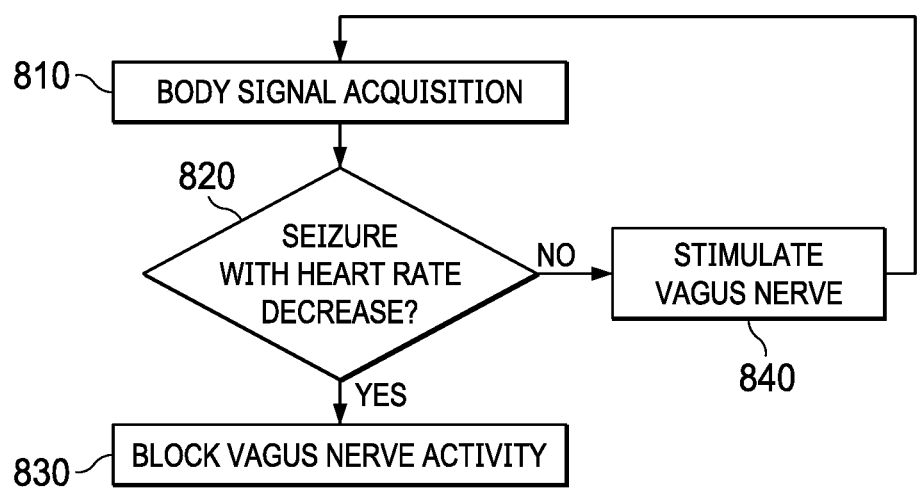
FIG. 8 is a flowchart depiction of a method for providing a closed-loop therapy to a vagus nerve of a patient with epilepsy in response to detecting a seizure associated with a heart rate decrease, wherein said therapy blocks impulse conduction along at least one vagus nerve.

FIG. 8 is a flowchart depiction of a method of treating patients having seizures accompanied by a relative or absolute decrease in heart rate (i.e., a bradycardia episode). Epileptic seizures originating from certain brain regions may trigger decreases in heart rate of a magnitude sufficient to cause loss of consciousness and of postural tone (i.e., syncope). In some subjects the cerebral ischemia associated with the bradycardia may in turn lead to convulsions (i.e., convulsive syncope). If bradycardia-inducing seizures are not controllable by medications, the current treatment is implantation of a demand cardiac pacemaker. In one embodiment of the present disclosure, ictal bradycardia may be treated by preventing vagal nerve impulses from reaching the heart, either by preventing impulses traveling through all fiber types contained in the trunk of the nerve or in one of its branches, or by only blocking impulses within a certain fiber type. In another embodiment, the degree of the nerve impulse blocking within a vagus nerve may be determined based upon the magnitude of bradycardia (e.g., the larger the bradycardia change from the pre-existing baseline heart rate, the larger the magnitude of the block) so as to prevent tachycardia from occurring.

In one embodiment, a body signal is acquired (810). The body signal may comprise one or more body signals that may be altered, changed or influenced by an epileptic seizure. Changes in the body signal may be used to detect the onset or impending onset of seizures. As noted with reference to FIG. 7, the body signal may comprise one or more measure derived from a cardiac signal (e.g., heart rate, heart rate variability, change in EKG morphology), a kinetic signal (e.g., an accelerometer, force of muscle contraction, posture or body position signal), blood pressure, blood oxygen concentration, skin resistivity/conductivity, pupil dilation, eye movement, or other body signals. The body signal may be a real-time signal, a near-real-time signal, or a non-real-time signal, although in preferred embodiments, the signal is a real-time signal or a near-real-time signal. The signal may be acquired from a sensor element (e.g., coupled to a processor) or from a storage device.

Referring again to FIG. 8, the method further comprises determining whether or not the patient is having and/or has had a seizure that is accompanied by a decrease in heart rate (820). In one embodiment, the method comprises using a seizure detection algorithm using one or more of a cardiac, kinetic, neurologic, endocrine, metabolic or tissue stress marker to detect seizures, and to determine if the seizure is associated with a decrease in heart rate. In a particular embodiment, an algorithm—which may comprise software and/or firmware running in a processor in a medical device—analyzes one or more of a cardiac signal, a kinetic signal, blood pressure, blood oxygen concentration, skin resistivity or conductivity, pupil dilation, and eye movement to identify changes in the one or more signals that indicate the occurrence of an epileptic seizure. Such changes may be identified by determining one or more indices from the foregoing signals, such as a cardiac index (e.g., a heart rate), a kinetic index (e.g., a kinetic level or motion type, a magnitude of an acceleration or force, or other indices that may be calculated from an accelerometer signal). The method may include providing an output signal or setting a data flag when the detection algorithm determines from the body signal(s) that the patient is having and/or has had a seizure. In a preferred embodiment, the seizure detection occurs in real time and the output signal or data flag is set immediately upon detection of the seizure.

Once it is determined that the patient is having and/or has had a seizure, the method also comprises determining if the seizure is accompanied by a decrease in heart rate. In one embodiment, the acquired body data signal (810) comprises a heart beat signal that may be analyzed to determine heart rate. In some embodiments, the acquired heart beat signal may be used by the seizure detection algorithm to determine whether a seizure has occurred, while in other embodiments seizures are determined without regard to the patient's heart rate. Regardless of how the seizure is determined, the method of FIG. 8 comprises determining whether a detected seizure event is accompanied by a decrease in heart rate (820). The decrease in heart rate may be determined in a variety of ways, such as by a decrease in an instantaneous heart rate below a reference heart rate value (which may be a predetermined interictal value such as 72 beats per minute (bpm), or a real-time measure of central tendency for a time window or number-of-beats window (e.g., a 5 minute median or moving average heart rate, or a media heart rate for a window selected from 3-300 beats such as a 5, 10, or 300 beat window)). Additional details about identifying decreases in heart rate in the context of epileptic seizures are provided in U.S. patent application Ser. Nos. 12/770,562, 12/771,727, 12/771,783, 12/884,051, 12/886,419, 13/091,033, each of which is hereby incorporated by reference in its entirety herein.

In one embodiment, if the acquired body data signal does not indicate that the patient is having and/or has had a seizure accompanied by a HR decrease, the method comprises applying a first electrical signal to a vagus nerve (840), wherein the first electrical signal is sufficient to generate exogenous action potentials in fibers of the vagus nerve. The second electrical signal is a therapeutic electrical signal to treat the seizure. It may be applied to either the left or right vagus nerves, or both. The first electrical signal may be a signal defined by, among other parameters, an on-time during which electrical pulses are applied to the nerve, and an off-time during which no pulses are applied to the nerve. In some embodiments, the on-time may be determined by the duration and intensity of the change in heart rate, while in other embodiments it may be pre-programmed Cathode(s) and anode(s) may be placed on the nerve trunks or branches to maximize flow of exogenously generated nerve impulses in a caudal direction (for control of heart rate changes) and a cephalic direction for seizure treatment.

If the body signal indicates that the patient is having and/or has had a seizure accompanied by a decrease in heart rate, the method comprises applying an action to decrease vagal/parasympathetic tone. In one embodiment, the method comprises blocking the passage of impulses through at least one of a vagus nerve trunk or branch. This may be accomplished by applying one or more of a second electrical signal (e.g., a high frequency electrical signal), a thermal signal (e.g., cooling), a chemical signal (e.g., applying a local anesthetic), and/or a mechanical signal (e.g., applying pressure or a vibration) to a vagus nerve of the patient (830). In another embodiment, the method comprises delivering at least one of an anti-cholinergic drug or a sympatho-mimetic drug.

As used herein, blocking vagus nerve activity means blocking intrinsic or native vagal activity (i.e., blocking action potentials not artificially or exogenously induced by an electrical signal generated by a device). The blocking signal may block the conduction of action potentials in all or at least some portion or fraction of the axons of a vagus nerve. In general, such blocking signals are incapable of inducing exogenous action potentials in the axons of the vagus nerve. In one embodiment, the blocking signal may comprise a high frequency, pulsed electrical signal, the pulse frequency being sufficient to inhibit propagation of at least some action potentials in vagus nerve fibers. The electrical signal may comprise a signal in excess of 300 Hz, or other frequency, so long as the frequency and other stimulation signal parameters (such as pulse width and pulse current or voltage) provide a signal capable of inhibiting some or all of the action potentials propagating along fibers of the vagus nerve. In alternative embodiments, the electrical signal may comprise generating unidirectional action potentials for collision blocking of endogenous action potentials.

High frequency vagus nerve stimulation (or other blocking signals such as collision blocking) may inhibit pathological vagus nerve activity associated with the seizure that may be acting to slow the patient's heart rate. By providing such stimulation only when the patient experiences a seizure accompanied by a reduced heart rate (e.g., bradycardia), a therapy may be provided that acts to maintain the patient's heart rate when the patient experiences a seizure involving excessive vagal activity—and consequent undesired slowing of—the heart. In one embodiment, the blocking electrical signal (830) is provided to a right vagus nerve. Without being bound by theory, because the right vagus nerve innervates the right sinoatrial node that functions as the heart's natural pacemaker, it is believed that right-side VNS will have a more significant effect upon the heart rate than stimulation of the left vagus nerve. In alternative embodiments, the blocking signal may be applied to the left vagus nerve, to both the right and left vagus nerves, or to one or both of the left and right cardiac branches of the vagus nerves.

In one embodiment, the method comprises applying a first electrical signal that may be a conventional vagus nerve stimulation signal defined by a plurality of parameters (e.g., a pulse width, a current magnitude, a pulse frequency, an on-time and an off-time). A seizure detection algorithm (e.g., using one or more of a cardiac, kinetic, metabolic, EEG, or other body signal) may be used to detect seizures, and the patient's heart rate may be determined proximate the seizure detection to determine if the seizure is accompanied by a decrease in the patient's heart rate. If the seizure is accompanied by a slowing of the patient's heart rate, the first electrical signal may be suspended, and a second electrical signal may be applied to slow the patient's heart rate. The method may further include sensing the patient's heart rate during or after application of the second electrical signal. In one embodiment, the second electrical signal may be modified (e.g., by changing current magnitude, pulse width, or pulse frequency), or suspended (and possibly resumed) to maintain the patient's heart rate between an upper heart rate threshold and a lower heart rate threshold. In some embodiments, the upper and lower heart rate thresholds may be dynamically set (e.g., as no more than 5 bpm above or below the baseline HR prior to the seizure detection).

Figure 9:
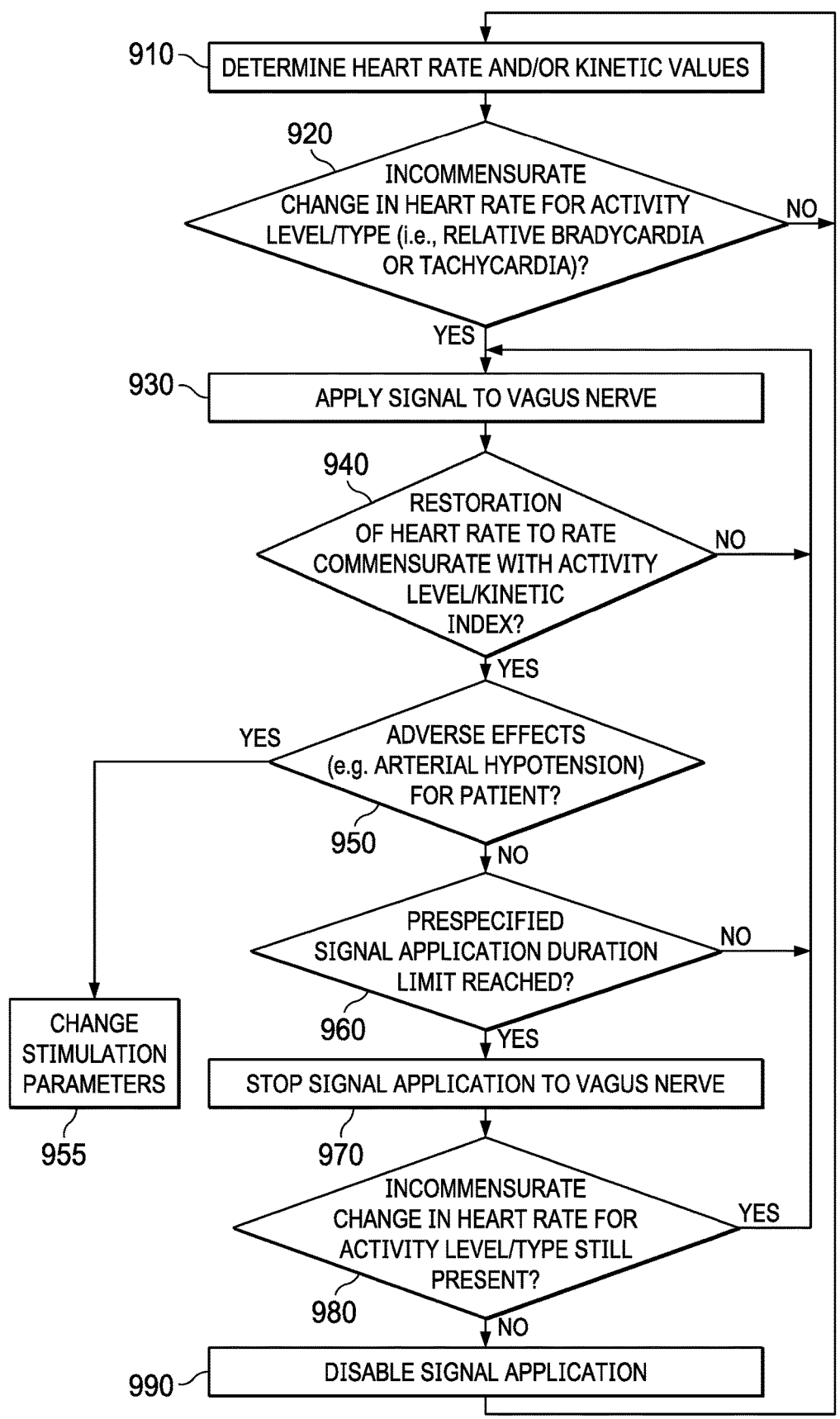
FIG. 9 is a flowchart depicting a method for providing closed-loop vagus nerve stimulation based on an assessment of whether the patient's heart rate is commensurate with the patient's activity level or activity type.

FIG. 9 is a flow diagram of a method of treating a patient with epilepsy by providing closed-loop vagus nerve intervention (e.g., stimulation or blockage of impulse conduction) to maintain the patient's heart rate within a range that is both safe and also commensurate with the activity type or level and state of the patient (e.g., as determined from a kinetic signal from a sensing element such as a triaxial accelerometer or by measuring oxygen consumption). In one embodiment, the method comprises providing vagus nerve stimulation in response to determining that a heart rate is incommensurate with the kinetic signal of the patient, to restore cardiac function to a rate that is commensurate with the patient's kinetic signal. In one embodiment, the stimulation may comprise stimulating a right vagus nerve to slow the patient's heart rate to a level that is safe and/or commensurate with activity level. In another embodiment, the stimulation may comprise providing a blocking signal to increase a slow heart rate to a rate that is safe and/or commensurate with the activity level. Pharmacologic compounds (e.g., drugs) with sympathetic or parasympathetic effects (e.g., enhancing or blocking sympathetic or parasympathetic activity) may be used to restore heart rate to a rate commensurate with kinetic activity of the patient in still other embodiments. In one embodiment, the method involves determining a heart rate and one or more kinetic or metabolic (e.g., oxygen consumption) indices for the patient (910). Heart rate may be determined from an acquired cardiac signal (e.g., from a sensor or stored data). Kinetic and/or metabolic indices may likewise be determined from a kinetic sensor (e.g., an accelerometer, a positional sensor, a GPS device coupled to a clock, or a postural sensor), a metabolic sensor, or from stored data. Sensor data may be subjected to one or more operations such as amplifying, filtering, A/D conversion, and/or other pre-processing and processing operations to enable determination of heart rate (and in some embodiments other cardiac indices such as heart rate variability) and kinetic indices.

The activity level of the patient may be determined from multiple kinetic indications such as an activity level, a type of activity, a posture, a body position, a trunk or limb acceleration or force, or a duration of one of the foregoing, and may be adapted or modified as a function of age, gender, body mass index, fitness level or time of day or other indices of the patient's condition or environment. For example, the kinetic signal may be processed to provide indices that indicate moderate ambulatory motion for an upright patient, vigorous physical exercise (in which the patient may be upright as in running or in a prone position as in some calisthenics exercises), a fall (e.g., associated with a seizure), reclining, resting or sleeping, among other activity levels and kinetic states.

The one or more kinetic indices may then be used to determine (e.g., by retrieving stored data from a lookup table or by calculation using an algorithm) one or more heart rate ranges or values that would be commensurate with the kinetic activity and/or kinetic state, duration, time of day, etc. associated with the indices. In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

Returning to FIG. 9, the determined heart rate may be compared to the range(s)/value(s) identified as commensurate with the kinetic indices (920) at a given time point. If the actual heart rate of the patient is within the expected/commensurate range or value associated with the kinetic or metabolic indices at the time point, or is within a specified proximity of a particular range or value, no action may be taken, and the method may involve continuing to analyze the patient's cardiac and kinetic signals or metabolic signals. On the other hand, if the heart rate is outside the expected value or range of values for the kinetic or metabolic indices for that time point, then the heart rate is not commensurate with the kinetic signal of the patient, and a therapy may be provided to the patient by applying one of an electrical, thermal, mechanical or chemical signal to a vagus nerve of the patient (930) or administering to the patient (e.g., intravenously, through mucosae) a drug with cholinergic or anti-cholinergic or adrenergic actions, depending on the case or situation. In one embodiment, the method may comprise applying the signal to a main trunk of a vagus nerve of the patient, and in another embodiment, the signal may be applied to a cardiac branch of a vagus nerve.

In one embodiment, the heart rate of the patient may be higher than a value commensurate with the activity level or kinetic indices of the patient. In this case, the patient is having relative tachycardia. Where this is the case, as previously noted, vagus nerve stimulation may be applied to one or more of a right cardiac branch, left cardiac branch, or right main trunk of the patient's vagus nerve to reduce the patient's heart rate to a rate that is commensurate with the activity level. Embodiments of the disclosure may be used to treat epileptic seizures associated with tachycardia, and other medical conditions associated with tachycardia given the patient's activity level. Therapies (e.g., electrical, chemical, mechanical, thermal) delivered to a patient via the vagus nerves may be employed for tachyarrythmias, angina pectoris or pain in regions innervated by a vagus nerve.

In another embodiment, the patient's heart rate may be lower than a value commensurate with the patient's activity level or kinetic indices, that is, the patient is having relative or absolute bradycardia. High frequency (>>300 Hz) electrical pulses may be applied to the left or right vagus nerves (e.g., a main trunk of the right and/or left vagus nerves or to their cardiac branches) to block propagation of transmission of nerve impulses through their fibers. High-frequency VNS may be applied to block impulses traveling to the heart to abate neurogenic, cardiogenic or iatrogenic bradycardia, or to minimize the cumulative effects on the heart's conduction system and myocardium of epileptic seizures, especially in status epilepticus. Selective blockage of impulses traveling through a vagus nerve to the heart may be accomplished with electrical stimulation to treat adverse cardiac effects associated with disorders such as epilepsy, depression, diabetes or obesity. By blocking vagus nerve conduction to the heart, when the patient's heart rate is incommensurate with the activity level or kinetic indices, a therapy may be provided to revert the change in heart rate (whether the change involves bradycardia or tachycardia). In one embodiment, an electrical signal generator may be used to apply a first therapy signal to a vagus nerve of the patient, and an electrical signal generator (which may be the same or a different electrical signal generator) may apply a vagus nerve conduction blocking electrical signal to a vagus nerve (e.g., a cardiac branch of the vagus nerve) to block cardiac effects that would result from the first electrical signal, absent the vagus nerve conduction blocking electrical signal.

Referring again to FIG. 9, the method may comprise determining the patient's heart rate in response the therapy to determine whether the heart rate has been restored to a rate that is with commensurate with the patient's activity level/kinetic index (940). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (950). Adverse events may include, without limitation, side effects such as voice alteration, pain, difficulty breathing or other respiratory effects, adverse cardiac effects such as bradycardia (following a determination of relative tachycardia in step 920), tachycardia (following a determination of bradycardia in step 920), and alteration in blood pressure or gastro-intestinal activity.

If an adverse event has occurred, the method may involve changing one or more stimulation parameters to eliminate, reduce or ameliorate the adverse event (955). If no adverse event has occurred, the method may comprise continuing to apply a signal the vagus nerve until a predetermined signal application duration has been reached (960), at which time the signal application may be stopped (970). The method may further comprise determining, after the therapy has been stopped, if the patient's heart rate remains incommensurate with the patient's activity level or type (980), in which case the signal application may be resumed or other appropriate action may be taken (e.g., local or remote alarms or alerts, notification of caregivers/healthcare providers, etc.). If the heart rate has returned to a value that is commensurate or appropriate for the patient's activity level, the signal application may be discontinued (990).

Figure 10:
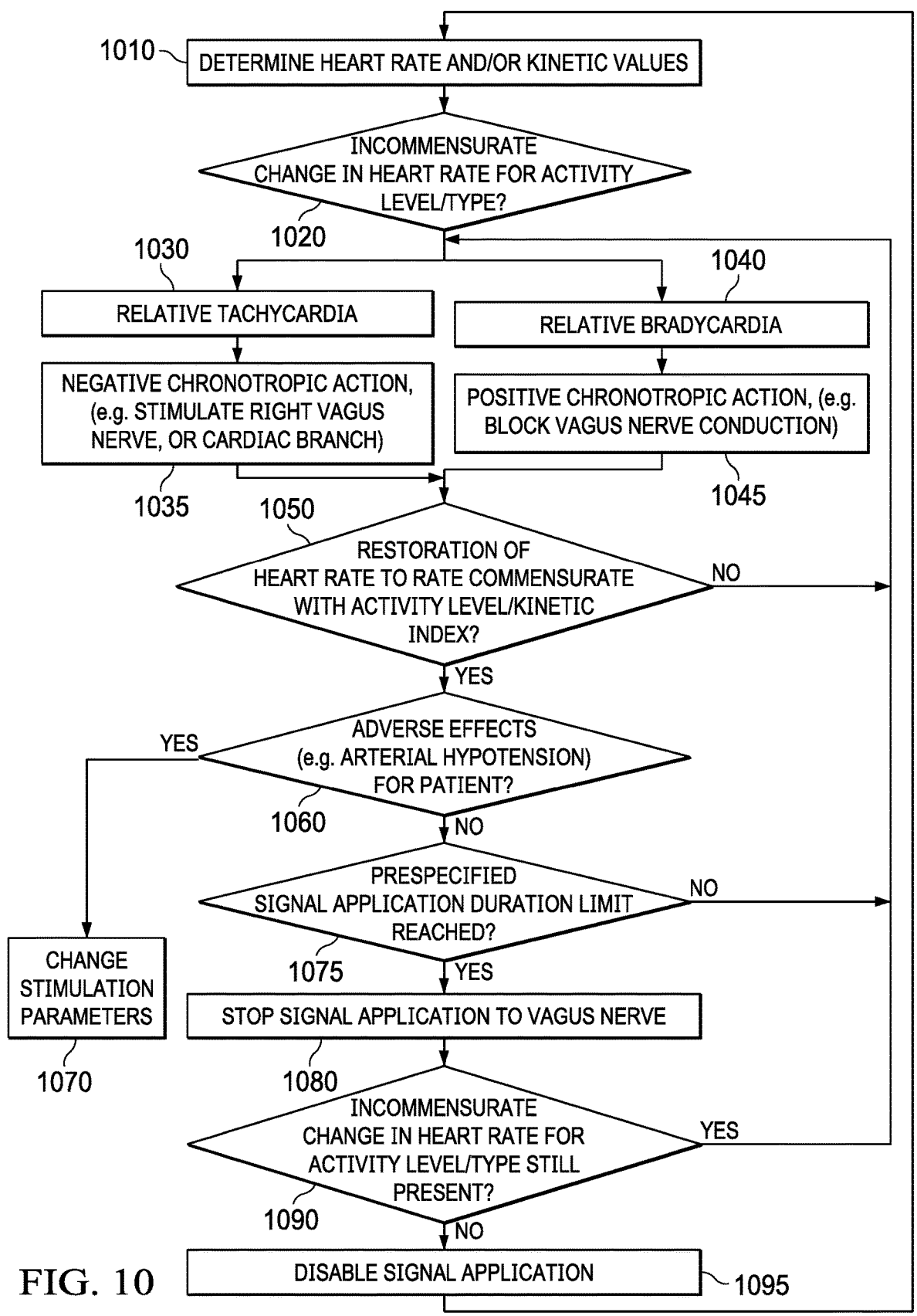
FIG. 10 is a flowchart depicting a method for providing closed-loop vagus nerve stimulation based on a determination that the patient's heart rate is incommensurate with the patient's activity level or activity type, and further in view of whether the incommensurate changes involves relative tachycardia or relative bradycardia.

FIG. 10 is a flow diagram of a method of treating a patient to with epilepsy by providing closed-loop vagus nerve stimulation to treat relative tachycardia or relative bradycardia by restoring the patient's heart rate to a rate that is commensurate with the activity type or level of the patient (e.g., as determined from a kinetic signal from a sensing element such as a triaxial accelerometer or by measuring oxygen consumption). In one embodiment, the method comprises identifying instances of relative tachycardia or relative bradycardia and responding with negative or positive chronotropic actions to restore the heart rate to a level commensurate with the patient's activity type or level.

In one embodiment, the method involves determining a heart rate and an activity type or level for the patient (1010). The patient's heart rate may be determined from an acquired cardiac signal or from stored data. The activity level or type of the patient may be determined from one or more sensor or from stored data. Sensors may include, for example, accelerometers, positional sensors, GPS devices coupled to a clock, postural sensors, and metabolic sensors. Sensor data may be subject to conventional signal processing, and may in addition be adapted or modified as a function of age, gender, body mass index, fitness level or time of day or other indices of the patient's condition or environment.

The patient's activity type or level may then be used to determine one or more heart rate ranges or values that are commensurate with the activity type or level (1020). In some embodiments, heart rate ranges may be established for particular levels or types of activity (e.g., running, walking), that may be adaptively adjusted depending upon various factors such as the duration of the activity, the patient's fitness level, the time of day, a level of fatigue, an environmental temperature, etc. A commensurate heart rate is one that is within expected ranges or values for the person's effort, and for factors inherent to the patient and the environment.

If the heart rate is commensurate with the activity level, in one embodiment no action may be taken, and the method may involve continuing to analyze the patient's cardiac and activity. On the other hand, if the heart rate is outside the identified value or range of values appropriate for the patient's activity type or level then the heart rate is not commensurate with the kinetic signal of the patient. Where this is the case, the method may further comprise determining whether the patient is experiencing relative tachycardia or is experiencing relative bradycardia (1030, 1040).

Where the heart rate of the patient is higher than a value commensurate with the activity level or type, the patient is experiencing relative tachycardia (1030), and the method may comprise initiating a negative chronotropic action (1035) to slow the heart rate to a rate that is commensurate with the activity level or type. In one embodiment, this may involve applying stimulation to one or more of a left or right main vagal trunk or cardiac branch of the patient. In other embodiments, the method may comprise providing a drug to enhance the parasympathetic tone of the patient. In still other embodiments, the method may comprise reducing the patient's sympathetic tone, such as by applying high-frequency stimulation to a sympathetic nerve trunk or ganglion or administering an anti-cholinergic drug. Negative chronotropic actions may be used to treat epileptic seizures associated with tachycardia, and other medical conditions associated with relative tachycardia given the patient's activity level.

Where the heart rate of the patient is lower than a value commensurate with the activity level or type, the patient is experiencing relative bradycardia (1040), and the method may comprise initiating a positive chronotropic action (1045) to increase the heart rate to a rate that is commensurate with the activity level or type. In one embodiment, this may involve applying high-frequency (>>300 Hz) electrical stimulation to one or more of a left or right main vagal trunk or cardiac branch of the patient to reduce the transmission of intrinsic vagus nerve action potentials in at least some vagal fibers. In other embodiments, the method may comprise providing a drug to reduce the parasympathetic tone of the patient. In still other embodiments, the method may comprise increasing the patient's sympathetic tone, such as by applying electrical signals to a sympathetic nerve trunk or ganglion or by administering a sympatho-mimetic drug. Positive chronotropic actions may be used to treat epileptic seizures associated with bradycardia, and other medical conditions associated with relative bradycardia given the patient's activity level.

The method may further comprise, after initiating the negative or positive chronotropic action, determining whether the patient's heart rate has been restored to a rate that is with commensurate with the patient's activity level/kinetic index (1050). If not, then the therapy (e.g., VNS to reduce or increase heart rate to an appropriate value) may be continued, with or without parameter modification, or re-initiated after a delay period or confirmation period.

If the heart rate has returned to a range/value commensurate with the activity level of the patient, the method may, in some embodiments, further involve determining whether or not an adverse event has occurred (1060). Adverse events may include, without limitation, side effects such as voice alteration, pain, difficulty breathing or other respiratory effects, adverse cardiac effects such as bradycardia (following a determination of relative tachycardia in step 1030), or tachycardia (following a determination of bradycardia in step 1040), and alteration in blood pressure or gastric activity.

If an adverse event has occurred, the method may involve changing one or more stimulation parameters to eliminate, reduce or ameliorate the adverse event (1070). If no adverse event has occurred, the method may comprise continuing to stimulate the vagus nerve (or a chemical, thermal or mechanical therapy) until a predetermined stimulation duration has been reached (1075), at which time the stimulation may be stopped (1080). The method may further comprise determining, after the therapy has been stopped, if the patient's heart rate remains incommensurate with the patient's activity level or type (1090), in which case the stimulation may be resumed or other appropriate action may be taken (e.g., local or remote alarms or alerts, notification of caregivers/healthcare providers, use of other forms of therapy, etc.). If the heart rate has returned to a value that is commensurate or appropriate for the patient's activity level, the stimulation may be discontinued (1095).

Additional embodiments consistent with the foregoing description and figures may be made. Non-limiting examples of some such embodiments are provided in the numbered paragraphs below.

100. A method of controlling a heart rate of an epilepsy patient comprising:
sensing at least one of a kinetic signal and a metabolic signal of the patient;
analyzing the at least one of a kinetic and a metabolic signal to determine at least one of a kinetic index and a metabolic index;
receiving a cardiac signal of the patient;
analyzing the cardiac signal to determine the patient's heart rate;
determining if the patient's heart rate is commensurate with the at least one of a kinetic index and a metabolic index; and
applying an electrical signal to a vagus nerve of the patient based on a determination that the patient's heart rate is not commensurate with the at least one of a kinetic signal and a metabolic signal of the patient.

101. The method of numbered paragraph 100, wherein determining at least one of a kinetic index and a metabolic index comprises determining at least one of an activity level or an activity type of the patient based on the at least one of a kinetic index and a metabolic index, and wherein determining if the patient's heart rate is commensurate with the at least one of a kinetic index and a metabolic index of the patient comprises determining if the heart rate is commensurate with the at least one of an activity level or an activity type.

102. The method of numbered paragraph 101, wherein determining if the patient's heart rate is commensurate with the at least one of a kinetic index and a metabolic index comprises determining if the patient's heart rate is above or below a rate that is commensurate with the one or more of a kinetic index and a metabolic index.

103. A method of treating a patient having epilepsy comprising
sensing at least one body signal of the patient;
determining whether or not the patient is having or has had an epileptic seizure based on the at least one body signal;
sensing a cardiac signal of the patient;
determining whether or not the seizure is associated with a change in the patient's cardiac signal;
applying a first therapy to a vagus nerve of the patient based on a determination that the patient is having or has had an epileptic seizure that is not associated with a change in the patient's cardiac signal, wherein the first therapy is selected from an electrical, chemical, mechanical, or thermal signal; and
applying a second therapy to a vagus nerve of the patient based on a determination that the patient is having or has had an epileptic seizure associated with a change in the patient's cardiac signal, wherein the second therapy is selected from an electrical, chemical, mechanical (e.g., pressure) or thermal signal.

104. The method of numbered paragraph 103, further comprising applying a third therapy to a vagus nerve of the patient based a determination that the patient is not having or has not had an epileptic seizure, wherein the third therapy is selected from an electrical, chemical, mechanical or thermal signal.

105. A method of treating a patient having epilepsy comprising: coupling a first set of electrodes to a main trunk of the left vagus nerve of the patient; coupling a second set of electrodes to a main trunk of the right vagus nerve of the patient; providing an electrical signal generator coupled to the first electrode set and the second electrode set; receiving at least one body data stream;
analyzing the at least one body data stream using a seizure detection algorithm to determine whether or not the patient is having and/or has had an epileptic seizure;
applying a first electrical signal from the electrical signal generator to the main trunk of the left vagus nerve, based on a determination that the patient is having and/or has had an epileptic seizure without a heart rate change; and
applying a second electrical signal from the electrical signal generator to the main trunk of the right vagus nerve, based on a determination that the patient is having or has had an epileptic seizure with a heart rate change.

106. A method of treating a patient having epilepsy comprising:
receiving at least one body data stream;
analyzing the at least one body data stream using a seizure detection algorithm to detect whether or not the patient has had an epileptic seizure;
receiving a cardiac signal of the patient;
analyzing the cardiac signal to determine a first cardiac feature;
applying a first electrical signal to a vagus nerve of the patient, based on a determination that the patient has not had an epileptic seizure characterized by a change in the first cardiac feature, wherein the first electrical signal is not a vagus nerve conduction blocking electrical signal; and
applying a second electrical signal to a vagus nerve of the patient, based on a determination that the patient has had an epileptic seizure characterized by a change in the cardiac feature, wherein the second electrical signal is a pulsed electrical signal that blocks action potential conduction in the vagus nerve.

107. A method of treating a patient having epilepsy comprising:
receiving at least one body data stream;
analyzing the at least one body data stream using a seizure detection algorithm to detect whether or not the patient has had an epileptic seizure;
receiving a cardiac signal of the patient;
analyzing the cardiac signal to determine a first cardiac feature;
applying a first electrical signal to a vagus nerve of the patient, based on a determination that the patient has not had an epileptic seizure characterized by a change in the first cardiac feature, wherein the first electrical signal is a pulsed electrical signal that blocks action potential conduction in the vagus nerve; and
applying a second electrical signal to a vagus nerve of the patient, based on a determination that the patient has had an epileptic seizure characterized by a change in the cardiac feature, wherein the second electrical signal is not a vagus nerve conduction blocking electrical signal.

Figure 11:
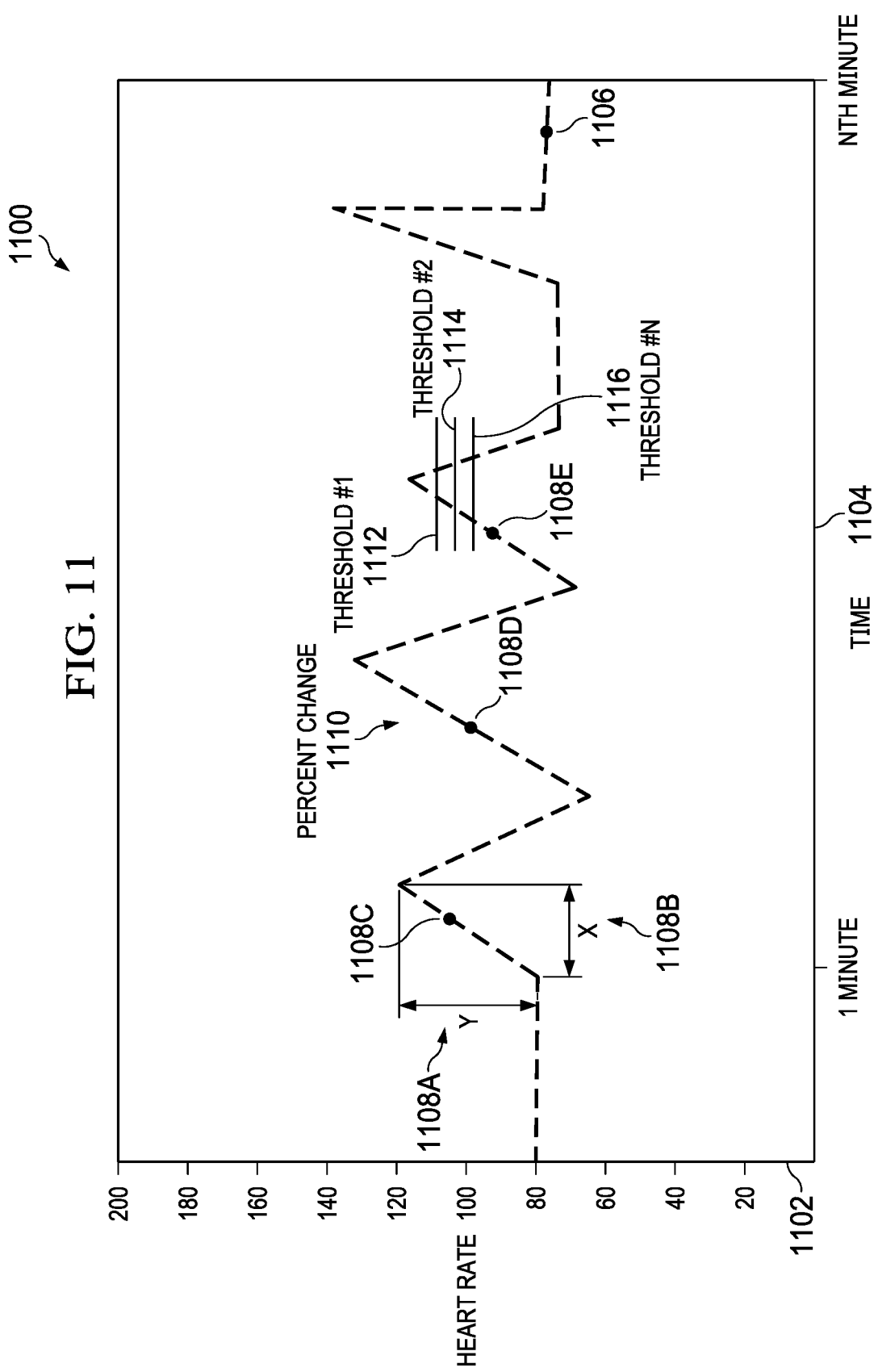
FIG. 11 is a graph of heart rate versus time, according to one embodiment.

In FIG. 11, a graph of heart rate versus time is shown, according to one embodiment. A first graph 1100 includes a y-axis 1102 which represents heart rate where the heart rate goes from a zero value to an Nth value (e.g., 200 heart beats, etc.). Further, the first graph 1100 includes an x-axis 1104 which represents time from 1 minute to Nth minutes (and/or 0.001 seconds to Nth seconds). In this example, a first heart rate versus time line 1106 for the patient is shown. In this example, the patient's heart rate goes from 80 heart beats per minute to 118 heart beats per minute with a first rise 1108A and a first run 1108B during a first event 1108C. In addition, the patient's heart rate goes from 70 heart beats per minute to 122 heart beats per minute during a second event 1108D which has a first percentage change 1110 associated with the second event 1108D. Further, the patient's heart rate goes from 70 beats per minute to 113 beats per minute during an nth event 1108E which surpasses a first threshold amount 1112, and/or a second threshold amount 1114, and/or an Nth threshold amount 1116. In one example, only the Nth threshold amount 1116 needs to be reached to trigger a therapy and/or an alert. In another example, only the second threshold amount 1114 needs to be reached to trigger a therapy and/or an alert. In another example, only the first threshold 1112 needs to be reached to trigger a therapy and/or an alert. In another example, both the Nth threshold 1116 and the second threshold 1114 need to reached to trigger a therapy and/or an alert. In another example, all of the Nth threshold 1116, the second threshold 1114 and the first threshold 1112 need to reached to trigger a therapy and/or an alert. In one example, only the Nth threshold amount 1116 needs to be reached during a specific time period to trigger a therapy and/or an alert. In another example, only the second threshold amount 1114 needs to be reached during a specific time period to trigger a therapy and/or an alert. In another example, only the first threshold 1112 needs to be reached during a specific time period to trigger a therapy and/or an alert. In another example, both the Nth threshold 1116 and the second threshold 1114 need to reached during a specific time period to trigger a therapy and/or an alert. In another example, all of the Nth threshold 1116, the second threshold 1114 and the first threshold 1112 need to reached during a specific time period to trigger a therapy and/or an alert. In these examples, one or more triggering events may occur based on a determination of the rise and run of a change in heart rate, a percentage change in heart rate, a threshold amount being reached or exceeded (or within any percentage of the threshold), and/or any combination thereof. A triggering event may initiate one or more actions to increase and/or decrease the patient's heart rate. For example, if the patient's heart rate is increasing which determines the triggering event, then the system, device, and/or method may initiate one or more actions to decrease the heart rate of the patient to help reduce, dampen, eliminate, and/or buffer the increase in the patient's heart rate. Further, the system, device, and/or method may oscillate between decreasing the patient's heart rate and increasing the patient's heart rate depending on any changes to the patient's heart rate. For example, the system, device, and/or method may initiate one or more actions to decrease a patient's heart rate based on the patient's heart rate going from 80 heart beats per minute to 130 heart beats per minute which results in the patient's heart rate falling from 130 heart beats per minute to 65 heart beats per minute in a first time period. Based on the change in the heart rate from 130 heart beats per minute to 65 heart beats per minute in the first time period, the system, device, and/or method may initiate one or more actions to increase the patient's heart rate and/or stabilize the patient's heart rate. In another example, the system, method, and/or device may stop and/or modify any initiated action based on one or more feedback signals. In addition, one or more warnings may be transmitted to the patient, a caregiver, a doctor, a medical professional, and/or logged.

Figure 12:
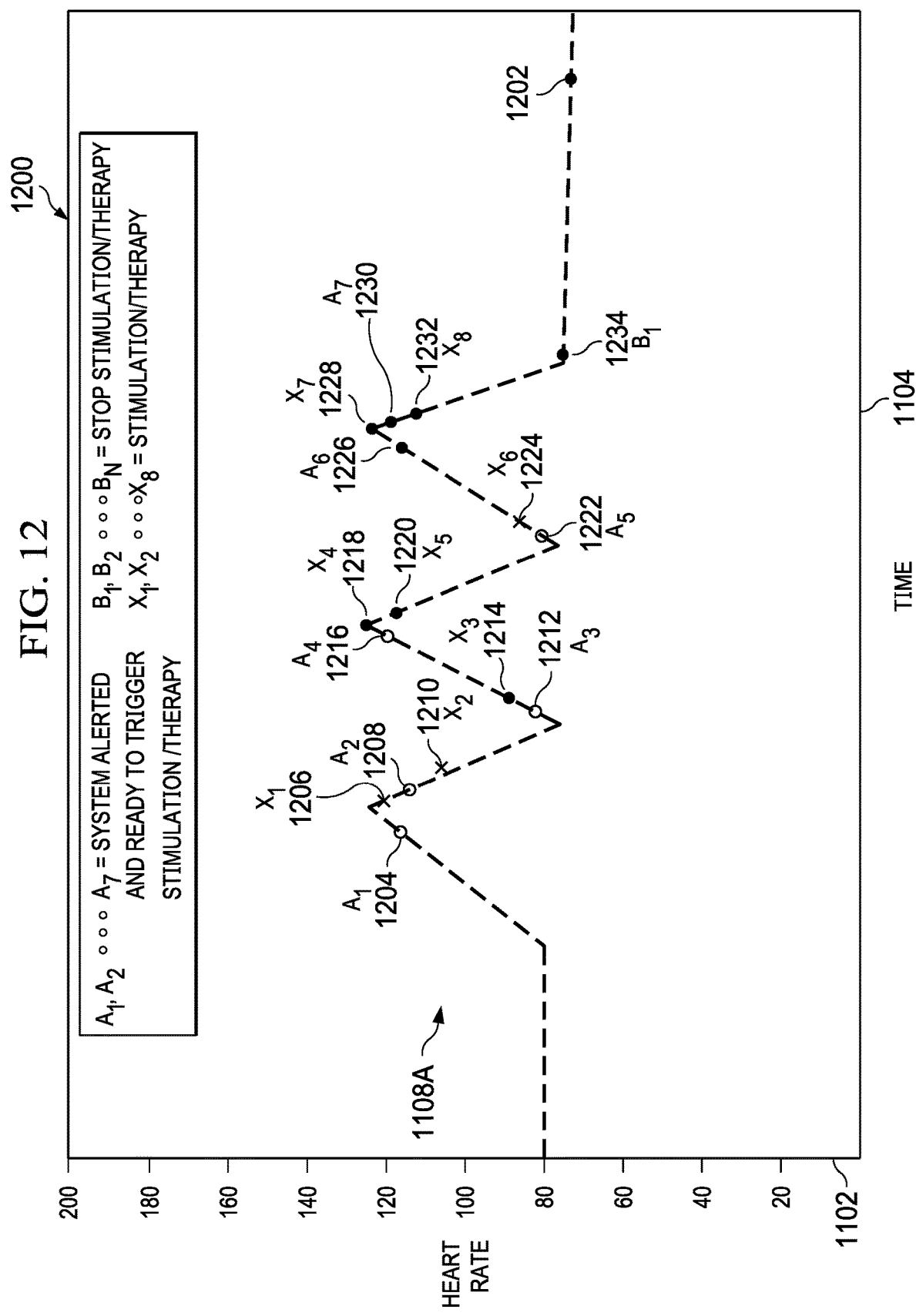
FIG. 12 is another graph of heart rate versus time, according to one embodiment.

In FIG. 12, another graph of heart rate versus time is shown, according to one embodiment. A second graph 1200 illustrating a second heart rate versus time line 1202 for the patient is shown. In this example, the patient's heart rate goes from 80 heart beats per minute to 120 heart beats per minute which creates a first system alert event 1204 (e.g., A1). Further, the system, device, and/or method initiates a first therapy 1206 (e.g., X1) based on the first system alert event 1204. In addition, a second system alert event 1208 (e.g., A2) occurs and a second therapy 1210 (e.g., X2) is initiated based on the second system alert event 1208. In addition, a third system alert event 1212 (e.g., A3) occurs and a third therapy (e.g., X3) 1214 is initiated based on the third system alert event 1212 (e.g., A3). In addition, a fourth system alert event 1216 (e.g., A4) occurs and a fourth therapy 1218 (e.g., X4) is initiated based on the fourth system alert event 1216 (e.g., A3). Further, a fifth therapy 1220 (e.g., X5) is initiated based on the effects of the fourth therapy 1218 (e.g., X4). In addition, a fifth system alert event 1222 (e.g., A5) occurs and a sixth therapy (e.g., X6) 1224 is initiated based on the fifth system alert event 1222 (e.g., A5). In addition, a sixth system alert event 1226 (e.g., A6) occurs and a seventh therapy (e.g., X7) 1228 is initiated based on the sixth system alert event 1226 (e.g., A6). In addition, a seventh system alert event 1230 (e.g., A7) occurs and an eighth therapy (e.g., X8) 1232 is initiated based on the seventh system alert event 1230 (e.g., A7). In addition, a first stop stimulation event 1234 (e.g., B1) occurs which turns off all therapies and/or system alerts may occur when the heart rate returns to the approximate starting heart rate and/or a target value. In these examples shown with FIG. 12, a rise over run heart rate calculation was completed to determine the one or more system alerts. However, it should be noted that any calculation (e.g., % increase, % decrease, etc. can be utilized). Further, all systems alerts and/or therapies may occur as independent events and/or examples. For example, the seventh system alert may be the first system alert in a specific example In other words, no other events and/or therapies occurred before the seventh system alert. Therefore, the seventh system alert becomes the first system alert. In addition, one or more warnings may be transmitted to the patient, a caregiver, a doctor, a medical professional, and/or logged. In addition, there may be up to an Nth alerts, an Nth stop stimulation (and/or therapy) event, and an Nth therapy in any of the examples disclosed in this document.

Figure 13:
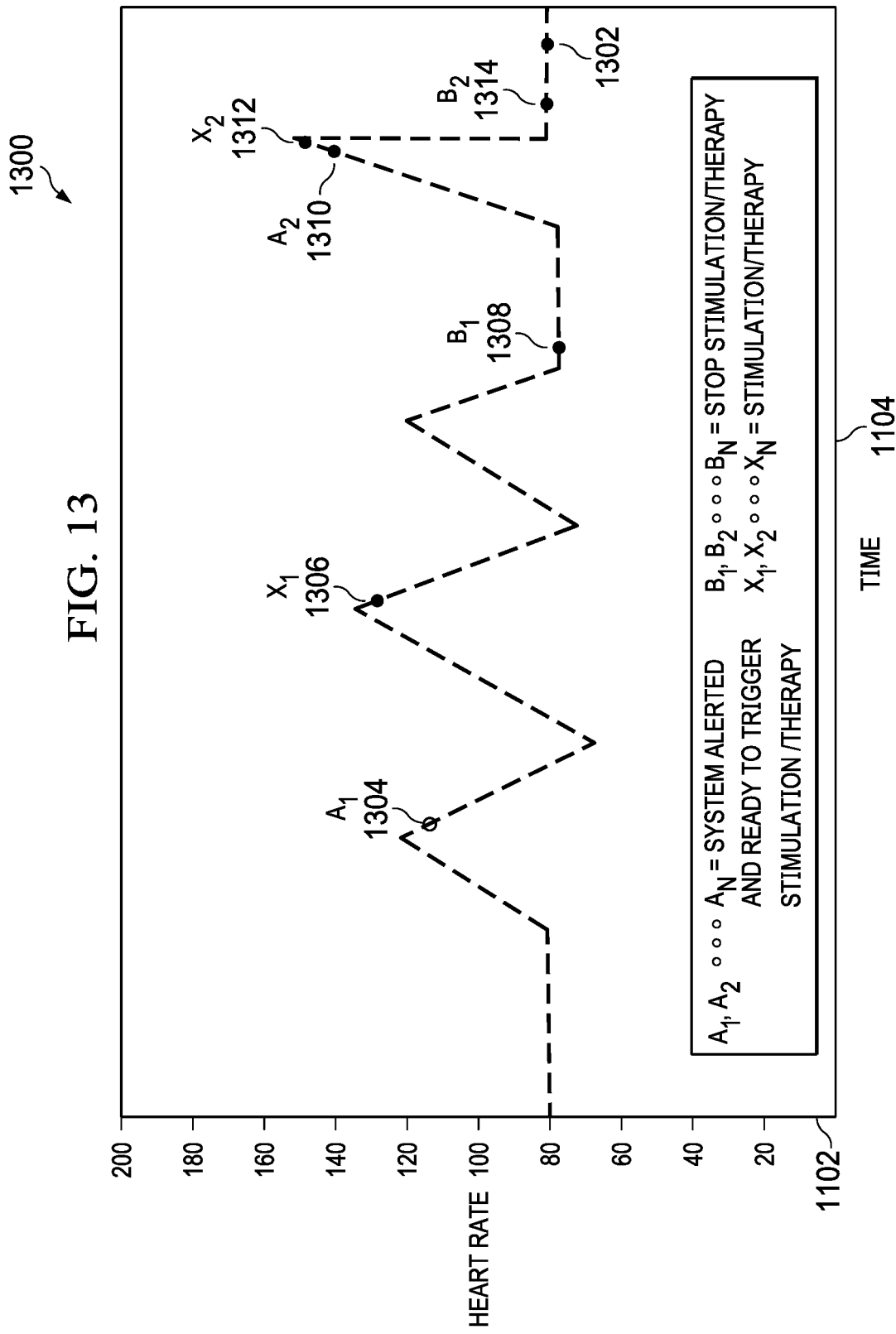
FIG. 13 is another graph of heart rate versus time, according to one embodiment.

In FIG. 13, another graph of heart rate versus time is shown, according to one embodiment. A third graph 1300 illustrating a third heart rate versus time line 1302 for the patient is shown. In this example, the patient's heart rate goes from 80 heart beats per minute to 116 heart beats per minute which creates a first system alert event 1304 (e.g., A1). Further, the system, device, and/or method initiates a first therapy 1306 (e.g., X1) based on the first system alert event 1304. In addition, a first stop stimulation event 1308 (e.g., B1) occurs which turns off all therapies and/or system alerts occurs when the heart rate returns to the approximate starting heart rate and/or a target value. Further, the patient's heart rate goes from 80 heart beats per minute to 123 heart beats per minute which creates a second system alert event 1310 (e.g., A2). Further, the system, device, and/or method initiates a second therapy 1312 (e.g., X2) based on the second system alert event 1310. In addition, a second stop stimulation event 1314 (e.g., B2) occurs which turns off all therapies and/or system alerts occurs when the heart rate returns to the approximate starting heart rate and/or a target value. In these examples shown with FIG. 13, a percentage change in heart rate calculation was completed to determine the one or more system alerts. However, it should be noted that any calculation (e.g., rise over run, etc. can be utilized). Further, all systems alerts and/or therapies may occur as independent events and/or examples. For example, the second system alert may be the first system alert in a specific example. In other words, no other events and/or therapies occurred before the second system alert. Therefore, the second system alert becomes the first system alert. In addition, one or more warnings may be transmitted to the patient, a caregiver, a doctor, a medical professional, and/or logged.

Figure 14:
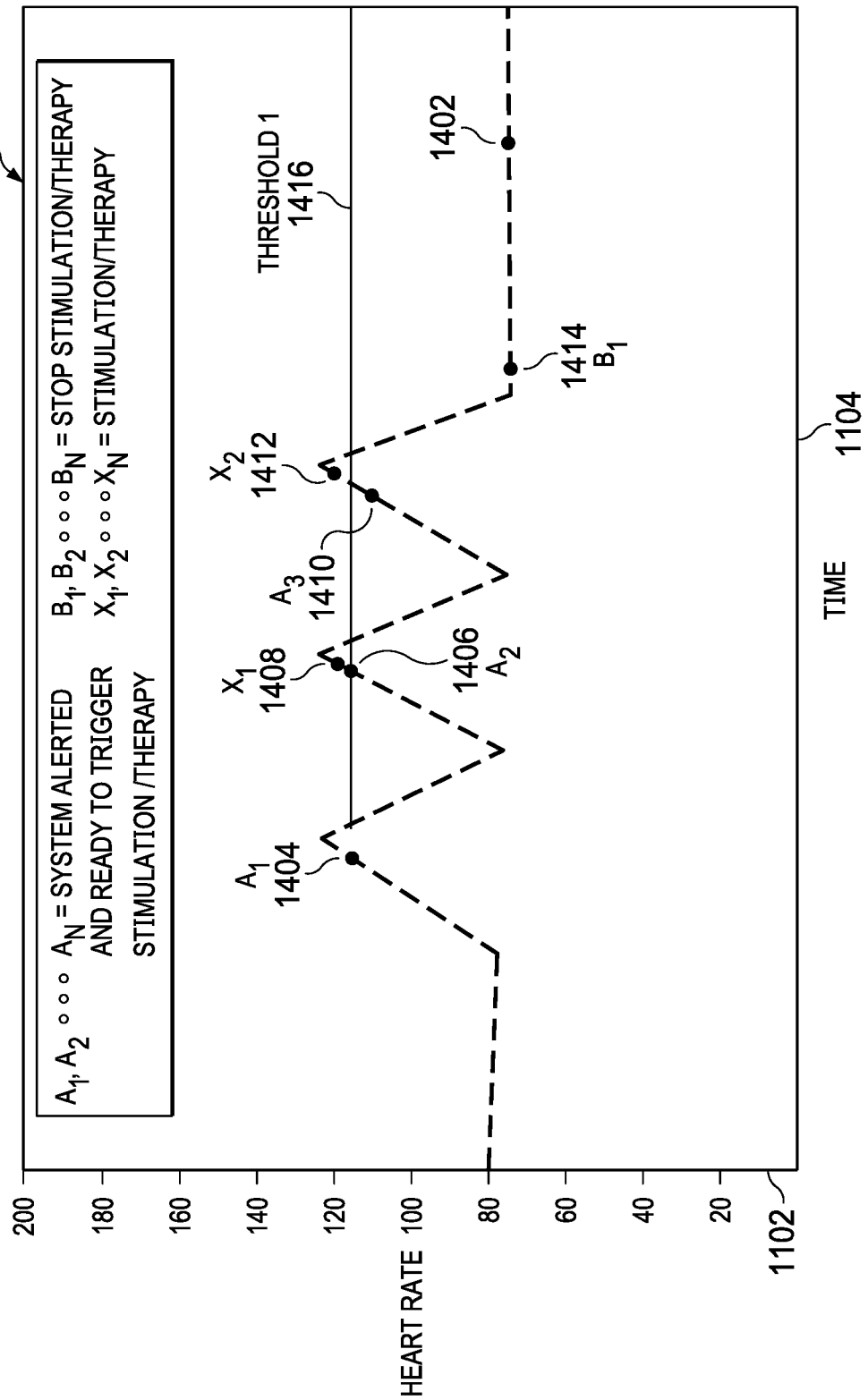
FIG. 14 is another graph of heart rate versus time, according to one embodiment.

In FIG. 14, another graph of heart rate versus time is shown, according to one embodiment. A fourth graph 1400 illustrating a fourth heart rate versus time line 1402 for the patient is shown. In this example, the patient's heart rate goes from 80 heart beats per minute to 120 heart beats per minute which creates a first system alert event 1404 (e.g., A1) because the 120 heart beats per minutes meets or exceeds a first threshold value 1416 (e.g., 115 heart beats per minute). In this example, a second system alert event 1406 (e.g., A2) is created because the heart beats of the patient meets or exceeds the first threshold value 1416 (e.g., 115 heart beats per minute). Further, the system, device, and/or method initiates a first therapy 1408 (e.g., X1) based on the first system alert event 1404 and the second system alert event 1406 occurring. The first system alert event 1404 and the second system alert event 1406 may be time dependent. For example, the first system alert event 1404 and the second system alert event 1406 may have to occur within a first time period for the initiation of the first therapy 1408. In another example, the first system alert event 1404 and the second system alert event 1406 may not be time dependent. Further, a third system alert event 1410 (e.g., A3) is created because the heart beats of the patient meets or exceeds (and/or within a specific rate of the threshold—in this example within 5 percent—heart rate is 110) the first threshold value 1416 (e.g., 115 heart beats per minute). Further, the system, device, and/or method initiates a second therapy 1412 (e.g., X2) based on the first system alert event 1404, the second system alert event 1406, and/or the third system event occurring. It should be noted that the second therapy 1412 has a time delay factor utilized with the second therapy 1412. In another example, no time delay is utilized. In addition, one or more time delays can be used with any therapy, any warning, and/or any alert in this document. The first system alert event 1404, the second system alert event 1406, and the third system alert event 1410 may be time dependent. For example, the first system alert event 1404, the second system alert event 1406, and the third system alert event 1410 may have to occur within a first time period for the initiation of the second therapy 1412. In another example, the first system alert event 1404, the second system alert event 1406, and the third system alert event 1410 may not be time dependent. Further, a first stop stimulation event 1414 (e.g., B1) occurs which turns off all therapies and/or system alerts occurs when the heart rate returns to the approximate starting heart rate and/or a target value. Further, all systems alerts and/or therapies may occur as independent events and/or examples. For example, the third system alert may be the first system alert in a specific example. In other words, no other events and/or therapies occurred before the third system alert. Therefore, the third system alert becomes the first system alert. In addition, one or more warnings may be transmitted to the patient, a caregiver, a doctor, a medical professional, and/or logged.

Figure 15:
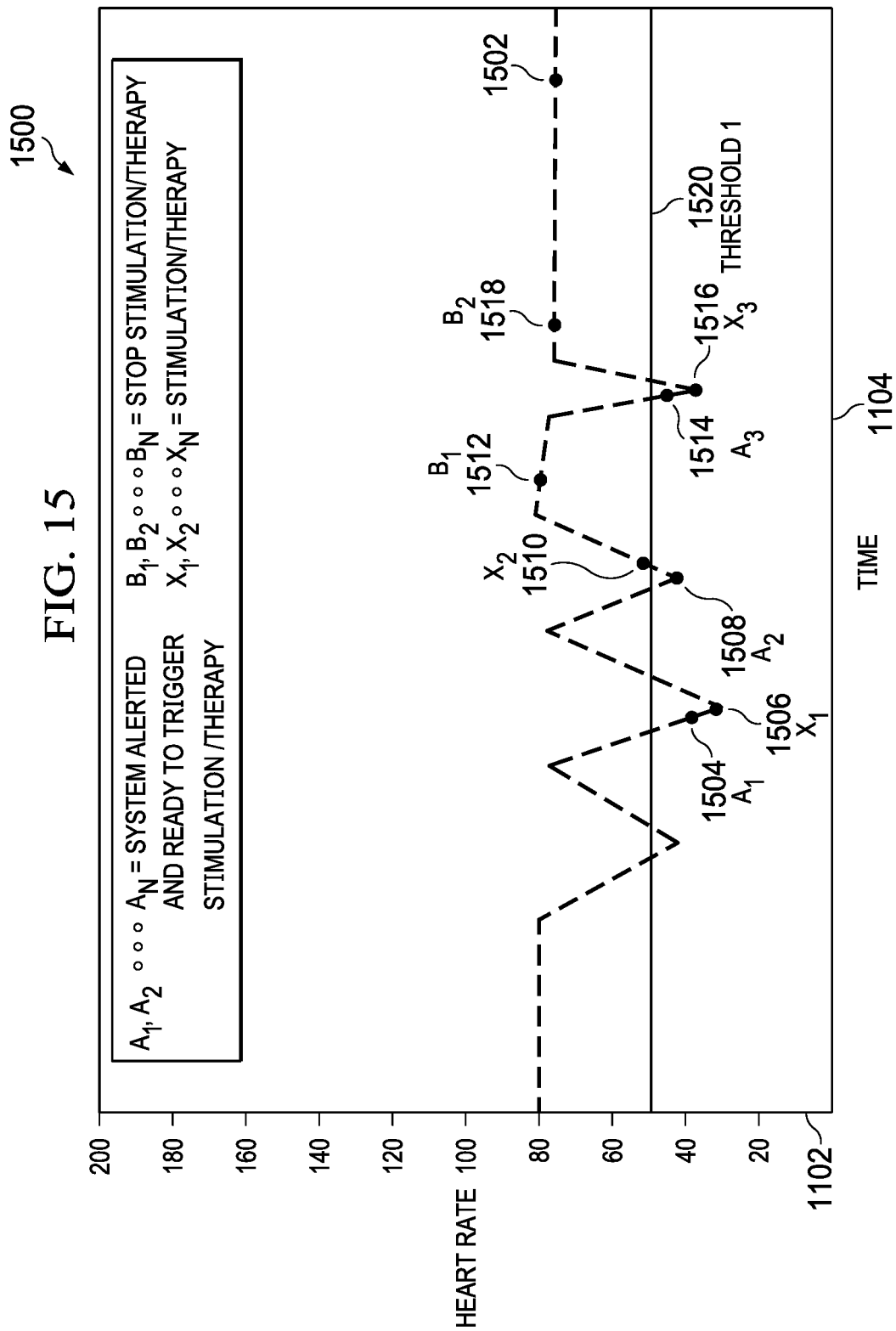
FIG. 15 is another graph of heart rate versus time, according to one embodiment.

In FIG. 15, another graph of heart rate versus time is shown, according to one embodiment. A fifth graph 1500 illustrating a fifth heart rate versus time line 1502 for the patient is shown. In this example, the patient's heart rate goes from 80 heart beats per minute to 40 heart beats per minute which creates a first system alert event 1504 (e.g., A1) because the 40 heart beats per minutes meets or exceeds a first threshold value 1520 (e.g., 50 heart beats per minute). It should be noted that no alert was generated when the heart rate fell to 52 heart beats per minute because 52 heart beats per minute is above the threshold value of 50 heart beats per minute. Further, the system, device, and/or method initiates a first therapy 1506 (e.g., X1) based on the first system alert event 1504 occurring. Further, the patient's heart rate goes from 80 heart beats per minute to 50 heart beats per minute which creates a second system alert event 1508 (e.g., A2) because the 50 heart beats per minutes meets or exceeds the first threshold value 1520 (e.g., 50 heart beats per minute). Further, the system, device, and/or method initiates a second therapy 1510 (e.g., X2) based on the second system alert event 1508 occurring. Further, a first stop stimulation event 1512 (e.g., B1) occurs which turns off all therapies and/or system alerts occurs when the heart rate returns to the approximate starting heart rate and/or a target value. In addition, the patient's heart rate goes from 80 heart beats per minute to 45 heart beats per minute which creates an nth system alert event 1514 (e.g., A3) because the 45 heart beats per minutes meets or exceeds the first threshold value 1520 (e.g., 50 heart beats per minute). Further, the system, device, and/or method initiates an Nth therapy 1516 (e.g., X3) based on the nth system alert event 1514 occurring. Further, an nth stop stimulation event 1518 (e.g., B2) occurs which turns off all therapies and/or system alerts occurs when the heart rate returns to the approximate starting heart rate and/or a target value. Further, all systems alerts and/or therapies may occur as independent events and/or examples. For example, nth system alert event 1514 alert may be the first system alert in a specific example In other words, no other events and/or therapies occurred before nth system alert event 1514. Therefore, nth system alert event 1514 becomes the first system alert. In addition, one or more warnings may be transmitted to the patient, a caregiver, a doctor, a medical professional, and/or logged.

In regards to FIGS. 11-15 as related to this disclosure, the systems, devices, and/or methods may use a base line heart rate for the patient (e.g., a specific patient Bob, a general patient John Doe with a first health condition, a first age, etc.) over a first time period (e.g. one week, one month, one year, etc.), 50 percentile of all measured heart rates, an average of all heart rates, and/or any other method of determine a baseline heart rate. Further, the threshold level may be determined based on being the 40 percentile of the baseline, 39 percentile of the baseline, 38 percentile of the baseline, . . . , 10 percentile of the baseline, . . . , etc. In addition, the threshold level may be determined based on being the 75 percentile of the baseline, 76 percentile of the baseline, 77 percentile of the baseline, . . . , 90 percentile of the baseline, . . . , 99 percentile of the baseline, . . . , etc. In one example, the threshold value may be the 75 percentile of every recorded heart rate data. In another example, the oscillation does not matter whether the heart rate change is in an increasing direction or a decreasing direction. In various examples, the systems, devices, and/or method may reduce an amplitude of change (e.g., damping the change in heart rate) to enhance system performance and/or to reduce side effects. In addition, the determination of one or more side effects may initiate a reduction in therapy, a stoppage of therapy, a modification of therapy (e.g., changing a therapy that reduces heart rate to another therapy that increases heart rate), one or more warnings, and/or one or more logging of data.

Figure 16:
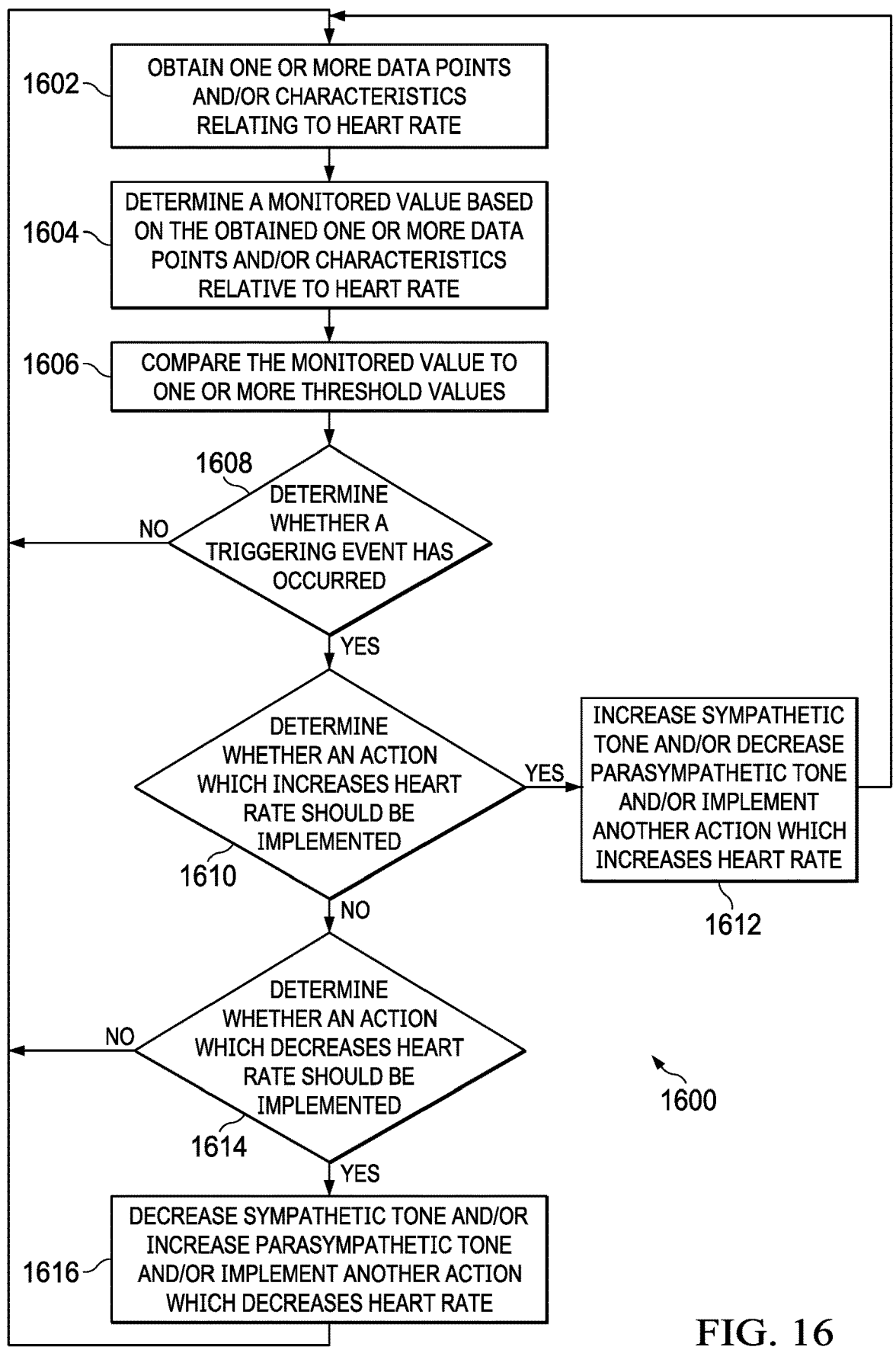
FIG. 16 is a flowchart of a therapy procedure, according to one embodiment.

In FIG. 16, a flowchart of a therapy procedure is shown, according to one embodiment. A method 1600 includes obtaining one or more data points and/or characteristics relating to heart rate of a patient (step 1602). The method 1600 may also include determining a monitored value based one the obtained one or more data points and/or characteristics relating to the heart rate (step 1604). The method 1600 may further compare the monitored value to one or more threshold values (step 1606). The method 1600 may via one or more processors (of a medical device(s) and/or medical device system) determine whether a triggering event has occurred (step 1608). If no triggering event has occurred, then the method 1600 moves back to step 1602. If a triggering event has occurred, then the method 1600 may determine via one or more processors (of a medical device(s) and/or medical device system) whether an action which increases heart rate should be implemented (step 1610). If an action which increases heart rate should be implemented, then the method 1600 may increase a sympathetic tone via one or more actions and/or decrease a parasympathetic tone via one or more actions and/or implement another action which increases heart rate (step 1612). After the implements of one or more actions, the method 1600 returns to step 1602. If an action which increases heart rate should not be implemented, then the method 1600 may determine via one or more processors (of a medical device(s) and/or medical device system) whether an action which decreases heart rate should be implemented (step 1614). If an action which decreases heart rate should be implemented, then the method 1600 may decrease a sympathetic tone via one or more actions and/or increase a parasympathetic tone via one or more actions and/or implement another action which decreases heart rate (step 1616). After the implements of one or more actions, the method 1600 returns to step 1602.

In one embodiment, a system for treating a medical condition in a patient includes: a sensor for sensing at least one body data stream; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the system includes at least one electrode coupled to a vagus nerve of the patient and a programmable electrical signal generator. In another example, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. In another example, the one or more processors may increase a parasympathetic tone to decrease the heart rate of the patient. In another example, the system includes a seizure detection unit which analyzes the at least one body data stream to determine an epileptic seizure status. In another example, the system includes at least one electrode coupled to a vagus nerve of the patient and a programmable electrical signal generator. Further, the one or more processors may apply an electrical signal to the vagus nerve of the patient based on a determination that a seizure is characterized by a decrease in the heart rate of the patient where the electrical signal is applied to block action potential conduction on the vagus nerve.

In another embodiment, a system for treating a medical condition in a patient, includes: a sensor for sensing at least one body data stream; at least one electrode coupled to a vagus nerve of the patient; a programmable electrical signal generator; a heart rate unit capable of determining a heart rate of the patient based on the at least one body data stream; and a logic unit configured via one or more processors to compare a monitored value which is determined based on one or more data points relating to the heart rate to one or more threshold values, the logic unit further configured to determine a triggering event based on the comparison. Further, the one or more processors may initiate one or more actions to change the heart rate of the patient based on the determination of the triggering event.

In another example, the one or more processors may increase a sympathetic tone to increase the heart rate of the patient based on a first triggering event. Further, the one or more processors may decrease a sympathetic tone to decrease the heart rate of the patient based on a second triggering event. Further, the one or more processors may decrease a parasympathetic tone to increase the heart rate of the patient based on a third triggering event. Further, the one or more processors may increase a parasympathetic tone to decrease the heart rate of the patient based on a fourth triggering event.

In another example, the one or more processors may increase the sympathetic tone to increase the heart rate of the patient based on a second triggering event. Further, the one or more processors may increase the sympathetic tone to increase the heart rate of the patient based on a third triggering event. Further, the one or more processors increase the sympathetic tone to increase the heart rate of the patient based on an nth triggering event.

In another example, the one or more processors decrease a sympathetic tone to decrease the heart rate of the patient based on a first triggering event. Further, the one or more processors decrease the sympathetic tone to decrease the heart rate of the patient based on a second triggering event. Further, the one or more processors may decrease the sympathetic tone to decrease the heart rate of the patient based on a third triggering event. In addition, the one or more processors decrease the sympathetic tone to decrease the heart rate of the patient based on an nth triggering event.

Cardio-protection in epilepsy is a rapidly growing field of vital importance. In this disclosure, systems, devices, and/or method of protecting the heart from standstill or fatal arhythmias are disclosed. Further in this disclosure, systems, devices, and/or methods of automated detections, warnings, reportings, treatments, controls and/or any combination thereof of ictal and peri-ictal chronotropic instability are shown.

Figure 17:
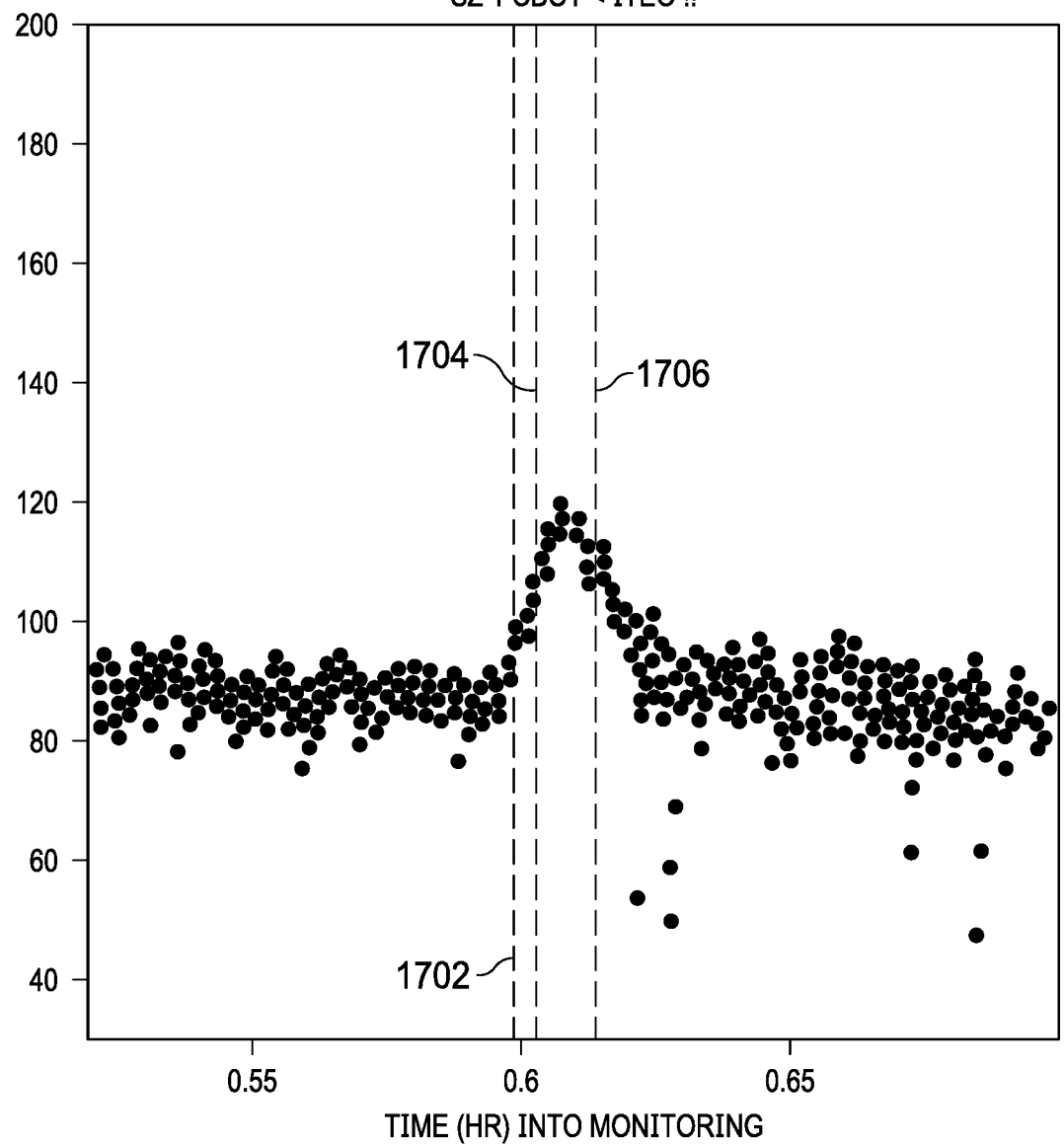
FIG. 17 is a graph relating to the automated detection and control of ictal and peri-ictal chronotropic instability, according to one embodiment.
Figure 18:
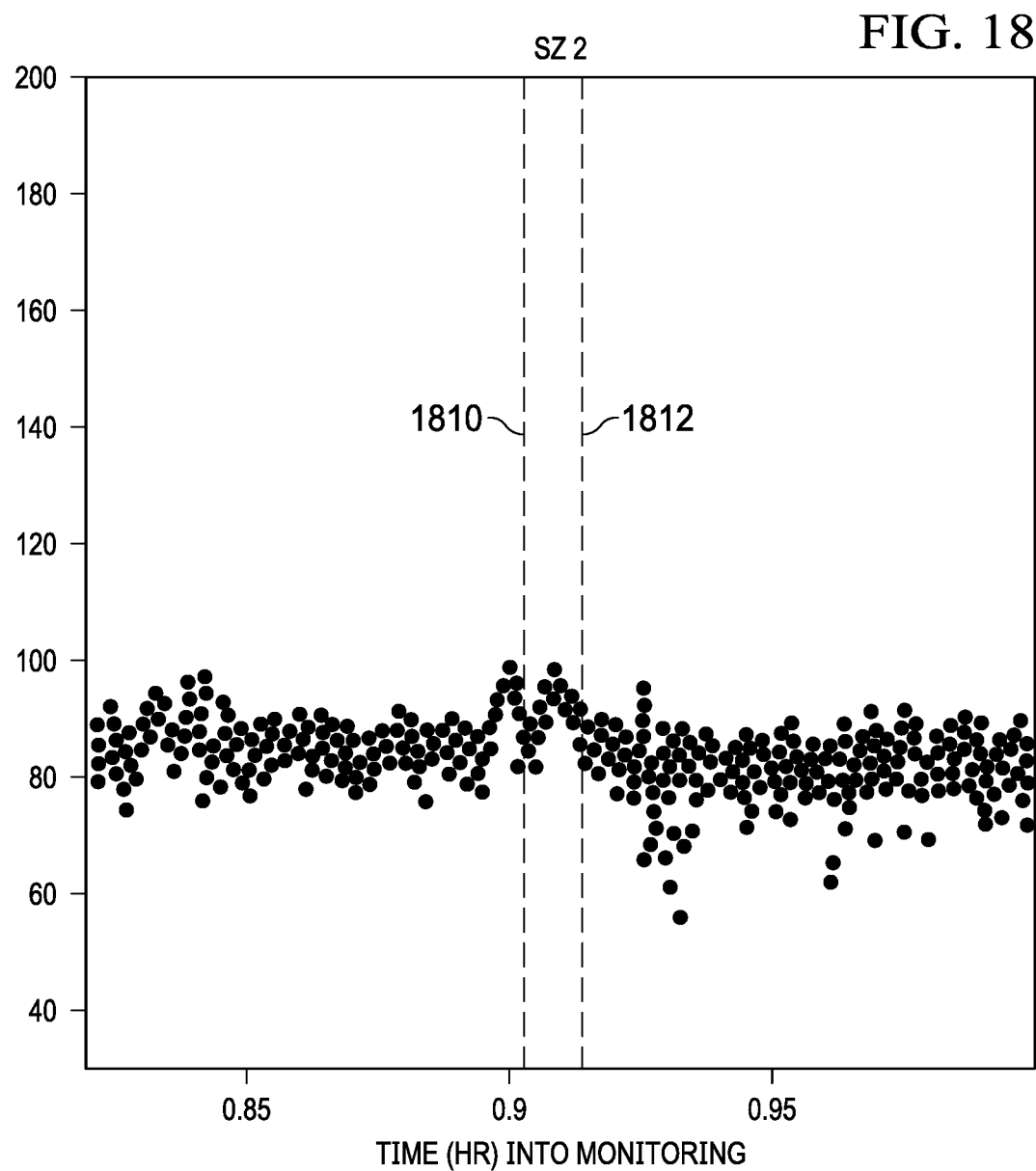
FIG. 18 is a graph relating to the automated detection and control of ictal and peri-ictal chronotropic instability, according to one embodiment.

In FIG. 17, a graph shows monotonic increase and decrease in heart rate. In FIG. 17, a first triggering event, a first warning event, and/or a first therapy event 1702 are shown. Further, a second triggering event 1704, a second warning event, and/or a second therapy event 1704 are shown. In addition, an Nth triggering event, an Nth warning event, and/or an Nth therapy event 1706 are shown. In FIG. 18, the heart rate of the patient increases which is followed by a decrease in heart rate, then an increase heart rate and a final decrease in heart rate. In this example, the first drop in heart rate crossed downwardly the detection threshold which would have temporarily disabled the warning system and the delivery of the therapy. While the first peak was not temporally correlated with paroxysmal activity on any of the intra-cranial electrodes used in this patient, it is likely that the first increase in heart rate was caused by epileptic discharges from a brain site that was not being investigated. In this example, the x-axis is time in hours and the y-axis is heart beats per minute. In this example, an electrographic onset in the brain 1810 is shown and an electrographic termination in the brain 1812 is shown.

Figure 19:
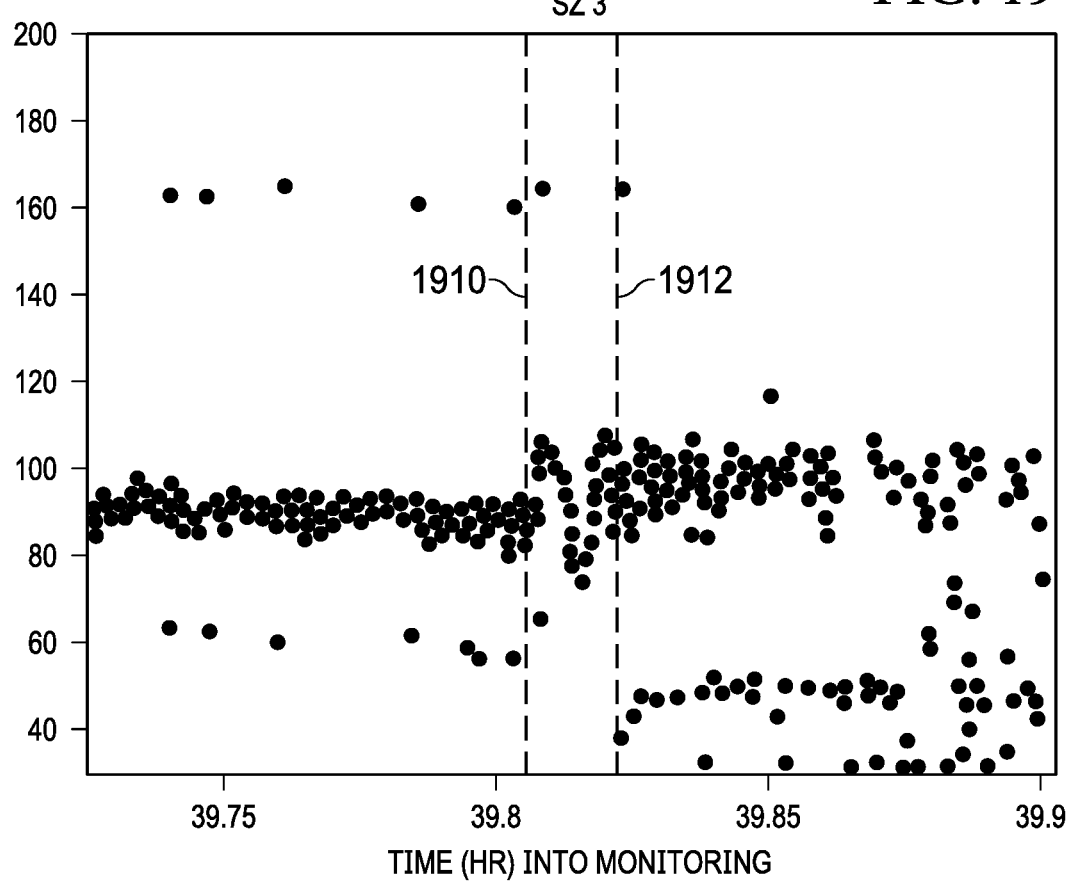
FIG. 19 is a graph relating to the automated detection and control of ictal and peri-ictal chronotropic instability, according to one embodiment.

In FIG. 19, a change in ictal heart rate is shown. In this example, the drop in heart rate during the seizure, is even more prominent that the one depicted in FIGS. 17-18, as it is below the inter-ictal baseline. It should be noted that the oscillations in heart rate during the post-ictal period are indicative of cardiac instability. In this example, a seizure onset point 1910 and a seizure termination point 1912 are shown.

Figure 20:
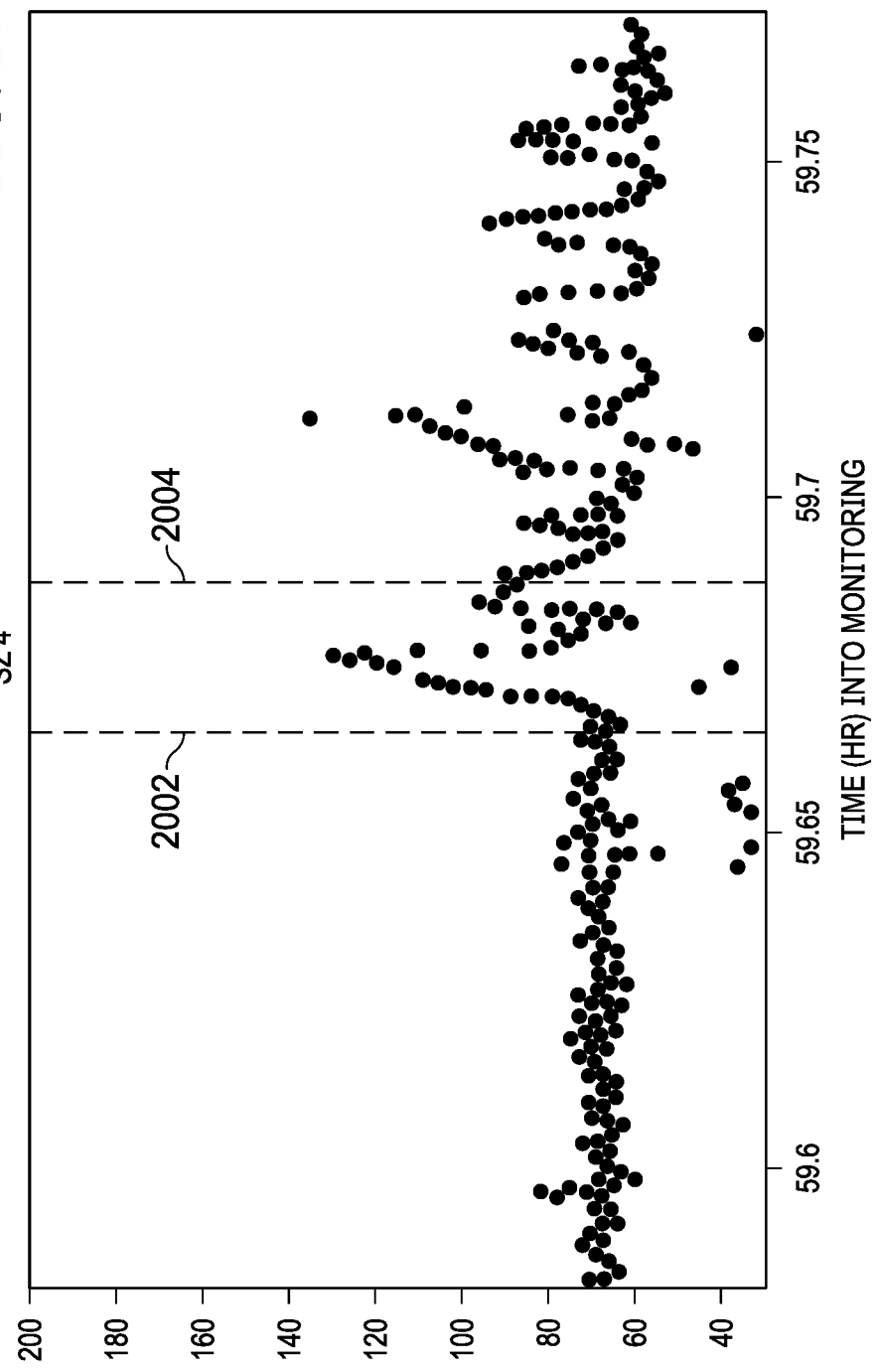
FIG. 20 is a graph relating to the automated detection and control of ictal and peri-ictal chronotropic instability, according to one embodiment.

In FIG. 20, large amplitude tachycardia cycles occurring quasi-periodically after termination of paroxysmal activity recorded with intra-cranial electrodes. While the mechanisms responsible for these oscillations are unknown, the probability that they are epileptic in nature cannot be excluded, since electrographic and imaging data used to guide intra-cranial electrode placement pointed to the existence of only one epileptogenic site.

Figure 21:
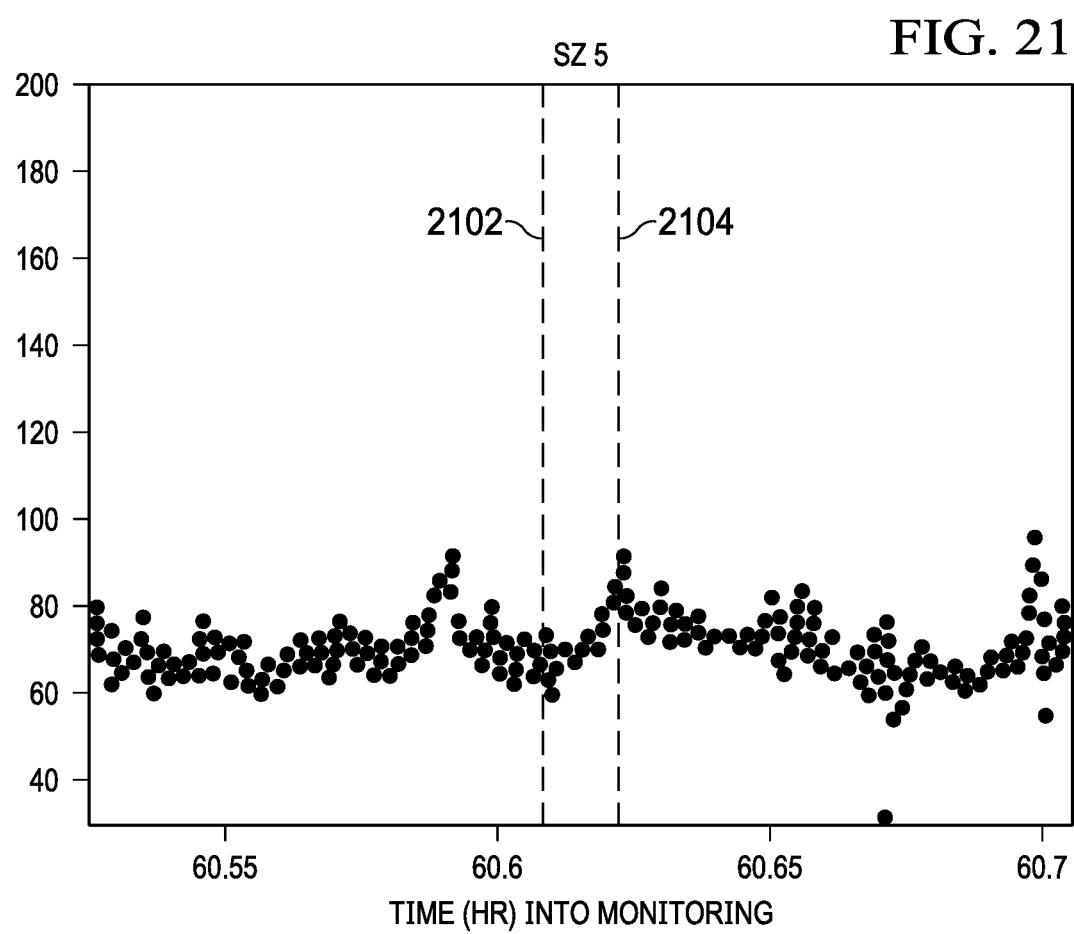
FIG. 21 is a graph relating to the automated detection and control of ictal and peri-ictal chronotropic instability, according to one embodiment.

In FIG. 21, small amplitude continuous quasi-periodic oscillations preceding and following a seizure recorded with intra-cranial electrodes (same patient as FIG. 20). In various embodiments, ictal and peri-ictal cardiac instability are shown. The mechanisms leading to SUDEP have not been elucidated, in part due to the inability to record data during the critical events that culminate in cardiac fibrillation or in standstill (or in respiratory arrest). In this example, a first triggering event, a first warning event, and/or a first therapy event 2102 are shown. Further, an Nth triggering event, an Nth warning event, and/or an Nth therapy event 2104 are shown.

The data obtained in intractable epileptics undergoing epilepsy surgery evaluation not only supports a cardiac mechanism (of course, not at the exclusion of catastrophic respiratory failure) but more specifically points to chronotropic instability as backdrop against which, lethal arrhythmias or cardiac standstill may ensue. Moreover, the instability is not restricted to the ictal period but, in certain cases, precedes and/or follows it for several minutes. FIGS. 17-21 illustrate the spectrum of instability in intractable epileptics. This phenomenon is referred herein as Ictal and Pre-Ictal Chronotropic Instability.

The challenges that for accurate quantification and delivery of efficacious therapies, ictal chronotropic instability poses, were addressed and strategies to manage them are outlined. Here, the attention is focused on Ictal and Pre-Ictal Chronotropic Instability, a more prolonged and serious pathological phenomenon in intractable epileptics and on the vital issues of cardio-protection.

The aim of this disclosure is to contingently and adaptively dampen based on the slope, amplitude, duration and "direction" (positive or negative chronotropic and its magnitude relative to an adaptive baseline/reference heart rate) the heart oscillations present before, during or after epileptic seizures.

While several embodiments may be envisioned, on embodiment (for efficacy, practicality and cost-effectiveness) is to electrically stimulate/activate the trunk or a branch of the right vagus nerve in the case of elevations in heart (to reduce the heart rate, when there are more than 2 consecutive oscillations/cycles or 1 that is large and prolonged. The intensity and duration of stimulation as well as other parameters are determined by the slope, amplitude and duration of the oscillations, while ensuring adequate blood perfusion to all organs. In the case of negative chronotropic effects (decreases in heart rate) the trunk or a branch of the right vagus nerve may be "blocked" using certain electrical stimulation techniques or through cooling; the effect of this intervention is to increase heart rate.

In one embodiment, the "height" of the oscillation is the only feature considered. While obviously important, this embodiment does not take into consideration a possibly more important feature: the rate at which the oscillation occurs: the consequences of waiting to intervene until an oscillation reaches a certain height (e.g., 120 bpm) are different if it takes, 30 seconds for the heart rate to reach the value than if it takes 2 seconds to reach the value. Estimating the rate of change of the heart rate, provides life-saving information. Another aspect is the inter-maxima or inter-minima interval between oscillations. Having heart rate oscillation occur every 2-3 seconds is much more serious than every 1-2 hours. In one example, one benefit may be that the window to act is lengthen which can save lives. In one embodiment, a system for treating a medical condition in a patient includes: a sensor for sensing at least one body data stream; a heart rate unit which determines a heart rate and a heart rate oscillation of the patient based on the at least one body data stream; and a logic unit which compares via one or more processors a monitored value which is determined based on one or more data points relating to the heart rate and to the heart rate oscillation to a threshold value, the logic unit determines a triggering event based on the comparison where the one or more processors initiate one or more actions to change the heart rate of the patient based on the determination of the triggering event.

In another example, the system includes at least one electrode coupled to a vagus nerve of the patient and a programmable electrical signal generator. Further, the one or more processors may increase a sympathetic tone to increase the heart rate of the patient. In another example, the one or more processors may decrease a parasympathetic tone to increase the heart rate of the patient. In another example, the one or more processors may decrease a sympathetic tone to decrease the heart rate of the patient. Further, the one or more processors may increase a parasympathetic tone to decrease the heart rate of the patient. In addition, the system may include a seizure detection unit which analyzes the at least one body data stream to determine an epileptic seizure status. The system may include at least one electrode coupled to a vagus nerve of the patient and a programmable electrical signal generator where the one or more processors apply an electrical signal to the vagus nerve of the patient based on a determination that a seizure is characterized by a decrease in the heart rate of the patient and where the electrical signal is applied to block action potential conduction on the vagus nerve. In addition, the heart unit may determine an inter-maxima interval and an inter-minima interval between a first oscillation and a second oscillation.

Further, the logic unit may compare the inter-maxima interval and the inter-minima interval to an interval threshold. In addition, the one or more processors may initiate one or more actions based on the interval threshold being reached.

The particular embodiments disclosed above are illustrative only as the disclosure may be modified and practiced in different but equivalent manners apparent to those skilled in the art having the benefit of the teachings herein. Furthermore, no limitations are intended to the details of construction or design herein shown other than as described in the claims below. It is, therefore, evident that the particular embodiments disclosed above may be altered or modified and all such variations are considered within the scope and spirit of the disclosure. Accordingly, the protection sought herein is as set forth in the claims below. In addition, all examples, embodiments, and/or elements may be combined in any manner that are disclosed in this document. In other words, an element from a first example (paragraph [0088]) can be combined with any other element, such as, a second element from an Nth example (paragraph [0163]). For brevity, all these examples are not written out but are part of this document.

Identification of changes in brain state are generally described in U.S. patent application Ser. No. 12/896,525, filed Oct. 1, 2010, incorporated herein by reference. As stated therein, implanted sensors or electrodes beneath the scalp but above the outer skull table or intra-cranial (epidural, subdural or depth) have been used to overcome the limitations of scalp recordings. However, the quality of data is limited; there are risks (e.g., infection, bleeding, brain damage) associated with these devices; and in addition, at this time, there are at most about 300 neurosurgeons capable of implanting intracranial electrodes, far too few to perform such implantation for the roughly 900,000 pharmaco-resistant epileptics in the United States.

The basis for our work in using multimodal signals for detection of state changes in the brain is as generally described in U.S. patent application Ser. No. 12/896,525, filed Oct. 1, 2010. Various multimodal signals that may be used in the disclosure are set forth in the following table:

TABLE 1

| Multimodal Signals |
|---|
| Autonomic |
| Cardiac: EKG, PKG, Echocardiography, Apexcardiography (ApKG), Intra-cardiac pressure, Cardiac blood flow, cardiac thermography; from which can be derived, e.g., heart rate (HR), change of HR, rate of change of HR, heart rhythm, changes in heart rhythm, heart rate variability (HRV), change of HRV, rate of change of HRV, HRV vs. HR. Also, heart morphology (e.g., size) blood pressure (arterial and venous), heart sounds, heartbeat wave morphology, heartbeat complex morphology, and magnitude and shape thoracic wall deflection. Vascular: Arterial Pressure, Arterial and venous blood wave pressure morphology; Arterial and venous blood flow velocity and degree of turbulence, arterial and venous blood flow sounds, arterial and venous temperature Respiratory: Frequency, tidal volume, minute volume, respiratory wave morphology, respiratory sounds, end-tidal CO2, Intercostal EMG, Diaphragmatic EMG, chest wall and abdominal wall motion, from which can be derived, e.g.,, respiration rate (RR), change of RR, rate of change of RR, respiratory rhythm, morphology of breaths. Also, arterial gas concentrations, including oxygen saturation, as well as blood pH can be considered respiratory signals. Dermal: Skin resistance, skin temperature, skin blood flow, sweat gland activity Concentrations of catecholamines (and their metabolites) and acetylcholine or acetylcholinesterase activity in blood, saliva and other body fluids concentrations and its rate of change. |
| Neurologic |
| Cognitive/behavioral: Level of consciousness, attention, reaction time, memory, visuo-spatial, language, reasoning, judgment, mathematical calculations, auditory and/or visual |

TABLE 1-continued

Multimodal Signals discrimination
Kinetic: Direction, speed/acceleration, trajectory (1D to 3D), pattern, and quality of
movements, force of contraction, body posture, body orientation/position, body part
orientation/position in reference to each other and to imaginary axes, muscle tone, agonist-
to-antagonist muscle tone relation, from which can be derived, e.g., information about gait,
posture, accessory movements, falls
Vocalizations: Formed, unformed
EEG/ECoG, Evoked potentials, field potentials, single unit activity
Endocrine: Prolactin, luteinizing hormone, follicle stimulation hormone, growth hormone,
ACTH, cortisol, vasopressin, beta-endorphin, beta, lipotropin.-, corticotropin-releasing
factor (CRF)
Stress Markers: CK, troponin, reactive oxygen and nitrogen species including but not limited to
iso- and neuro-prostanes and nitrite/nitrate ratio, gluthatione, gluthatione disulfide and
gluthatione peroxidase activity, citrulline, protein carbonyls, thiobarbituric acid, the heat shock
protein family, catecholamines, lactic acid, N-acetylaspartate, and metabolites of any of
the foregoing.
Metabolic: arterial pH and gases, lactate/pyruvate ratio, electrolytes, glucose Terms such as "epileptic event" and "reference value," among others, have been defined in U.S. patent application Ser. No. 12/896,525, filed Oct. 1, 2010. "Interictal" refers to a period after a post-ictal period and before a pre-ictal period.

FIGS. 25-28 have been substantially fully described in U.S. patent application Ser. No. 12/896,525, filed Oct. 1, 2010.

Various features of signals for various types of seizures are also generally described in U.S. patent application Ser. No. 12/896,525, filed Oct. 1, 2010.

U.S. patent application Ser. No. 12/896,525, filed Oct. 1, 2010 also discusses methods capable of distinguishing epileptic generalized from non-epileptic generalized or "convulsive" seizures whose kinetic activity, but not pathophysiology, resembles that of epileptic seizures.

The selectivity (Sl), sensitivity (Se) and specificity (Sp) of various signal features are generally described in U.S. patent application Ser. No. 12/896,525, filed Oct. 1, 2010. U.S. patent application Ser. No. 12/896,525 also discusses consideration of these and other signal features in determining optimal signal(s) for use in detection of epileptic events in a particular patient, of a particular type, or the like.

A Positive Predictive Value (PPV) of a signal or combination of signals is generally described in U.S. patent application Ser. No. 12/896,525, filed Oct. 1, 2010. The person of ordinary skill in the art will also understand a Negative Predictive Value (NPV) of a signal, defined as:

(number of True Negatives)/number of True Negatives+number of False Negatives.

In one embodiment, the present disclosure relates to a method, comprising receiving at least one of a signal relating to a first cardiac activity from a patient and a signal relating to a first body movement from the patient; deriving at least one patient index from said at least one received signal; triggering at least one of a test of the patient's responsiveness, a test of the patient's awareness, a test of a second cardiac activity of the patient, a test of a second body movement of the patient, a spectral analysis test of a second cardiac activity of the patient, and a spectral analysis test of a second body movement of the patient, based on said at least one patient index; determining an occurrence of an epileptic event based at least in part on the one or more triggered tests; and performing a further action in response to the determination of the occurrence of the epileptic event.

Cardiac activity signals, as well as techniques for determining them, are generally described in U.S. patent application Ser. No. 12/896,525, filed Oct. 1, 2010.

Body movement (a.k.a. kinetic) signals, as well as techniques for determining them, are generally described in U.S. patent application Ser. No. 12/896,525, filed Oct. 1, 2010. It should be borne in mind that the terms "body movement" and "kinetic," as used herein, also encompass the absence of specific body movements (motionless).

The term, and concept of, "responsiveness" as used in reference to the embodiments described herein, has a motor and a cognitive component which may be strongly correlated or dissociated; further the motor component may be in the form of a simple response (e.g., withdrawal of a limb from a pain source) or complex (e.g. drawing a triangle in response to a command). Consequently, responsiveness may be tested using simple stimuli (e.g., acoustic in the form of a loud noise or sensory in the form of a pinprick) or complex (e.g., complex reaction time tests; questions probing knowledge, judgment, abstraction, memory, etc.). In this disclosure, when "responsiveness" is tested using complex stimuli, "awareness" is being probed and therefore in that case these terms/concepts are used interchangeably. The meaning of "responsiveness" is thus, context dependent: if the objective is to determine if a patient generates simple motor responses or movements, the term "responsiveness" may be used and if it is to test the presence and quality of complex responses, "awareness" may replace responsiveness.

As used herein, "spectral analysis" encompasses spectral analyses using at least one of the known methods (e.g., Fourier-based, wavelet based; multifractal spectral, etc) of cardiac activity or body movements. Spectral analysis techniques are known to the person of ordinary skill in the art and can be implemented by such a person having the benefit of the present disclosure. Spectral analysis may be discrete or continuous. Spectral analysis of a cardiac activity can comprise spectral analysis of heart rate or individual beats' EKG complexes, among others.

The patient index can be a value derived directly from the signal relating to the first cardiac activity or the signal relating to the first body movement. For example, one or more heart rate values can be derived from a cardiac activity signal over one or more periods of time. For example, as described in U.S. patent application Ser. No. 12/770,562, filed Apr. 29, 2010, a foreground heart rate over a relatively short time period (e.g., 5-30 seconds) and a background heart rate over a longer time period (e.g., 30-600 seconds)

can both be derived from a cardiac activity signal. For another example, an accelerometer or inclinometer mounted on a patient's body can give information about the patient's (and/or parts of his body) movements and body position, such as are described in more detail in U.S. patent application Ser. No. 12/896,525, filed Oct. 1, 2010.

The patient index can also be a determination of an epileptic event. For example, the cardiac activity and/or body movement can be analyzed to determine an occurrence of an epileptic event, a non-occurrence of an epileptic event, or a probable occurrence of an epileptic event.

In one embodiment, triggering the test(s) can be based on at least one of a patient's cardiac activity and the patient's body movement upon a finding that the cardiac activity and/or body movement are indicative of a possible epileptic event. For example, if the cardiac activity and/or body movement clearly indicate an epileptic event with high confidence, triggering the test(s) need not be performed; but if the cardiac activity and/or body movement are outside their interictal reference value ranges but have values that give only low confidence of an epileptic event, triggering can be performed to provide additional information about the patient's condition to indicate whether he or she is suffering an epileptic event or not.

For another example, the patient's cardiac activity at a first time may indicate an epileptic event, and the patient's body movement at a second time and in a particular region of the body may indicate an epileptic event, but if the two times differ, or the body movement is in a different region of the body, or changes in their characteristics (e.g., rate, morphology, pattern, etc.) are discordant with declaring the epileptic event, consideration of cardiac activity and body movement may lead to low confidence of an indication of an epileptic event, and in response thereto, triggering of additional test(s) and/or consideration of additional body signals may be desirable. In other words, there may be a low absolute value of correlation (e.g., a correlation between about 0.4 and 0.4) between the patient's cardiac activity and the patient's body movement that would prevent highly confident determination of an epileptic event. The triggered test(s) may provide enough additional information to make a highly confident determination of an epileptic event (or the non-occurrence of an epileptic event).

Generally, two parameters can be considered highly correlated if the coefficient of correlation is greater than about 0.7, and lowly correlated if the coefficient of correlation is less than about 0.4. Two parameters can be considered highly anticorrelated if the coefficient of correlation is less than about −0.7, and lowly anticorrelated if the coefficient of correlation is greater than about 0.4. One example of parameters/situations that can be considered to be anticorrelated includes an appearance of tachycardia with a disappearance of body movement. Other examples that can be considered to be anticorrelated are a strong body movement with either a substantially unchanged heart rate or a decreased heart rate. The example with the substantially unchanged heart rate can be considered a low anticorrelation, and the example with the decreased heart rate can be considered a high anticorrelation.

Another pair of examples to consider are the correlations between body movement and first derivative of heart rate in an epileptic event vs. in exercise. Generally, the first derivative of heart rate is greater in an epileptic event than in exercise, i.e., body movement and the first derivative of heart rate can be considered more highly correlated in epileptic events than in exercise.

The presence of either high or low correlation or anti-correlations may be used in this disclosure to determine the occurrence of an epileptic event and trigger an action(s) or to determine that an epileptic event is not occurring or did not occur. The first and second cardiac activity may be the same (in other words, triggering can be of a second iteration of a test that reported the first cardiac activity as a result of a first iteration, giving a more current value of the cardiac activity), or they may be different. In one embodiment, the first cardiac activity is heart rate or heart rate variability, and the second cardiac activity is heart beat morphology.

Similarly, the first and second body movement may be the same, or they may be different.

A "test" is used herein to refer to any assay of the patient's cardiac activity, body movement, responsiveness, awareness, or a spectral analysis thereof. The product of a test can be considered a signal, and a signal can be considered as resulting from a test. A test of the second cardiac activity may use substantially the same data source, data processing, and/or related techniques as are used in receiving the signal relating to the first cardiac activity. In another embodiment, the techniques may differ. For example, the first cardiac activity can be heart beat morphology determined by electrocardiography (EKG), and the second cardiac activity can be heart beat morphology determined by phonocardiography (PKG).

Similarly, a test of the second body movement may, but need not, use substantially the same data source, data processing, and/or related techniques as are used in receiving the signal relating to the first body movement.

The concept of first and second cardiac activity or first and second body movement is also applicable to responsiveness and awareness. For example responsiveness activity may be a reflex movement such as withdrawal from a source of painful stimuli and a second responsiveness activity may be a complex movement such as that required to draw a triangle. Different tests of varying levels of complexity may be administered to test responsiveness as defined in this disclosure.

The particular triggered test(s) may be selected based at least in part on the first cardiac activity, the first body movement, or both.

In one embodiment, determining is based on at least one of a finding the patient's awareness differs from a reference responsiveness level, a finding the patient's awareness differs from a reference awareness level, a finding the patient's second cardiac activity includes a characteristic suggestive of an epileptic event, a finding the spectral analysis of the patient's second cardiac activity includes a characteristic suggestive of an epileptic event, and a finding the spectral analysis of the patient's second body movement includes a characteristic suggestive of an epileptic event.

Figure 31:
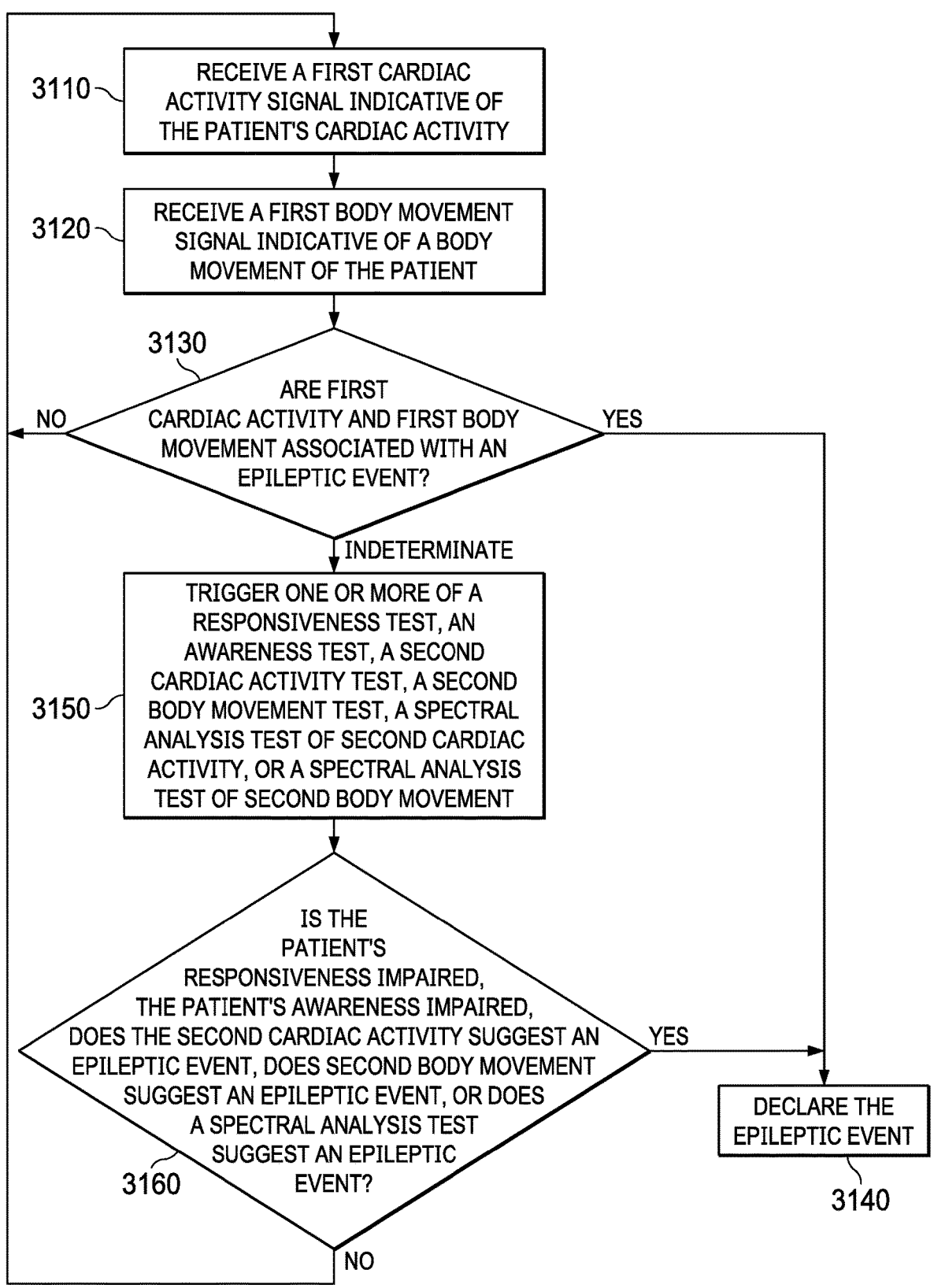
FIG. 31 shows a flowchart of an implementation of a method according to one embodiment of the present disclosure.

FIG. 31 shows a flowchart depicting one embodiment of a method according to the present disclosure. A cardiac activity signal indicative of the patient's cardiac activity is received at block 3110 and/or a body movement signal indicative of a body movement of the patient is received at block 3120.

Thereafter, a determination is made in block 3130 whether cardiac activity and body movement are associated with an epileptic event. If no, flow returns to the receiving blocks 3110-3120. If yes, an epileptic event is declared at block 3140. However, if no determination can be made, flow moves to block 3150, where one or more of a responsiveness test, an awareness test, a second cardiac activity test, a second body movement test, a spectral analysis test of the second cardiac activity, or a spectral analysis test of the second body movement, are triggered.

Thereafter, a determination is made in block 3160 whether the patient's responsiveness, awareness, second cardiac activity, second body movement, and/or spectral analysis of second cardiac activity or second body movement are indicative of an epileptic event. If no, flow returns to the receiving blocks 3110-3120. If yes, an epileptic event is declared at block 3140.

Alternatively or in addition to declaring an epileptic event, further actions can be performed. In one embodiment, the method further comprises classifying the epileptic event based upon at least one of the first cardiac activity, the first body movement, the responsiveness, the awareness, the second cardiac activity, the second body movement, the spectral properties of the second cardiac activity, the spectral properties of the second body movement, and two or more thereof.

Classifications of epileptic events can be generally based on the information shown in FIGS. 25-28 and the discussion herein and in U.S. patent application Ser. No. 12/896,525, filed Oct. 1, 2010. Classifications can also be based in part on observations of stereotypical seizures of a particular patient. Not all seizures that a clinician would recognize as being of a particular type may exhibit all the properties discussed herein, and thus, not all may be amenable to classification by the methods described herein, but a substantial majority are expected to be amenable to classification by the methods described herein.

In one embodiment, the epileptic event is classified as a generalized tonic-clonic seizure when the following occur in a patient in a first, non-recumbent position: the first body movement comprises a fall from the first, non-recumbent position, wherein (i) the fall is associated with a loss of responsiveness, a loss of awareness, or both; and (ii) the fall is followed by generalized body movements.

Falls to the ground associated with a primarily or secondarily generalized tonic-clonic, generalized tonic, generalized clonic-tonic-clonic seizure or generalized atonic seizure are distinguishable from those caused by tripping or slipping by the absence of protective/defensive actions (e.g., breaking the fall with the arms) and other features such which body part(s) is(are) first on contact with the ground.

Primarily generalized seizures usually result in synchronous bilateral movements of equal amplitude, with maintenance of head and eyes on the midline. Secondarily generalized seizures usually manifest at onset with unilateral movements of limbs, head, eyes, or trunk.

In one embodiment, the generalized body movement comprises a rhythmic body movement. Alternatively or additionally, the generalized body movements can comprise flexion and extension of joints and/or can have a frequency of about 3 Hz at some time during the epileptic event. In another embodiment, the rhythmic movement is temporally associated with an epileptiform discharge.

Body movement can allow classification of an epileptic event as to primarily generalized or secondarily generalized. Specifically, the epileptic event can be classified as primarily generalized if body movements are synchronous and of equal amplitude on both sides of the body, and as secondarily generalized if not.

In a further embodiment, the epileptic event is classified as a generalized tonic-clonic seizure when recovery of awareness follows recovery of responsiveness, provided at least one of the key identifiers (e.g., loss of postural tone or diffuse increase in muscle tone or rhythmical body movements) have occurred.

In one embodiment, the epileptic event is classified as an atonic seizure when the following occur in a patient in a first, non-recumbent position: i) a body movement comprises a fall from the first, non-recumbent position, wherein the fall is associated with a loss of responsiveness, a loss of awareness, or both; and/or (ii) the patient shows a significant reduction in body movements below a reference value after the fall, a significant reduction in muscle tone below a reference value after the fall, or both.

Typically, the significant reductions in body movements and/or muscle tone commonly seen in atonic seizures are not caused by changes in heart or respiratory activity.

In one embodiment, the epileptic event is classified as tonic when the following occur to a patient in a first, non-recumbent position: an increase in muscle tone above a reference value, a loss of responsiveness, and an absence of generalized movements.

In a further embodiment, the epileptic event is classified as tonic when recovery of awareness follows recovery of responsiveness, provided it has been associated with loss of responsiveness or awareness.

In one embodiment, the epileptic event is classified as a complex partial seizure based upon a finding the patient's cardiac activity is associated with impaired awareness and is not associated with a fall or at some point in time with generalized rhythmical body movements; and the epileptic event is classified as a simple partial seizure based upon a finding the patient's cardiac activity is not associated with impaired awareness and is not associated with generalized rhythmical body movements.

In one embodiment, the event is classified as syncope, when at least one of the following occur: the body movement comprises a fall from a non-recumbent position and the fall is associated with a loss of responsiveness or a loss of awareness, and recovery of responsiveness or recovery of awareness occurs immediately after the fall, or when the body movement comprises a fall from a recumbent position, there is marked decrease in heart rate or a brief transient cessation of heart beats (asystole).

Epileptic events can be determined or classified in view of the patient's body position. For example, an epileptic event when the patient is in a decubitus position (lying down) may be determined from an observation of transient loss of muscle tone in antigravitatory muscles (e.g., paraspinal; quadriceps), followed by transient increase in muscle tone in agonist and antagonist muscle groups (e.g., paraspinal and abdominal recti; quadriceps and hamstrings), which in turn is followed by generalized rhythmical muscle contractions (typically with a frequency of 3 Hz and/or 10-12 Hz at some time during the event).

For another example, an epileptic event when the patient is in a seated position may be determined using both electromyography (EMG) signals and accelerometer signals.

The one or more of the first cardiac activity, the second cardiac activity, the first body movement, the second body movement, the responsiveness, and the awareness can be provided by any known technique. In one embodiment, at least one of the first cardiac activity and the second cardiac activity is sensed by at least one of an electrocardiogram (EKG), phonocardiogram (PKG), apexcardiography, blood pressure monitor, and echocardiography. The body movement can be sensed by any known technique. In one embodiment, at least one of the first body movement and the second body movement is sensed by an accelerometer, an inclinometer, an actigraph, an imaging system, a dynamometer, a gyroscope, electromyography (EMG), or two or more thereof.

In certain circumstances, the method can make a false positive determination of an epileptic event, i.e., determine an epileptic event based on the signals and tests described above when no epileptic event (as may be determined using direct/invasive recording of electrical activity at/near the epileptogenic zone, observation by a skilled practitioner, or other techniques known to the person of ordinary skill in the art) occurred. In one embodiment, the method further comprises receiving an indication that the determined epileptic event was not an actual epileptic event. Such indications may include, but are not limited to, the first body movement is a fall but the fall is not characteristic of an epileptic fall; the generalized body movements are not rhythmical and bilaterally synchronous; the generalized body movement have a frequency substantially different from 3 Hz or a variable frequency; the generalized body movements change direction, pairs of agonist-antagonist muscles, and/or movements in different directions occur simultaneously in two or more joints; the change in cardiac activity, cardiac activity morphology, cardiac spectral analysis, apexcardiography, or echocardiography is not characteristic of epileptic seizures.

Similarly, in one embodiment, the method further comprises receiving an indication of a false negative, i.e., an indication an epileptic event occurred but no determination thereof was made.

The indication may be based at least in part on input from the patient, a caregiver, or a medical professional, and/or on quantification or characterization of one or more body signals. The indication may be provided at the time of the false determination or later.

A false determination (whether positive or negative) may render it appropriate to modify the body signals or analyses used in making future determinations. In one embodiment, the method further comprises reducing a likelihood of a future determination of a false positive epileptic event based at least in part on one or more of the first cardiac activity, the first body movement, the responsiveness, the awareness, the second cardiac activity, the second body movement, the spectral analysis of the second cardiac activity, or the spectral analysis of the second body movement, in response to the indication. In another embodiment, the method further comprises reducing a likelihood of a future determination of a false negative epileptic event based at least in part on one or more of the first cardiac activity, the first body movement, the responsiveness, the awareness, the second cardiac activity, the second body movement, the spectral analysis of the second cardiac activity, or the spectral analysis of the second body movement, in response to the indication.

When an epileptic event is determined, the method can further comprise one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure; identifying the end of the seizure; and assessing the patient's post-ictal impairment or recovery from the seizure. "Recovery" is used herein to encompass a time after seizure onset and/or seizure end when the patient's parameters are returning to baseline. Other examples include, but are not limited to, logging one or more of a time of onset of the epileptic event, a time of termination of the epileptic event, a severity of the epileptic event, an impact of the epileptic event, an interval between the epileptic event and the most recent preceding epileptic event, an epileptic event frequency over a time window, an epileptic event burden over a time window, time spent in epileptic events over a time window, or a type of epileptic event.

To reduce the rate of false positive detections or for other reasons, in one embodiment, the method further comprises recording one or more of the patient's reference body movement or movements, reference cardiac activity, reference responsiveness level, reference awareness level, reference cardiac activity, reference spectral analysis of the cardiac activity, and/or reference spectral analysis of the body movement during one or more interictal activities at one or more times when the patient is not suffering an epileptic event, to yield recorded data not associated with an epileptic event; defining one or more interictal activity reference characteristics from the recorded data; and/or overruling the determination of the epileptic event based at least in part on finding the patient's first body movement, first cardiac activity, responsiveness level, awareness level, second cardiac activity, second body movement, spectral analysis of the second cardiac activity, and/or spectral analysis of the second body movement matches the one or more interictal event reference characteristics.

The interictal activities at one or more times when the patient is not suffering an epileptic event can include different activities (e.g., walking vs. running vs. swimming, etc.), and can alternatively or in addition include the same activity at different times of day, week, month, or year, and/or under different external circumstances (e.g., walking at sea level vs. walking at higher altitude, etc.).

The overruling of a determination of an epileptic event may be made with some probability between zero and one. The overruling may be made according to a permanent or semipermanent rule or on a case-by-case basis. The references may be stored in a library on a per-patient, per-seizure type, or per-population basis.

In one embodiment, the overruling may involve the triggering of one or more additional test(s). Such further triggering may allow more accurate determination of epileptic events.

Recording one or more of the patient's reference body movement or movements, reference cardiac activity, reference responsiveness level, reference awareness level, reference cardiac activity, reference spectral analysis of the cardiac activity, or reference spectral analysis of the body movement during epileptic event may allow overruling of false negative or false positive determinations.

The body movement during one or more interictal activities can include at least one of a movement of a part of the body (e.g., the eyes or eyelids), a movement of a limb (e.g., an arm), a movement of a part of a limb (e.g., a wrist), a direction of a movement, a velocity of a movement, a force of a movement, an acceleration of a movement, a quality of a movement, an aiming precision of a movement, or a purpose or lack thereof of a movement.

The likelihood of a patient suffering an epileptic event may change at different times and/or under different conditions. In one embodiment, a plurality of interictal event reference characteristics are defined which differ from one another based on one or more of the time of day of the recording, the time of week of the recording, the time of month of the recording, the time of year of the recording, the type of activity, changes in the patient's body weight or body mass index, changes in the patient's medication, changes in the patient's physical fitness or body integrity, state of physical or mental health, mood level or changes in the patient's mobility. Alternatively or in addition, a plurality of interictal event reference characteristics in a female patient can be defined in reference to the menstrual cycle and/or to pregnancy. Alternatively or in addition, changes in the patient's environment may change the likelihood of the patient suffering an epileptic event.

In a further embodiment, the overruling is based at least in part on one or more of the plurality of interictal event reference characteristics.

Any characteristic of the one or more interictal events may be considered. In one embodiment, the one or more characteristics are patterns or templates.

It may be desirable in certain embodiments to adapt at least one of a reference value on one or more of the body movement, the cardiac activity, the responsiveness level, the awareness level, the second cardiac activity, the second body movement, and the spectral analysis of cardiac activity or body movement, based upon one or more determinations that the specificity of past detections was above or below a specificity measure, the sensitivity of past detections was above or below a sensitivity measure, the speed of detection defined as the time elapsed between the occurrence of the first body signal change indicative of the onset of the seizure and the issuance of the detection, the cost of the therapy was below or above a cost measure, the patient's tolerance of the therapy was below an acceptable tolerance, the adverse effects were above an acceptable level, or the patient's disease state was below or above a first disease state threshold. Positive predictive value or negative predictive value may be used in addition to or instead of specificity or sensitivity.

As should be apparent, a single "threshold" can be mathematically defined in a number of ways that may be above or below a particular value of a particular parameter. For example, an elevated heart rate can be defined, with equal validity, as a heart rate above a threshold in units of beats/unit time or an interbeat interval below a threshold in units of time. More than one "threshold" may be used to optimize specificity, sensitivity or speed of detection.

For example, the method can further comprise determining one or more of a specificity of past detections, a sensitivity of past detections, a speed of past detections, a cost of a therapy for epileptic events, a patient's tolerance of a therapy for epileptic events, and a disease state of the patient; and/or loosening at least one constraint on one or more of the body movement, the cardiac activity, the responsiveness test, the awareness test, the second cardiac activity test, the second body movement test, and the spectral analysis of second cardiac activity or second body movement based upon one or more determinations that the specificity of past detections was above a first specificity threshold, the sensitivity of past detections was below a first sensitivity threshold, the speed of detection was below a first speed of detection threshold, the cost of the therapy was below a first cost threshold, the patient's tolerance of the therapy was below a first tolerance threshold (i.e., the patient can tolerate more detections or actions performed in response to detections), and/or the patient's disease state was below a first disease state threshold; or tightening the at least one constraint based upon one or more determinations that the specificity of past detections was below a second specificity threshold, the sensitivity of past detections was above a second sensitivity threshold, the speed of detection was above an acceptable threshold for efficacy of therapy and safety of the patient, the cost of the therapy was above a second cost threshold, the patient's tolerance of the therapy was above a second tolerance threshold (i.e., the patient cannot tolerate more detections or actions performed in response to detections), and/or the patient's disease state was above a second disease state threshold.

In another embodiment, the disclosure can be used for the detection of generalized tonic-clonic seizures. A "generalized tonic-clonic seizure" is used herein to refer to a primarily or secondarily generalized seizure that features at least one tonic, clonic, or both tonic and clonic phase. Myoclonic seizures are included in this definition. At onset or at some point during the generalized tonic-clonic seizure, at least a majority of the body muscles or joints are involved. "Body muscle" is used herein to refer to those capable of moving joints, as well as muscles of the eyes, face, orolaryngeal, pharyngeal, abdominal, and respiratory systems.

In one embodiment, the present disclosure relates to a method, comprising: receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and/or a spectral analysis signal relating to the second body movement; determining an occurrence of a generalized tonic-clonic epileptic seizure, the determination being based upon the correlation of at least two features, at least one feature being of each of the at least two body signals, wherein: the feature of the first cardiac activity signal is an increase in the patient's heart rate above an interictal reference value; the feature of the first body movement signal is at least one of (i) an increase in axial or limb muscle tone substantially above an interictal or exercise value for the patient, (ii) a decrease in axial muscle tone in a non-recumbent patient, below the value associated with a first, non-recumbent position, (iii) fall followed by an increase in body muscle tone, and/or (iv) a fall followed by generalized body movements; the feature of the responsiveness signal is a decrease in the patient's responsiveness below an interictal reference value; the feature of the awareness signal is a decrease in the patient's awareness below an interictal reference value; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; or the feature of the spectral analysis signal of the second body movement is a correlation with an ictal body movement spectral analysis reference signal; and/or performing a further action in response to the determination of the occurrence of the epileptic event.

Figure 32:
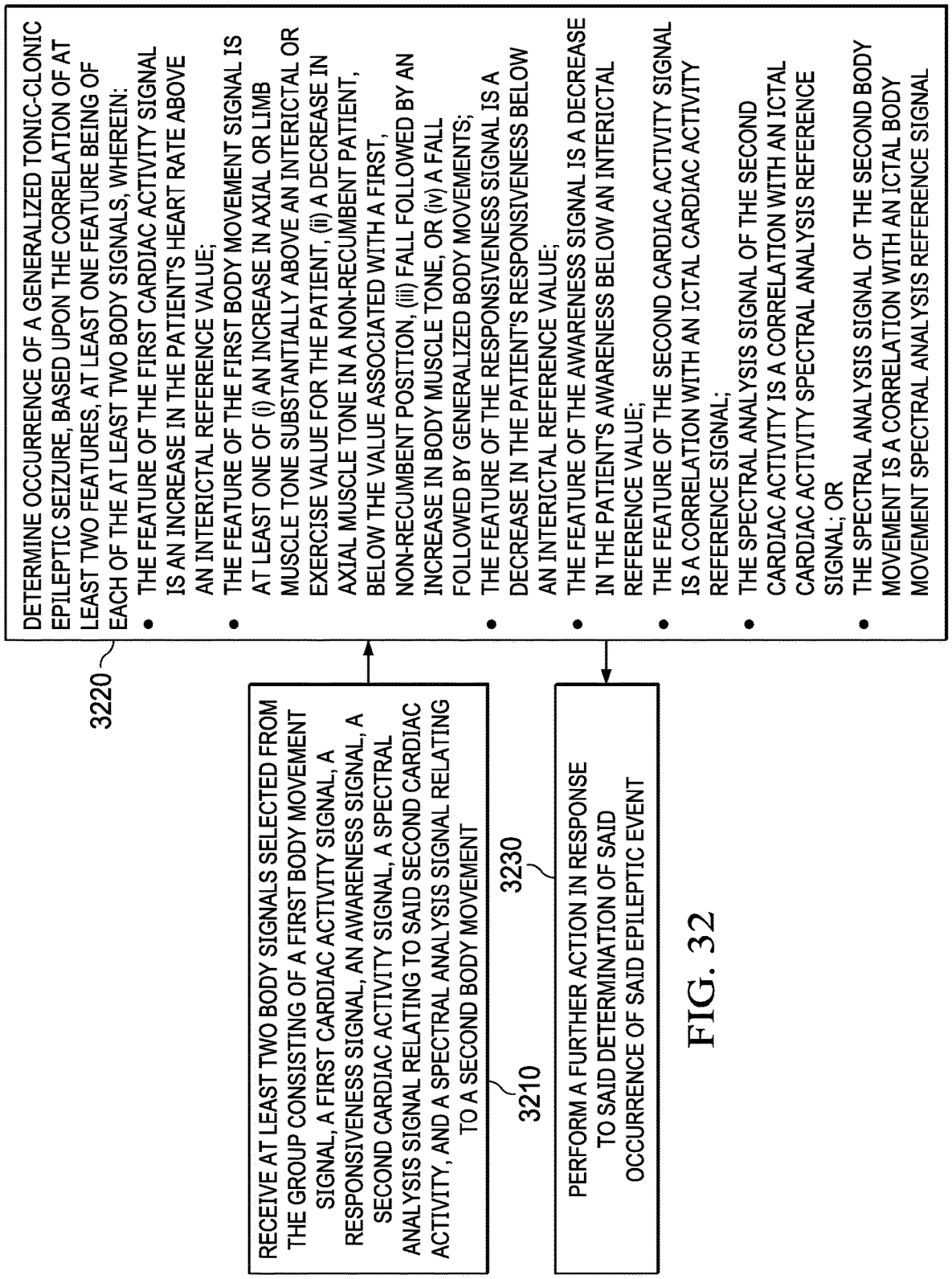
FIG. 32 shows a flowchart of an implementation of a method according to one embodiment of the present disclosure.

FIG. 32 depicts one embodiment of this method. FIG. 32 depicts a receiving step 3210, a determining step 3220, and a performing step 3230.

In one embodiment, the correlation has a high absolute value and is either positive or negative. E.g. the correlation may be positive, such as with a value greater than 0.7, 0.75, 0.8, 0.85, 0.9, or 0.95, or negative, such as with a value less than −0.7, −0.75, −0.8, −0.85, −0.9, or −0.95.

The further action may comprise one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure, identifying the end of the seizure; and assessing the patient's post-ictal impairment or recovery from the seizure.

The various signals can be provided by any appropriate technique and their features referred to above can likewise be measured as a routine matter for the person of ordinary skill in the art having the benefit of the present disclosure. For example, in one embodiment, the correlation of the second cardiac activity signal with the ictal cardiac activity reference signal comprises a match to an ictal cardiac activity template; the correlation of the second body movement signal with the ictal body movement reference signal comprises a match to an ictal body movement template; the correlation of the spectral analysis signal of the second cardiac activity with the ictal cardiac activity spectral analysis reference signal comprises a match to an ictal cardiac activity spectral analysis pattern or template; and/or the correlation of the spectral analysis signal of the second body movement with the ictal body movement spectral analysis reference signal comprises a match to an ictal body movement spectral analysis pattern or template. Aspects of the signals and their features may include, among others, a body movement signal further comprising an indication of a fall prior to the indication of the tonic or clonic activity.

In one embodiment, a tonic-clonic seizure can be further characterized as secondarily generalized if the first body movement signal does not comprise synchronous movement of all body muscles with equal amplitude or velocity prior to an indication of tonic or clonic activity.

In one embodiment, the end of the generalized tonic-clonic epileptic seizure can be indicated when at least one of the body signals trends toward an interictal reference value, range, or pattern of the body signal.

In one embodiment, the method further comprises indicating the beginning of a post-ictal period based upon the appearance of at least one post-ictal feature of at least one the body signal, wherein: the post-ictal feature of the first cardiac signal or the second cardiac signal is a decrease in the patient's heart rate below an ictal reference value; the post-ictal feature of the first body movement signal or the second body movement signal is a decrease in the patient's muscle tone or movement below an ictal reference value; the post-ictal feature of the responsiveness signal is an increase in the patient's responsiveness above an ictal value and below an inter-ictal reference value; and/or the post-ictal feature of the awareness signal is an increase in the patient's awareness above an ictal value and below an inter-ictal reference value.

The term "post-ictal," is not necessarily limited to the period of time immediately after the end of the primarily or secondarily generalized tonic-clonic epileptic seizure and is not limited to this type of seizure but also encompasses partial seizures (e.g., all complex and certain simple partial and absence seizures). Rather, it refers to the period of time during which at least one signal has one or more features that differs from the ictal and inter-ictal reference values that indicates one or more of the patient's body systems are not functioning normally (e.g., as a result of the seizure or of an injury suffered during the seizure) but are not exhibiting features indicative of a seizure.

In one embodiment, the end of the post-ictal period can be indicated when each of the post-ictal features is outside the range of values associated with the ictal and post-ictal states. In another embodiment, the end of the post-ictal period can be indicated when at least one of the post-ictal features is outside the range of values associated with the ictal and post-ictal states. In this embodiment, the onset and termination of the post-ictal period may be partial when all features have not returned to interictal reference values or complete when all features have. This distinction (partial vs. complete) has important therapeutic (the patient may require treatment until all body signals have fully recovered to inter-ictal values), safety (the patient's mortality and morbidity risks may remain increased until all body signal have fully recovered to inter-ictal values) and predictive implications (the probability of occurrence of the next seizure and time to it (inter-seizure interval) may depend on recovery of one more body signals to their interictal value.

It should also be borne in mind that different features are expected to return to their interictal reference values at different times. For example, from kinetic and brain electrical perspectives, a seizure can be defined as having ended when abnormal movements and abnormal EEG cease. These events typically take place before the patient's heart rate returns to baseline. Further, it may take a few minutes after abnormal movements and abnormal EEG end for cognition and responsiveness to return to baseline; up to about 30 min for awareness to return to baseline; and about 30-45 minutes for blood lactic acid concentration to return to baseline. Temporal relationships between changes in signal features, and transitions from one state to another, are generally described in U.S. patent application Ser. No. 12/896,525, filed Oct. 1, 2010. Transitions may have quantifiable differences in location as well, e.g., the number of either brain sites or body organs in which the transition has taken place may vary over time (e.g., an ictal change first occurring on the right mesiotemporal lobe, or a change in heart activity at or near seizure onset followed by changes in metabolic indices.

In another embodiment, the present disclosure relates to the detection of partial seizures. In one embodiment, the present disclosure relates to a method, comprising: receiving at least two body signals selected from the group consisting of a signal relating to a first body movement, a signal relating to a first cardiac activity, a responsiveness signal, an awareness signal, a signal relating to a second cardiac activity, a signal relating to a second body movement, a spectral analysis signal relating to the second cardiac activity, and spectral analysis signal relating to the second body movement; and determining an occurrence of a partial epileptic seizure based upon a correlation of two features, at least one feature being of each of the at least two body signals, wherein: the feature of the first cardiac signal is a value outside an interictal reference value range; the feature of the first body movement signal is a body movement associated with a partial seizure; the feature of the second cardiac activity signal is a correlation with an ictal cardiac activity reference signal; the feature of the second body movement signal is a correlation with an ictal body movement reference signal; the feature of the spectral analysis signal of the second cardiac activity is a correlation with an ictal cardiac activity spectral analysis reference signal; and/or the feature of the spectral analysis signal of the second body movement is a correlation with an ictal body movement spectral analysis reference signal; and/or performing a further action in response to the determination of the occurrence of the epileptic event.

Figure 33:
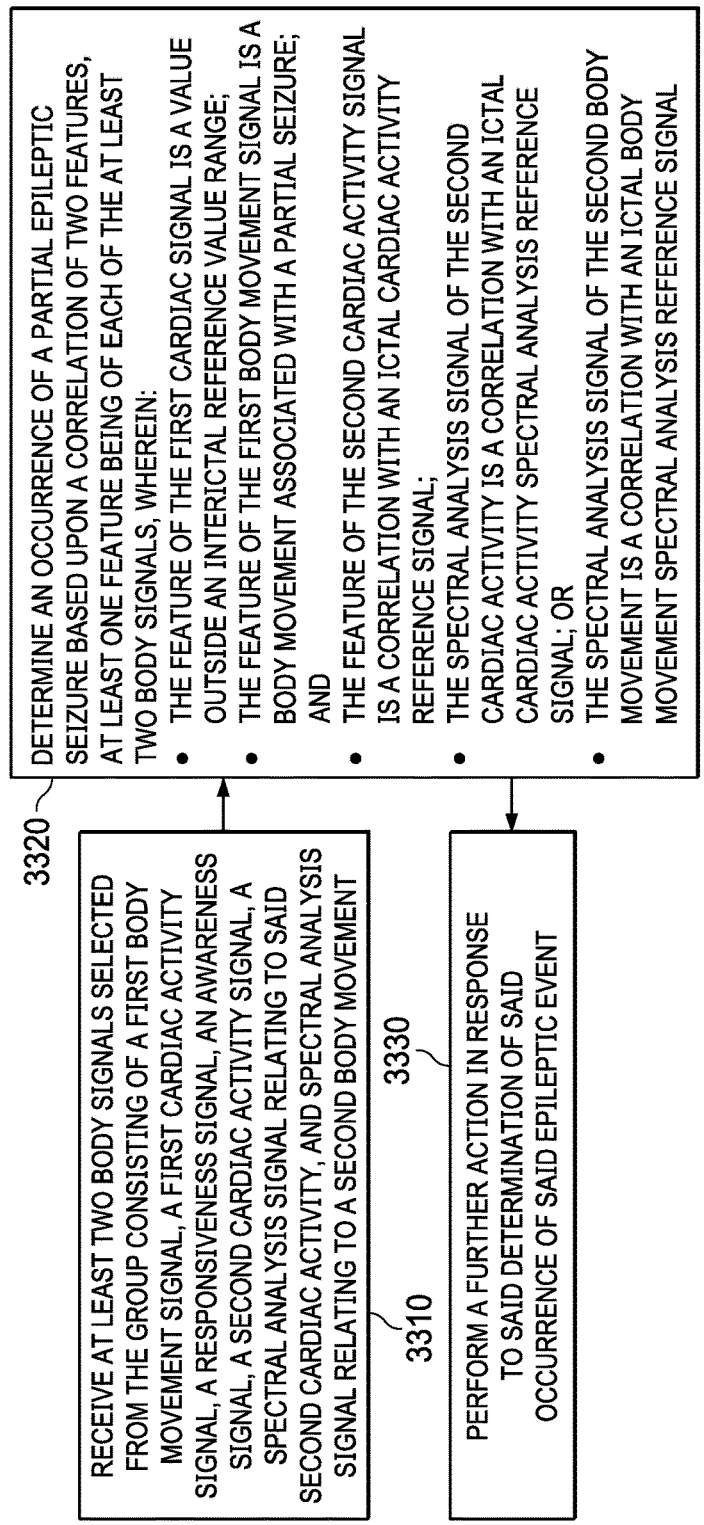
FIG. 33 shows a flowchart of an implementation of a method according to one embodiment of the present disclosure.

FIG. 33 depicts one embodiment of this method. FIG. 33 depicts a receiving step 3310, a determining step 3320, and a performing step 3330.

The various signals can be provided by any appropriate technique and their features referred to above can likewise be measured as a routine matter for the person of ordinary skill in the art having the benefit of the present disclosure. For example, in one embodiment, the correlation of the second cardiac activity signal with the ictal cardiac activity reference signal comprises a match to an ictal cardiac activity template; the correlation of the second body movement signal with the ictal body movement reference signal comprises a match to an ictal body movement template; the correlation of the spectral analysis signal of the second cardiac activity with the ictal cardiac activity spectral analysis reference signal comprises a match to an ictal cardiac activity spectral analysis pattern or template; and/or the correlation of the spectral analysis signal of the second body movement with the ictal body movement spectral analysis reference signal comprises a match to an ictal body movement spectral analysis pattern or template.

Matches to patterns and templates are described in U.S. patent application Ser. No. 12/884,051, filed Sep. 16, 2010. A "match" should not be construed as requiring a complete or perfect fit to a pattern or template.

In one embodiment, the further action comprises one or more of logging the occurrence and/or time of occurrence of the seizure; providing a warning, alarm or alert to the patient, a caregiver or a health care provider; providing a therapy to prevent, abort, and/or reduce the severity of the seizure; assessing one or more patient parameters such as awareness or responsiveness during the seizure; assessing the severity of the seizure, identifying the end of the seizure; and assessing the patient's post-ictal impairment or recovery from the seizure.

Partial seizures generally result in body movements that do not include falls.

The partial seizure can be classified as complex if at least one of the features of the awareness signal is a decrease in the patient's awareness below its reference value, or as (ii) simple if there is no decrease in the patient's awareness below its reference value, or if there is a decrease in the patient's responsiveness but awareness remains at an inter-ictal value.

In one embodiment, the end of the partial epileptic seizure can be indicated when at least one of the features of the respective body signals is outside the range of values associated with the ictal state for that body signal. In another embodiment, the end of the partial epileptic seizure can be indicated when each of the features of the respective body signals trends toward an interictal reference value, range, or pattern of the body signal.

In one embodiment, the method further comprises indicating the beginning of a post-ictal period when at least one of the body signals is outside the range of values associated with the ictal and inter-ictal states for that body signal, wherein: the post-ictal feature of the cardiac signal is a heart rate outside the range of values associated with the ictal state; the post-ictal feature of the body movement signal is a change in the patient's movement outside the ictal range of values; the post-ictal feature of the responsiveness signal is an increase in the patient's responsiveness above an ictal reference value but remaining below an inter-ictal reference value; and/or the post-ictal feature of the awareness signal is an increase in the patient's awareness above an ictal reference value but remaining below an inter-ictal reference value.

In one embodiment, the end of the post-ictal period can be indicated when at least one of the post-ictal features is absent from its respective body signal.

In one embodiment, such responsive action(s) may be taken if the ictal or postictal state's severity exceeds a threshold, e.g., the 90th percentile values for a patient.

Various responsive actions, such as warning, logging, and treating, among others, are generally described in U.S. patent application Ser. No. 12/896,525, filed Oct. 1, 2010. A warning may be graded, e.g., a yellow light for a mild seizure, a red light for a severe one. Treating can comprise providing supporting treatment (e.g., fluids, oxygen).

Seizure severity indices may be calculated and stored by appropriate techniques and apparatus. More information on seizure severity indices is available in U.S. patent application Ser. No. 13/040,996, filed Mar. 4, 2011.

In one embodiment, the present disclosure relates to a system, comprising: at least one sensor configured to receive at least one of a signal relating to a first cardiac activity from a patient, a signal relating to a first body movement from the patient, a responsiveness signal from the patient, an awareness signal from the patient, a signal relating to a second cardiac activity of the patient, and a signal relating to a second body movement of the patient; a detection unit configured to receive the at least one signal from the at least one sensor and determine an occurrence of an epileptic event; and/or an action unit configured to receive an indication of the occurrence of the epileptic event from the detection unit and perform at least one of logging the occurrence and/or time of occurrence of the epileptic event; providing a warning, alarm or alert to the patient, a caregiver or a health care provider; providing a therapy to prevent, abort, and/or reduce the severity of the epileptic event; assessing one or more patient parameters such as awareness or responsiveness during the epileptic event; assessing the severity of the epileptic event, identifying the end of the epileptic event; and assessing the patient's post-ictal impairment or recovery from the epileptic event.

The system can further comprise other units. For example, the system can comprise a spectral analysis unit configured to generate at least one spectral analysis signal from the signal relating to the second cardiac activity and/or the signal relating to the second body movement. In this embodiment, it may be desirable for the detection unit to be further configured to receive the at least one spectral analysis signal from the spectral analysis unit.

Although not limited to the following, exemplary systems capable of implementing embodiments of the present disclosure are generally discussed below and in U.S. patent application Ser. No. 12/896,525, filed Oct. 1, 2010.

Figure 22A:
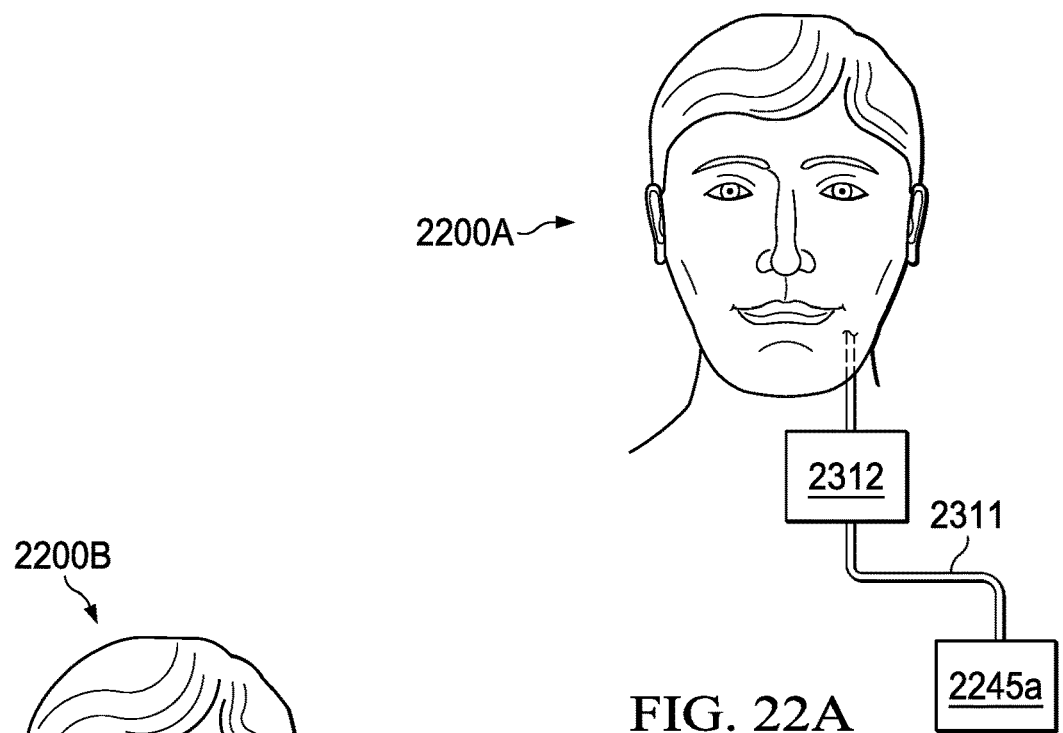
FIGS. 22A-22B provides stylized diagrams of medical devices.

FIG. 22A depicts a stylized system comprising an external unit 2245a capable of receiving, storing, communicating, and/or calculating information relating a patient's epileptic events. The system shown in FIG. 22A also includes at least one sensor 2312. The sensor 2312 may be configured to receive cardiac activity data, body movement data, responsiveness data, awareness data, or other data from the patient's body. A lead 2311 is shown allowing communication between the sensor 2312 and the external unit 2245a.

Figure 22B:
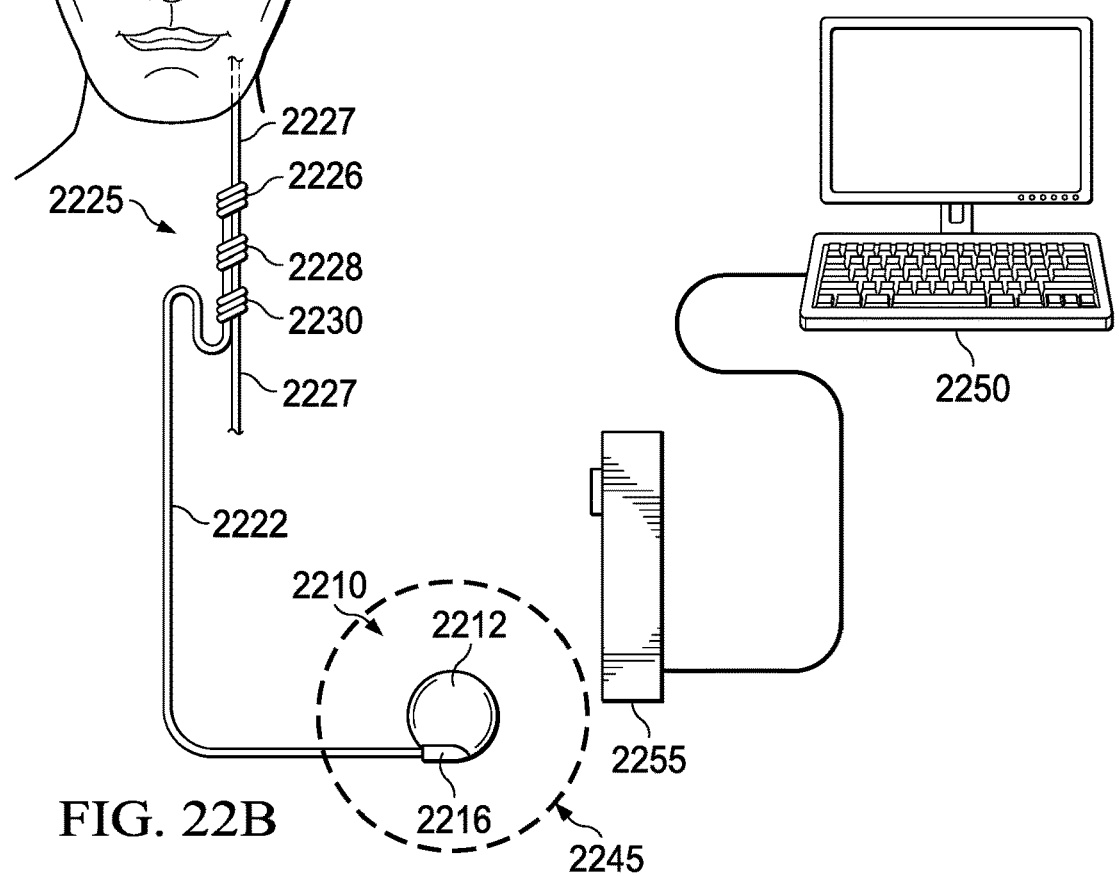

FIG. 22B depicts a stylized implantable medical system (IMD) 2200B, similar to that shown in FIG. 22A of U.S. patent application Ser. No. 12/896,525, filed Oct. 1, 2010, and discussed therein.

Figure 23:
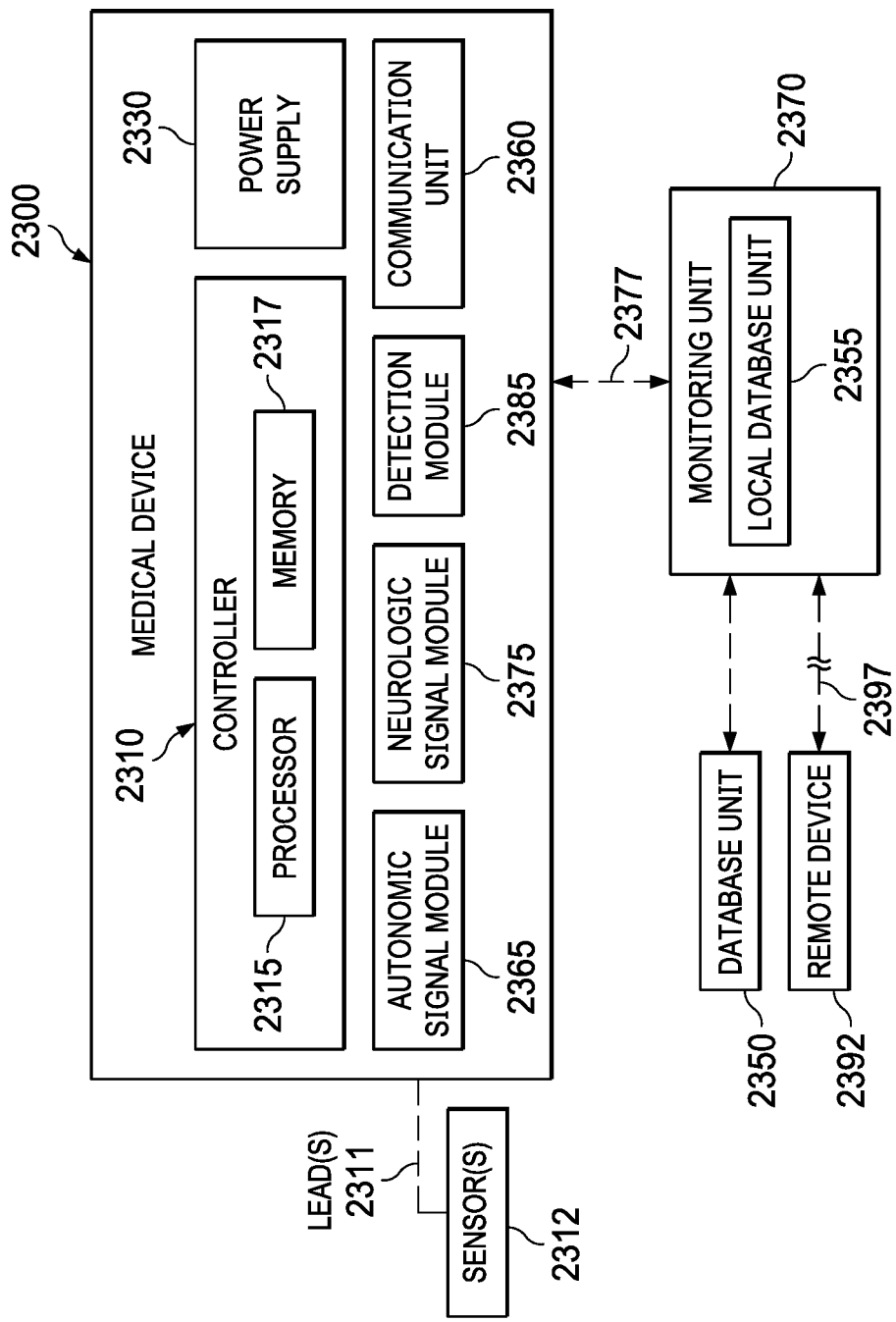
FIG. 23 provides a block diagram of a medical device system that includes a medical device and an external unit, in accordance with one illustrative embodiment of the present disclosure.

FIG. 23 is shown and generally described in U.S. patent application Ser. No. 12/896,525, filed Oct. 1, 2010. As is apparent to the person of ordinary skill in the art, the neurological signal module 2375 is capable of collecting neurological data and providing the collected neurological data to a detection module 2385.

In other embodiments (not shown), other types of signals may be collected and provided to the detection module 2385.

Figure 24A:
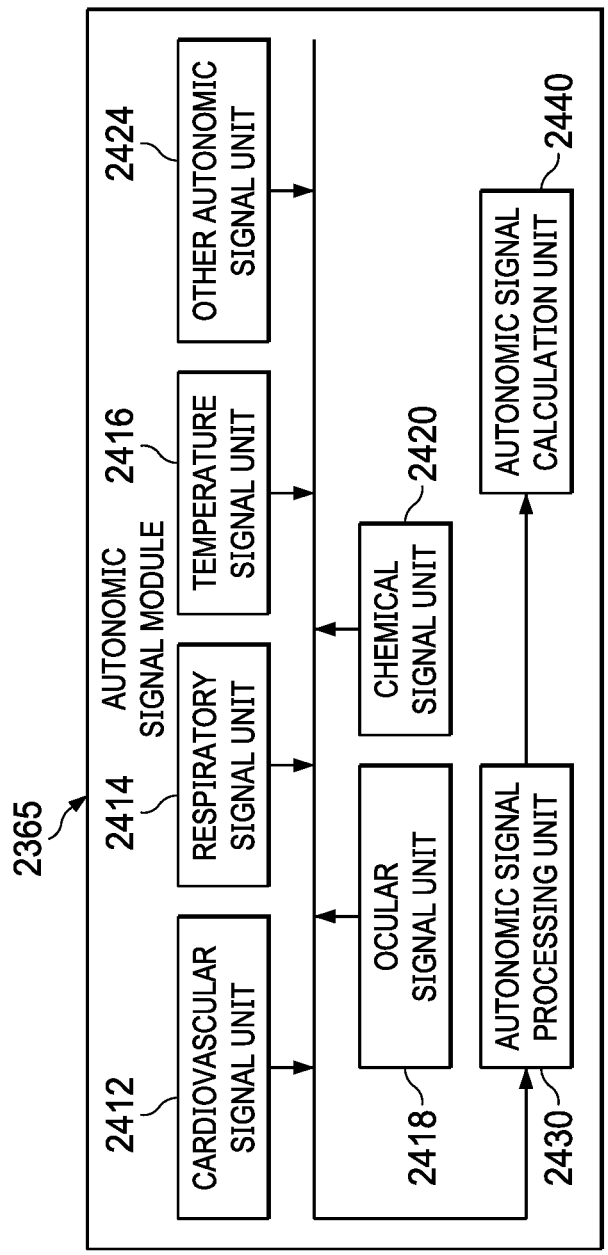
FIG. 24A provides a block diagram of a cardiac signal module of a medical device, in accordance with one illustrative embodiment of the present disclosure.
Figure 24B:
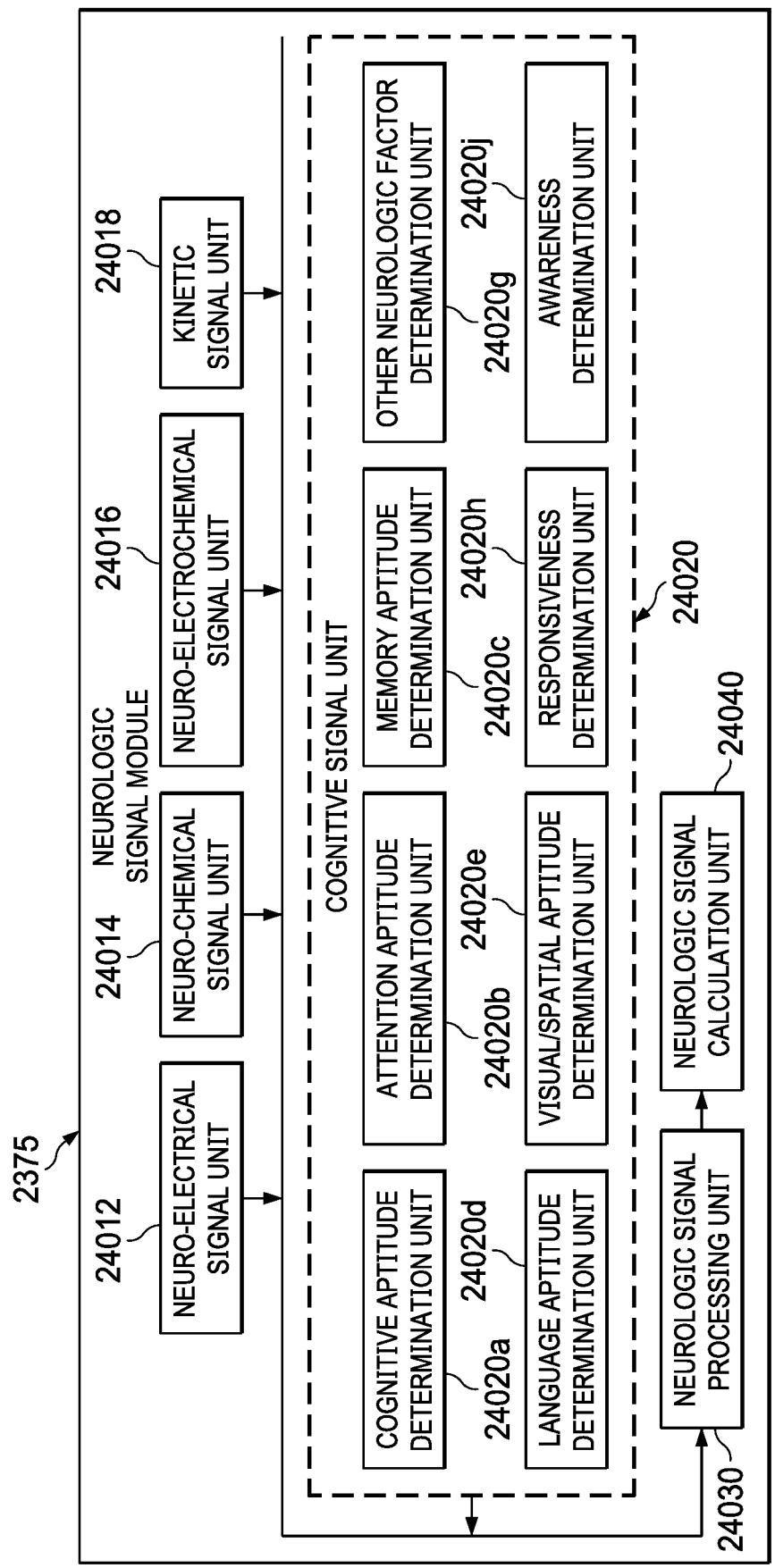
FIG. 24B provides a block diagram of a kinetic signal module of a medical device, in accordance with one illustrative embodiment of the present disclosure.

FIG. 24A and FIG. 24B are generally as shown and described in U.S. patent application Ser. No. 12/896,525, filed Oct. 1, 2010. The ocular signal unit 2418 is generally capable of providing at least one ocular signal (e.g., pupil dilation, pupillary hippus, blinking, etc.).

FIG. 24B herein also depicts an awareness determination unit 24020j.

In addition, a device can comprise other signal modules. For example, it may comprise a metabolic signal module, which can comprise a blood parameter signal unit capable of providing at least one blood parameter signal (e.g., blood glucose, blood pH, blood gas, etc.). Alternatively or in addition, the metabolic signal module can comprise a hormone signal unit capable of providing at least one hormone signal.

Figure 24C:
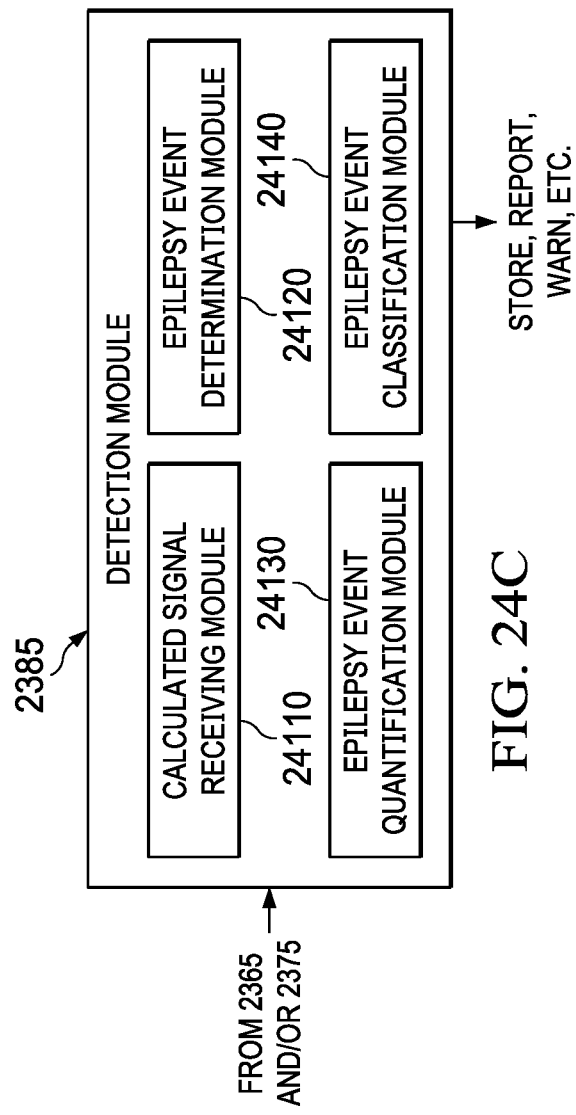
FIG. 24C provides a block diagram of a detection module of a medical device, in accordance with one illustrative embodiment of the present disclosure.
Figure 25:
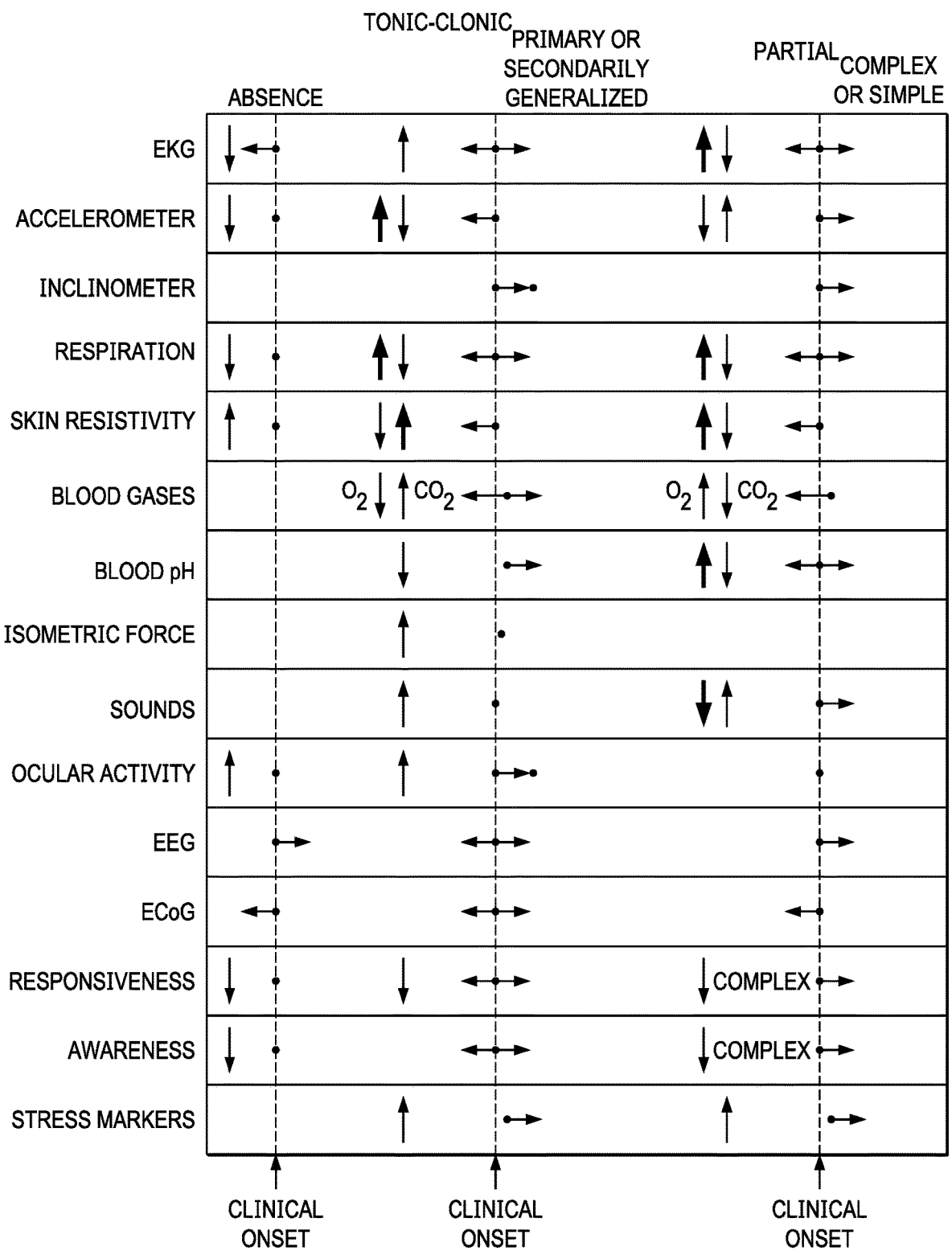
FIG. 25 shows the time of appearance (relative to clinical onset, dashed vertical line) and direction of deviations from reference activity of a plurality of body signals for four seizure types, specifically, absence seizures, tonic-clonic seizures, and simple or complex partial seizures.
Figure 26:
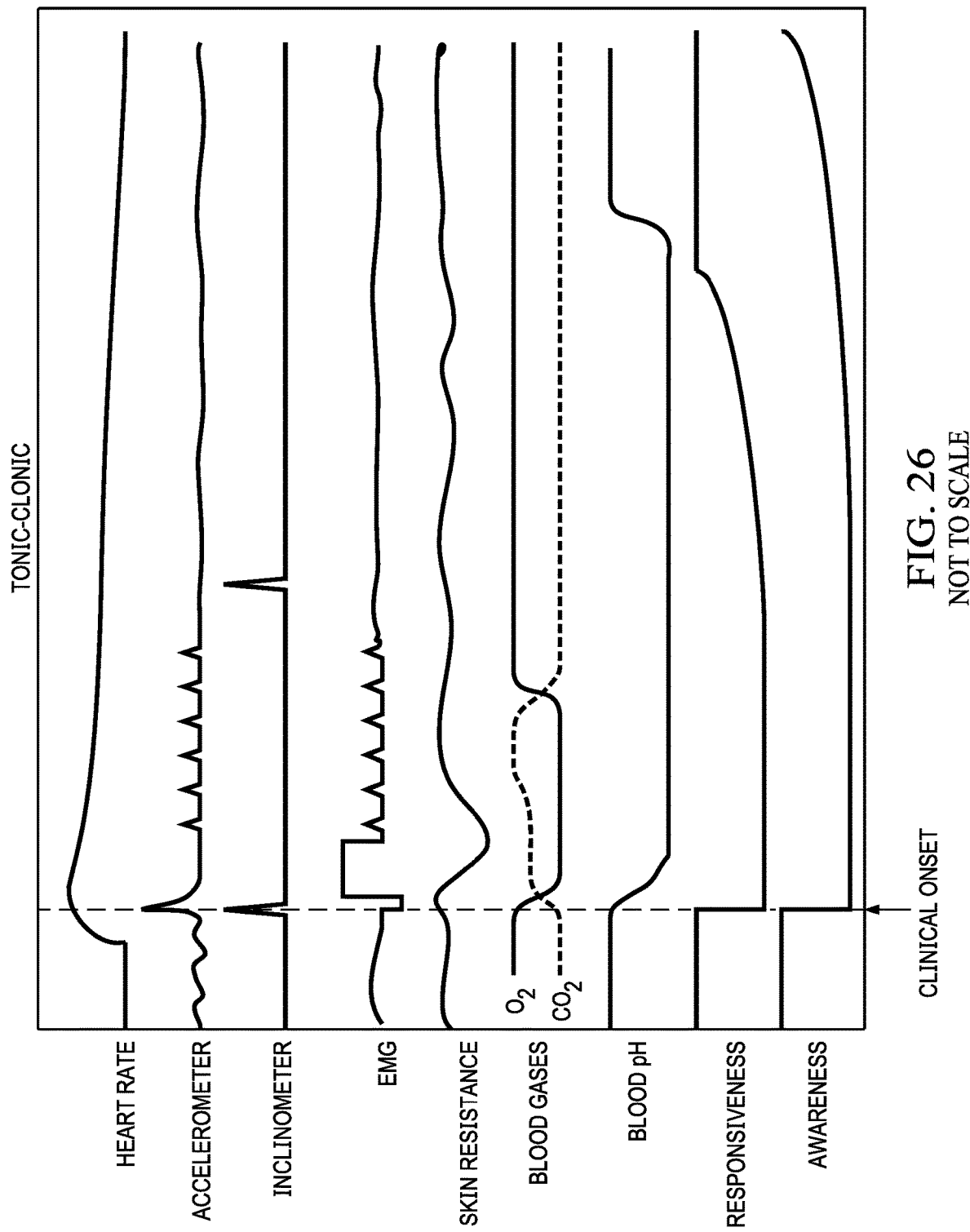
FIG. 26 shows time courses (relative to clinical onset, dashed vertical line) of activity of a plurality of body signals for tonic-clonic seizures.
Figure 27:
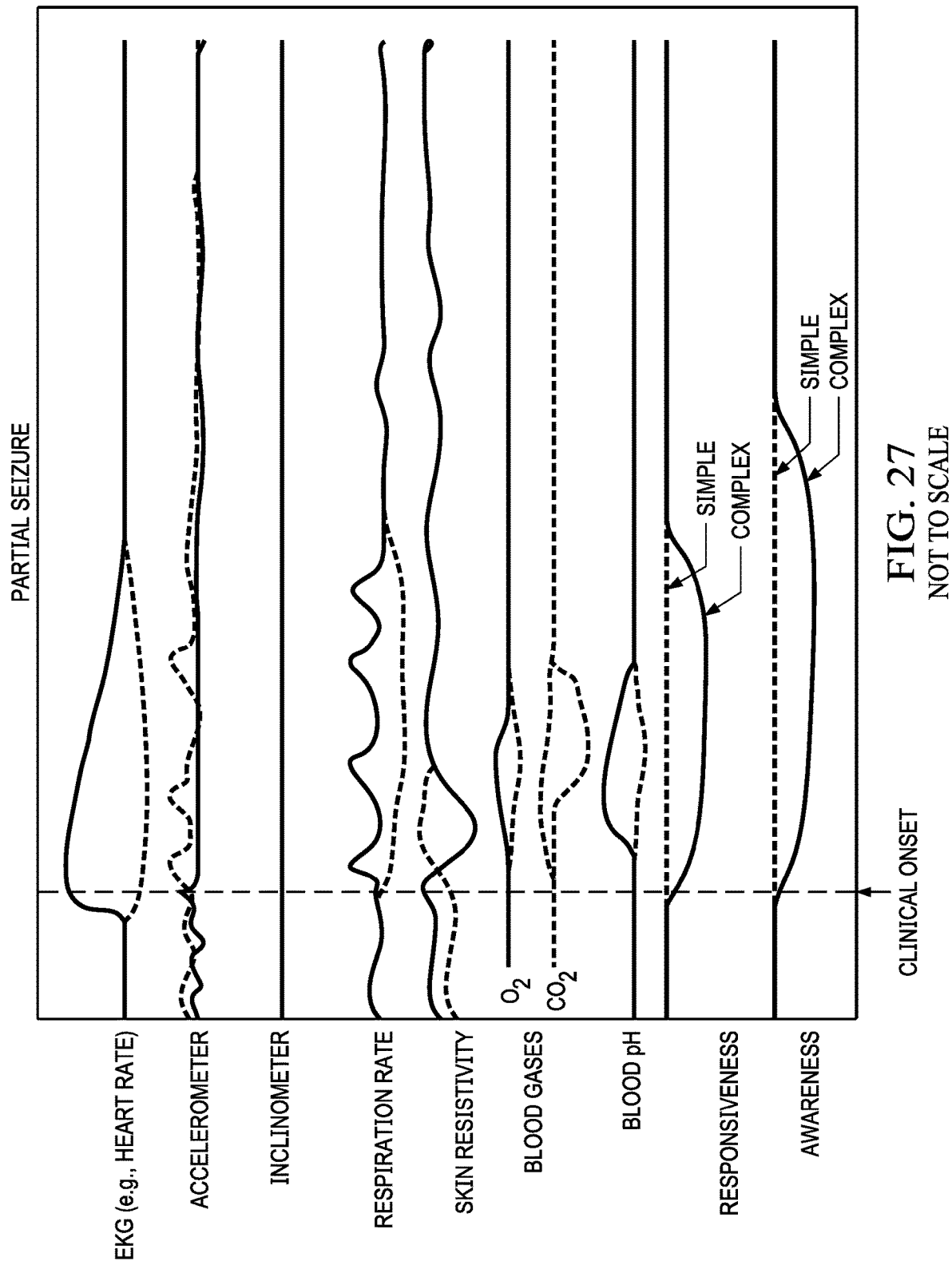
FIG. 27 shows time courses (relative to clinical onset, dashed vertical line) of activity of a plurality of body signals for partial (simple or complex) seizures.
Figure 28:
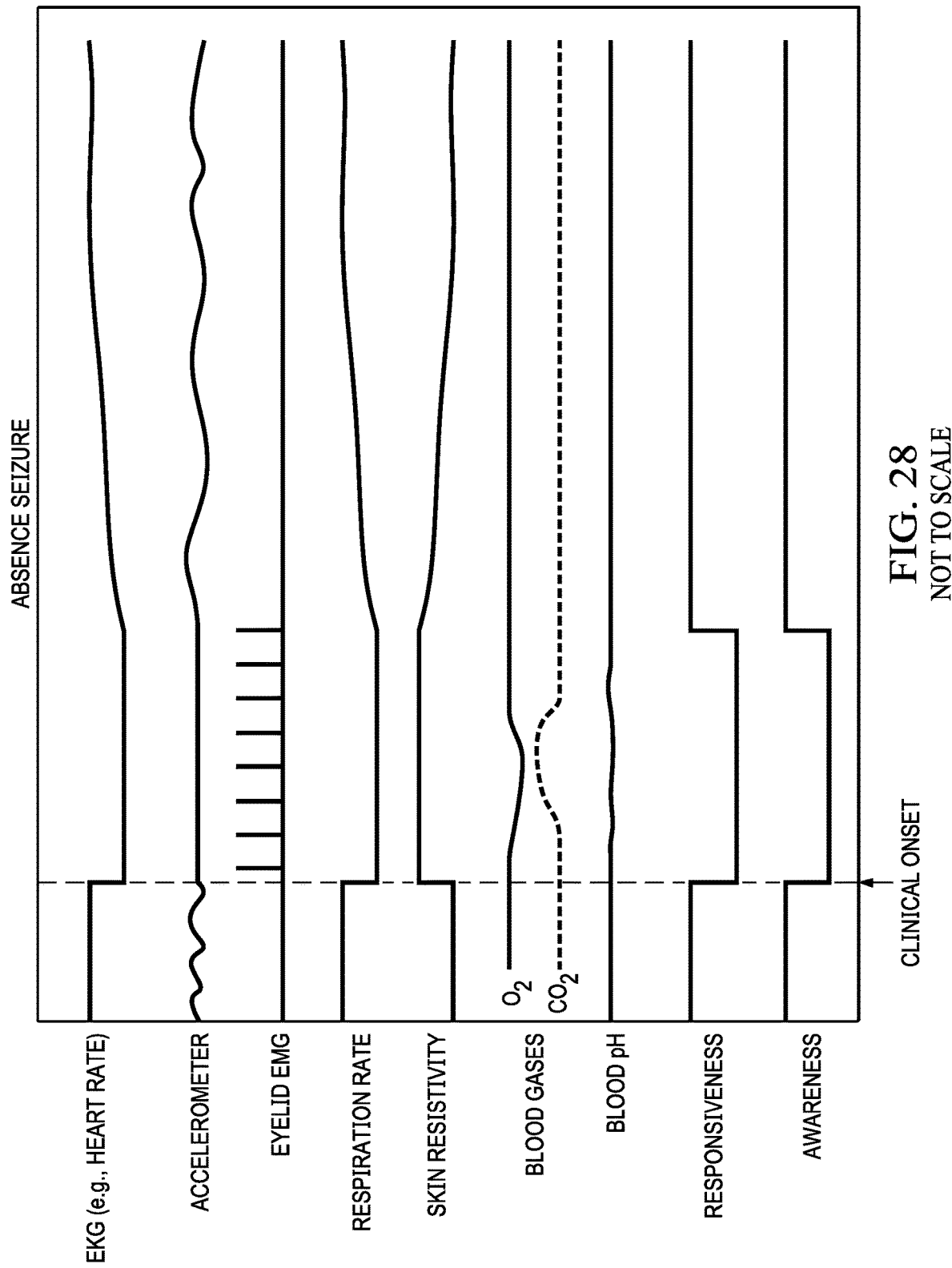
FIG. 28 shows time courses (relative to clinical onset, dashed vertical line) of activity of a plurality of body signals for idiopathic absence seizures.
Figure 29A:
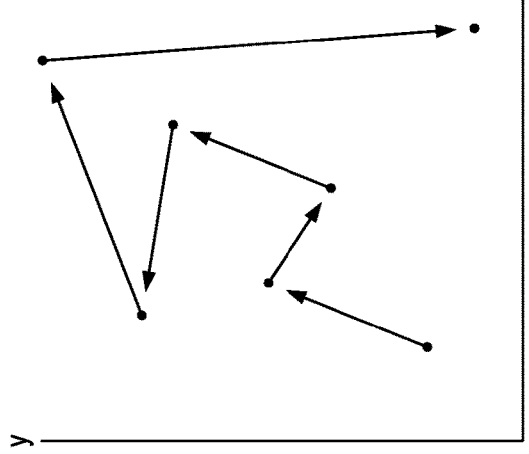
FIGS. 29A-C shows (A) an exemplary two-dimensional plot of a trajectory of epileptic movements, (B) an exemplary three-dimensional plot of epileptic movements, and (C) an additional exemplary three-dimensional plot of epileptic movements.
Figure 29C:
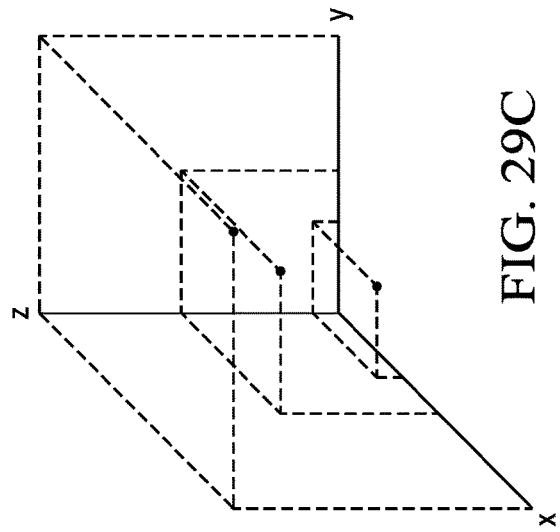
Figure 29B:
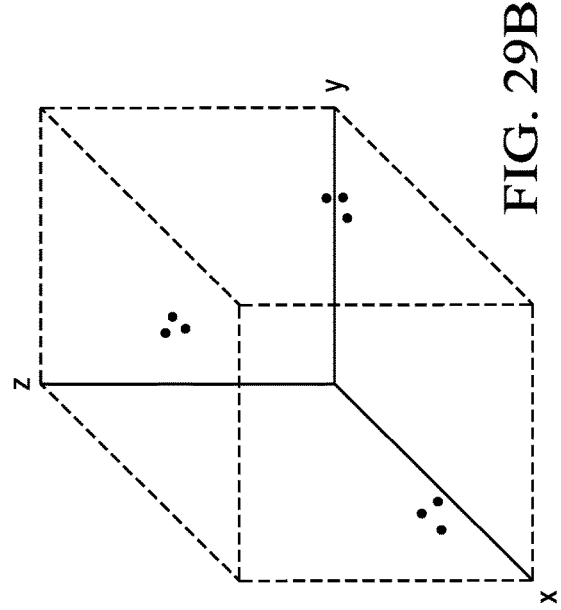
Figures 30A, 30B, 30C:
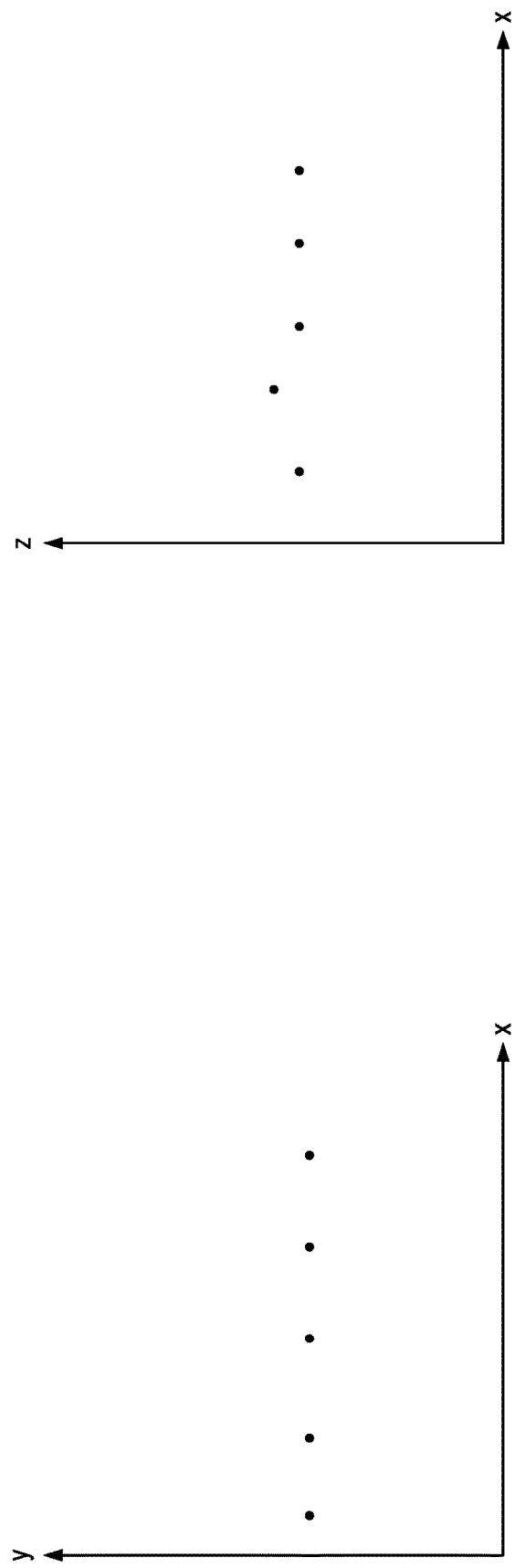
FIGS. 30A-C shows three two-dimensional, temporally cumulative plots of discrete movements during the clonic phase of a primarily or secondarily generalized tonic-clonic seizure.

A detection module 2385, as shown in FIG. 24C, is generally described in U.S. patent application Ser. No. 12/896,525, filed Oct. 1, 2010.

In one embodiment, a method of treating a medical condition in a patient using an implantable medical device where the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve the method may include receiving via one or more processors of a medical device a signal indicative of a patient's dermal activity; receiving via the one or more processors of the medical device at least one of a kinetic signal indicative of a patient's kinetic activity and a cardiac signal indicative of a patient's cardiac activity; determining via the one or more processors of the medical device a dermal activity and a dermal activity feature from the signal indicative of the patient's dermal activity, or determining at least one of a kinetic feature from the kinetic signal and a cardiac feature from the cardiac signal; detecting via the one or more processors of the medical device an onset of a seizure based on a change in the dermal activity and at least one of the kinetic feature and the cardiac feature indicative of the onset of the seizure; providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal; switching from the first polarity configuration to a second polarity configuration upon termination of the first electrical signal where the first electrode functions as the anode and the second electrode functions as the cathode in the second polarity configuration; providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal; and/or classifying an occurrence of the seizure, based at least in part on the change in the dermal activity feature, the patient's cardiac activity, or the patient's kinetic activity where the classification includes determining that the occurrence of the seizure is: an epileptic seizure or a non-epileptic seizure; a partial seizure or a partial complex seizure; and a partial seizure or a generalized seizure.

In addition, the method may include logging an occurrence of the onset of the seizure; logging a time of the occurrence of the onset of the seizure; logging a date of the occurrence of the onset of the seizure; logging a result of the classification of the seizure; providing at least one of a warning, an alarm or an alert to the patient, a caregiver or a health care provider; providing a therapy to prevent, abort, reduce a severity, or reduce a duration of the seizure; assessing at least one of an awareness or responsiveness of the patient during the seizure; assessing a severity of the seizure; determining an end of the seizure; determining a beginning of a post-ictal period; determining an end of the post-ictal period; and/or assessing a patient's post-ictal impairment or recovery from the seizure where the further action is logged into a memory. Further, the patient's cardiac activity may be one of a heart rate, a heart rate variability, a heart beat morphology, a heart sound, and/or a thoracic chest wall deflection caused by a heart's apex.

In addition, the signal indicative of the patient's cardiac activity may be provided by at least one of a force transducer, an electrocardiogram (EKG) signal, a phonocardiogram (PKG) signal, an apexcardiography signal, a blood pressure signal, and/or an echocardiography signal. Further, the signal indicative of the patient's kinetic activity may be provided by at least one of an accelerometer, an inclinometer, an actigraph, an imaging system, a dynamometer, a gyroscope, and/or an electromyogram (EMG). In addition, the signal indicative of the patient's dermal activity may be provided by at least one of a skin resistance sensor, a skin temperature sensor, a skin blood flow sensor, and/or a skin sweat gland activity sensor.

In addition, the method may include classifying an epileptic event based upon at least one of the patient's cardiac activity, a body movement or movement force data, and/or the patient's dermal activity.

In another embodiment, a method of treating a medical condition in a patient using an implantable medical device where the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve where the method includes: receiving via one or more processors of a medical device at least one of a kinetic signal indicative of a patient's kinetic activity and a cardiac signal indicative of a patient's cardiac activity; determining via the one or more processors of the medical device at least one of a kinetic feature from the kinetic signal and a cardiac feature from the cardiac signal; detecting via the one or more processors of the medical device an onset of a seizure based on the at least one of a change in the kinetic feature and a change in the cardiac feature; classifying an occurrence of the seizure, based at least in part on the kinetic feature or the cardiac feature; and/or based on at least one of: a detection of an impending seizure and the onset of the seizure; providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal; switching from the first polarity configuration to a second polarity configuration upon termination of the first electrical signal where the first electrode functions as the anode and the second electrode functions as the cathode in the second polarity configuration; and/or providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal where the classification includes determining that the occurrence of the seizure is: an epileptic seizure or a non-epileptic seizure; a partial seizure or a partial complex seizure; and a partial seizure or a generalized seizure.

In addition, the method may include logging an occurrence of the onset of the seizure; logging a time of the occurrence of the onset of the seizure; logging a date of the occurrence of the onset of the seizure; logging a result of the classification of the seizure; providing at least one of a warning, an alarm or an alert to the patient, a caregiver or a health care provider; providing a therapy to prevent, abort, reduce a severity, or reduce a duration of the seizure; assessing at least one of an awareness or responsiveness of the patient during the seizure; assessing a severity of the seizure; determining an end of the seizure; determining a beginning of a post-ictal period; and/or determining an end of the post-ictal period; and assessing a patient's post-ictal impairment or recovery from the seizure.

Further, the method may include logging an occurrence of the classified seizure; logging a time of the occurrence of the classified seizure; logging a date of the occurrence of the classified seizure; logging a time for the warning, the alarm or the alert to the patient, the caregiver or the health care provider; logging the provided therapy for the classified seizure; logging the assessment of the awareness or responsiveness of the patient during the classified seizure; logging the assessment of the severity of the classified seizure; logging the end of the classified seizure; logging the beginning of a post-ictal period; logging the end of the post-ictal period; and/or logging the assessment of the patient's post-ictal impairment or recovery from the classified seizure.

In addition, the patient's cardiac activity is one of a heart rate, a heart rate variability, a heart beat morphology, a heart sound, and/or a thoracic chest wall deflection caused by a heart's apex. Further, the signal indicative of the patient's cardiac activity is provided by at least one of an electrocardiogram (EKG) signal, a phonocardiogram (PKG) signal, an apexcardiography signal, a blood pressure signal, and/or an echocardiography signal. In addition, the signal indicative of the patient's kinetic activity is provided by at least one of a force transducer, an accelerometer, an inclinometer, an actigraph, an imaging system, a dynamometer, a gyroscope, and/or an electromyogram (EMG). In addition, classifying an epileptic event may be based upon at least one of the patient's cardiac activity or body movement data.

In another embodiment, a system using an implantable medical device where the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the system includes at least one first sensor configured to receive a signal relating to a dermal activity from a patient, at least one second sensor configured to receive at least one of a signal relating to a cardiac activity from the patient or a signal relating to a body movement from the patient, a feature determination unit configured to determine a dermal activity feature from the signal relating to the dermal activity, and at least one of a cardiac activity feature from the signal relating to the cardiac activity and a kinetic activity feature from the signal relating to the kinetic activity, a detection unit configured to receive the dermal activity feature, and at least one of the cardiac activity feature and the kinetic activity feature, from the feature determination unit and determine an onset of an seizure based upon the received activity features; an action unit configured to receive an indication of an occurrence of the seizure from the detection unit and perform an assessment of an awareness or responsiveness of the patient during the seizure and at least one of: logging the occurrence of the seizure; logging a time of the occurrence of the seizure; logging a date of the occurrence of the seizure; providing at least one of a warning, an alarm or an alert to the patient, a caregiver or a health care provider; providing a therapy to prevent, abort, reduce a severity, or reduce a duration of the seizure; assessing a severity of the seizure; determining an end of the seizure; determining a beginning of a post-ictal period; determining an end of the post-ictal period; and assessing a patient's post-ictal impairment or recovery from the seizure; a classification unit configured to determine that the occurrence of the seizure is: an epileptic seizure or a non-epileptic seizure; a partial seizure or a partial complex seizure; and a partial seizure or a generalized seizure; and/or a signal generator configured to: providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal; switching from the first polarity configuration to a second polarity configuration upon termination of the first electrical signal where the first electrode functions as the anode and the second electrode functions as the cathode in the second polarity configuration; and/or providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal.

In addition, the system may include a spectral analysis unit configured to generate at least one spectral analysis signal from at least one of a signal relating to a second cardiac activity and a signal relating to a second body movement; and wherein the detection unit is further configured to receive the at least one spectral analysis signal from the spectral analysis unit.

Further, the at least one second sensor is selected from an electrocardiogram (EKG) sensor, a phonocardiogram (PKG) sensor, an apexcardiography sensor, a blood pressure sensor, and/or an echocardiography sensor. In addition, the at least one second sensor is selected from a force transducer, an accelerometer sensor, an inclinometer sensor, an actigraph sensor, an imaging system sensor, a dynamometer sensor, a gyroscope sensor, and/or an electromyogram (EMG) sensor. Further, the at least one first sensor is selected from a skin resistance sensor, a skin temperature sensor, a skin blood flow sensor, and/or a skin sweat gland activity sensor.

The above methods may be performed by a computer readable program storage device encoded with instructions that, when executed by a computer, perform the method described herein.

All of the methods and apparatuses disclosed and claimed herein may be made and executed without undue experimentation in light of the present disclosure. While the methods and apparatus of this disclosure have been described in terms of particular embodiments, it will be apparent to those skilled in the art that variations may be applied to the methods and apparatus and in the steps, or in the sequence of steps, of the method described herein without departing from the concept, spirit, and scope of the disclosure, as defined by the appended claims. It should be especially apparent that the principles of the disclosure may be applied to selected cranial nerves other than, or in addition to, the vagus nerve to achieve particular results in treating patients having epilepsy, depression, or other medical conditions.

What is claimed:

1. A method of treating a medical condition in a patient using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method comprising:
    receiving via one or more processors of a medical device a signal indicative of a patient's dermal activity;
    receiving via the one or more processors of the medical device at least one of a kinetic signal indicative of a patient's kinetic activity and a cardiac signal indicative of a patient's cardiac activity;
    determining via the one or more processors of the medical device a dermal activity and a dermal activity feature from the signal indicative of the patient's dermal activity, or determining at least one of a kinetic feature from the kinetic signal and a cardiac feature from the cardiac signal;
    detecting via the one or more processors of the medical device an onset of a seizure based on a change in the dermal activity and at least one of the kinetic feature and the cardiac feature indicative of the onset of the seizure;
    providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal;
    switching from the first polarity configuration to a second polarity configuration upon termination of the first electrical signal where the first electrode functions as the anode and the second electrode functions as the cathode in the second polarity configuration;
    providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal; and
    classifying an occurrence of the seizure, based at least in part on the change in the dermal activity feature, the patient's cardiac activity, or the patient's kinetic activity;
    wherein the classification includes determining that the occurrence of the seizure is: an epileptic seizure or a non-epileptic seizure; a partial seizure or a partial complex seizure; and a partial seizure or a generalized seizure.

2. The method of claim 1, the method further comprising at least one of: logging an occurrence of the onset of the seizure; logging a time of the occurrence of the onset of the seizure; logging a date of the occurrence of the onset of the seizure; logging a result of the classification of the seizure; providing at least one of a warning, an alarm or an alert to the patient, a caregiver or a health care provider; providing a therapy to prevent, abort, reduce a severity, or reduce a duration of the seizure; assessing at least one of an awareness or responsiveness of the patient during the seizure; assessing a severity of the seizure; determining an end of the seizure; determining a beginning of a post-ictal period; determining an end of the post-ictal period; and assessing a patient's post-ictal impairment or recovery from the seizure where the further action is logged into a memory.

3. The method of claim 1, wherein the patient's cardiac activity is one of a heart rate, a heart rate variability, a heart beat morphology, a heart sound, or a thoracic chest wall deflection caused by a heart's apex.

4. The method of claim 1, wherein the signal indicative of the patient's cardiac activity is provided by at least one of a force transducer, an electrocardiogram (EKG) signal, a phonocardiogram (PKG) signal, an apexcardiography signal, a blood pressure signal, and an echocardiography signal.

5. The method of claim 1, wherein the signal indicative of the patient's kinetic activity is provided by at least one of an accelerometer, an inclinometer, an actigraph, an imaging system, a dynamometer, a gyroscope, or an electromyogram (EMG).

6. The method of claim 1, wherein the signal indicative of the patient's dermal activity is provided by at least one of a skin resistance sensor, a skin temperature sensor, a skin blood flow sensor, or a skin sweat gland activity sensor.

7. The method of claim 1, further comprising classifying an epileptic event based upon at least one of the patient's cardiac activity, a body movement or movement force data, or the patient's dermal activity.

8. A method of treating a medical condition in a patient using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, the method comprising:
    receiving via one or more processors of a medical device at least one of a kinetic signal indicative of a patient's kinetic activity and a cardiac signal indicative of a patient's cardiac activity;
    determining via the one or more processors of the medical device at least one of a kinetic feature from the kinetic signal and a cardiac feature from the cardiac signal;
    detecting via the one or more processors of the medical device an onset of a seizure based on the at least one of a change in the kinetic feature and a change in the cardiac feature;
    classifying an occurrence of the seizure, based at least in part on the kinetic feature or the cardiac feature; and
    based on at least one of: a detection of an impending seizure and the onset of the seizure;
    providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal;
    switching from the first polarity configuration to a second polarity configuration upon termination of the first electrical signal where the first electrode functions as the anode and the second electrode functions as the cathode in the second polarity configuration;

providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal;

wherein the classification includes determining that the occurrence of the seizure is: an epileptic seizure or a non-epileptic seizure; a partial seizure or a partial complex seizure; and a partial seizure or a generalized seizure.

9. The method of claim 8, further comprising at least one of:

logging an occurrence of the onset of the seizure; logging a time of the occurrence of the onset of the seizure; logging a date of the occurrence of the onset of the seizure; logging a result of the classification of the seizure; providing at least one of a warning, an alarm or an alert to the patient, a caregiver or a health care provider; providing a therapy to prevent, abort, reduce a severity, or reduce a duration of the seizure; assessing at least one of an awareness or responsiveness of the patient during the seizure; assessing a severity of the seizure; determining an end of the seizure; determining a beginning of a post-ictal period; determining an end of the post-ictal period; and assessing a patient's post-ictal impairment or recovery from the seizure.

10. The method of claim 8, further comprising at least one of:

logging an occurrence of the classified seizure; logging a time of the occurrence of the classified seizure; logging a date of the occurrence of the classified seizure; logging a time for the warning, the alarm or the alert to the patient, the caregiver or the health care provider; logging the provided therapy for the classified seizure; logging the assessment of the awareness or responsiveness of the patient during the classified seizure; logging the assessment of the severity of the classified seizure; logging the end of the classified seizure; logging the beginning of a post-ictal period; logging the end of the post-ictal period; and logging the assessment of the patient's post-ictal impairment or recovery from the classified seizure.

11. The method of claim 8, wherein the patient's cardiac activity is one of a heart rate, a heart rate variability, a heart beat morphology, a heart sound, or a thoracic chest wall deflection caused by a heart's apex.

12. The method of claim 8, wherein the signal indicative of the patient's cardiac activity is provided by at least one of an electrocardiogram (EKG) signal, a phonocardiogram (PKG) signal, an apexcardiography signal, a blood pressure signal, and an echocardiography signal.

13. The method of claim 8, wherein the signal indicative of the patient's kinetic activity is provided by at least one of a force transducer, an accelerometer, an inclinometer, an actigraph, an imaging system, a dynamometer, a gyroscope, or an electromyogram (EMG).

14. The method of claim 8, wherein classifying an epileptic event is based upon at least one of the patient's cardiac activity or body movement data.

15. A system using an implantable medical device, the implantable medical device including a first electrode coupled to a first cranial nerve structure and a second electrode coupled to a second cranial nerve structure, where the first cranial nerve structure is a left portion of a cranial nerve and the second cranial nerve structure is a right portion of the cranial nerve, comprising:

at least one first sensor configured to receive a signal relating to a dermal activity from a patient, at least one second sensor configured to receive at least one of a signal relating to a cardiac activity from the patient or a signal relating to a body movement from the patient, a feature determination unit configured to determine a dermal activity feature from the signal relating to the dermal activity, and at least one of a cardiac activity feature from the signal relating to the cardiac activity and a kinetic activity feature from the signal relating to the kinetic activity, a detection unit configured to receive the dermal activity feature, and at least one of the cardiac activity feature and the kinetic activity feature, from the feature determination unit and determine an onset of an seizure based upon the received activity features;

an action unit configured to receive an indication of an occurrence of the seizure from the detection unit and perform an assessment of an awareness or responsiveness of the patient during the seizure and at least one of:

logging the occurrence of the seizure; logging a time of the occurrence of the seizure; logging a date of the occurrence of the seizure; providing at least one of a warning, an alarm or an alert to the patient, a caregiver or a health care provider; providing a therapy to prevent, abort, reduce a severity, or reduce a duration of the seizure; assessing a severity of the seizure; determining an end of the seizure;

determining a beginning of a post-ictal period; determining an end of the post-ictal period; and assessing a patient's post-ictal impairment or recovery from the seizure;

a classification unit configured to determine that the occurrence of the seizure is: an epileptic seizure or a non-epileptic seizure; a partial seizure or a partial complex seizure; and a partial seizure or a generalized seizure; and a signal generator configured to:

providing a first electrical signal to the first cranial nerve structure of the patient using a first polarity configuration in which the first electrode functions as a cathode and the second electrode functions as an anode, the first electrical signal is configured to induce action potentials in the first cranial nerve structure, wherein a charge accumulates at the anode and the cathode as a result of the first electrical signal;

switching from the first polarity configuration to a second polarity configuration upon termination of the first electrical signal where the first electrode functions as the anode and the second electrode functions as the cathode in the second polarity configuration;

providing a second electrical signal to the second cranial nerve structure in the second polarity configuration, the second electrical signal is configured to induce action potentials in the second cranial nerve structure where at least a portion of the second electrical signal comprises the accumulated charge from the first electrical signal.

16. The system of claim 15, further comprising a spectral analysis unit configured to generate at least one spectral analysis signal from at least one of a signal relating to a second cardiac activity and a signal relating to a second body movement; and wherein the detection unit is further configured to receive the at least one spectral analysis signal from the spectral analysis unit.

17. The system of claim 15, wherein the at least one second sensor is selected from an electrocardiogram (EKG) sensor, a phonocardiogram (PKG) sensor, an apexcardiography sensor, a blood pressure sensor, or an echocardiography sensor.

18. The system of claim 15, wherein the at least one second sensor is selected from a force transducer, an accelerometer sensor, an inclinometer sensor, an actigraph sensor, an imaging system sensor, a dynamometer sensor, a gyroscope sensor, or an electromyogram (EMG) sensor.

19. The system of claim 15, wherein the at least one first sensor is selected from a skin resistance sensor, a skin temperature sensor, a skin blood flow sensor, or a skin sweat gland activity sensor.

\* \* \* \* \*